US010501773B2

(12) United States Patent
Zaman et al.

(10) Patent No.: US 10,501,773 B2
(45) Date of Patent: Dec. 10, 2019

(54) DETECTION AND CLASSIFICATION OF AN ANTICOAGULANT USING A CLOTTING ASSAY

(71) Applicant: Haemonetics Corporation, Braintree, MA (US)

(72) Inventors: Fowzia S. Zaman, Aurora, IL (US); Marc Doubleday, Cary, IL (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 14/813,939

(22) Filed: Jul. 30, 2015

(65) Prior Publication Data

US 2016/0032355 A1 Feb. 4, 2016

Related U.S. Application Data

(60) Provisional application No. 62/031,371, filed on Jul. 31, 2014, provisional application No. 62/111,376, filed on Feb. 3, 2015.

(51) Int. Cl.
*C12Q 1/56* (2006.01)
*G01N 33/86* (2006.01)

(52) U.S. Cl.
CPC .............. *C12Q 1/56* (2013.01); *G01N 33/86* (2013.01); *G01N 2333/96444* (2013.01)

(58) Field of Classification Search
CPC . C12Q 1/56; G01N 33/86; G01N 2333/96444
See application file for complete search history.

(56) References Cited

U.S. PATENT DOCUMENTS

| 2007/0184508 A1 | 8/2007 | Cohen et al. | 435/11 |
| 2012/0202232 A1 | 8/2012 | Braun et al. | 435/13 |
| 2015/0343034 A1* | 12/2015 | Pittman | A61K 38/4846 424/94.2 |

FOREIGN PATENT DOCUMENTS

| EP | 2405274 | 1/2012 |
| JP | 2003-513280 | 4/2003 |
| JP | 2013-524176 | 6/2013 |
| WO | 01/33217 | 5/2001 |
| WO | 2011/120556 | 10/2011 |

OTHER PUBLICATIONS

Mackman et al. The Role of Tissue Factor and Factor Viia in Hemostasis; Anesthesia and Analgesia; vol. 108, No. 5 (2009) pp. 1447-1452.*
McMichael et al. Viscoelastic Coagulation Testing: Technology, Applications and Limitations; Veterinary clinical Pathology, vol. 40, No. 2 (2011) pp. 140-153.*
Siegal et al. Reversal of Novel Oral Anticoagulants in Patients with Major Bleeding; Journal of thrombosis and Thrombolysis, vol. 35 (2013) pp. 391-398.*
Thiruvenkatarajan et al. Coagulation Testing in the Perioperative Period; Indian Journal of Anesthesia, vol. 58, No. 5 (2014) pp. 565-572.*
Schaden et al. Ecarin Modified Rotational Thromboelastometry: A Point-of-Care Applicable Alternative to Monitor the Direct Thrombin Inhibitor Argatroban; Weiner Klinische Wochenschrift, vol. 125, pp. 156-159. (Year: 2013).*
Gonsalves et al. Management of Bleeding Complications in Patients on New Oral Antocoagulants; Journal of Hematology and Transfusion, vol. 2, No. 1, pp. 1-6 (Year: 2014).*
Bates et al., "Coagulation Assays," Circulation, Journal of the American Heart Association, vol. 112, pp. e53-e60, 2005.
Choi et al., "Modified Plasma-Based Ecarin Clotting Time Assay for Monitoring of Recombinant Hirudin During Cardiac Surgery," American Journal of Clinical Pathology, vol. 125, issue 2, pp. 290-295, Feb. 2006.
Davis et al., "The ex vivo reversibility of dabigatran-induced whole-blood coagulopathy as monitored by thromboelastography: Mechanistic implications for clinical medicine," Thrombosis and Haemostasis, vol. 108, issue 3, 3 pages, Sep. 2012.
Di Nisio, et al, "Direct Thrombin Inhibitors," The New England Journal of Medicine, vol. 353, pp. 1028-1040, Sep. 8, 2005.
Dinkelaar et al., "Global coagulation tests: their applicability for measuring direct factor Xa- and thrombin inhibition and reversal of anticoagulation by prothrombin complex concentrate," Clinical Chemistry and Laboratory Medicine, vol. 52, issue 11, pp. 1615-1623, Nov. 2014.
European Patent Office, International Search Report, International Application No. PCT/US2015/042915, together with the Written Opinion of the International Searching Authority, 11 pages, Oct. 7, 2015.

(Continued)

*Primary Examiner* — Sharmila G Landau
*Assistant Examiner* — Paul C Martin
(74) *Attorney, Agent, or Firm* — Sunstein Kann Murphy & Timbers LLP

(57) ABSTRACT

In some embodiments, the invention provides methods for detecting and/or classifying an anticoagulant at a therapeutically relevant amount or higher in a patient, including subjecting a sample of a control blood component (known not to contain the anticoagulant) to a clotting assay in the presence of a Factor Xa reagent to obtain a control clotting measurement; and subjecting a sample of a blood component from a patient suspected of having the anticoagulant to the clotting assay in the presence of the Factor Xa reagent to obtain a patient clotting measurement, wherein the patient clotting measurement sample greater than the control clotting measurement indicates the presence of the anticoagulant at a therapeutically relevant amount or higher in the patient. In some embodiments, the invention includes methods for classifying an anticoagulant as an anti-Factor Xa or a direct thrombin inhibitor anticoagulant using a clotting assay in the presence of an ecarin reagent.

11 Claims, 26 Drawing Sheets

(56) References Cited

OTHER PUBLICATIONS

Favaloro et al., "Laboratory testing of anticoagulants: the present and the future," Pathology, vol. 43, issue 7, pp. 682-692, Dec. 2011.
Hawes et al., "Performance of coagulation tests in patients on therapeutic doses of dabigatran: a cross-sectional pharmacodynamic study based on peak and trough plasma levels," Journal of Thrombosis and Haemostasis, vol. 11, pp. 1493-1502, Oct. 7, 2013.
Koster et al., "Monitoring of Bivalirudin Anticoagulation During and After Cardiopulmonary Bypass Using an Ecarin-Activated TEG® System," Journal of Cardiac Surgery, vol. 23, issue 4, pp. 321-323, Jul./Aug. 2008.
Mani et al., "Measuring the anticoagulant effects of target specific oral anticoagulants-reasons, methods and current limitations," Journal of Thrombosis and Thrombolysis, vol. 36, issue 2, pp. 187-194, 2013.
Omert, "TEG monitoring of new oral anticoagulants," Haemonetics, 30 pages, Sep. 2, 2013.
Sucker et al., "Rotational thrombelastometry for the bedside monitoring of recombinant hirudin," Acta Anaethesiologica Scandinavica, vol. 52, pp. 358-362, 2008.
Von Kier et al., "411—TEG® R-time is Directly Related to Hiridin Concentration in Whole Blood Following Stimulation with the Snake Venom Ecarin," American Society of Anesthesiologists, 1 page, Oct. 14-18, 2000.
Weitz et al., "New oral anticoagulants: which one should my patient use?," American Society of Hematology, pp. 536-540, 2012.
Xu et al., "Differential profiles of thrombin inhibitors (heparin, hirudin, bivalirudin, and dabigatran) in the thrombin generation assay and thromboelastography in vitro," Blood Coagulation and Fibrinolysis, vol. 24, pp. 332-338, Apr. 2013.
Tripodi "The Laboratory and the New Oral Anticoagulants," Clinical Chemistry, vol. 59, No. 2, pp. 353-362, 2013.

\* cited by examiner

Fig. 17

|  |  | ACT (sec) | | |
| --- | --- | --- | --- | --- |
|  |  | no ecarin | with ecarin | P-value |
| Apixaban (ng/ml) | 1000 | ~ 144 | Decrease | <.001 § |
|  | 500 | ~ 122 | Decrease | <.001 § |
|  | 250 | ~ 118 | Decrease | <.001 § |
|  | 0 | ~ 103 | Decrease | <.001 § |
| Rivaroxiban (ng/ml) | 500 | ~ 154 | Decrease | <.001 § |
|  | 89 | ~ 120 | Decrease | <.001 § |
|  | 22 | ~ 110 | Decrease | <.001 § |
|  | 0 | ~ 108 | Decrease | <.001 § |
| Dabigatran (ng/ml) | 500 | ~ 342 | Decrease | <.001 § |
|  | 250 | ~ 237 | Decrease | <.001 § |
|  | 50 | ~ 146 | Decrease | <.001 § |
|  | 0 | ~ 108 | Decrease | <.001 § |

Fig. 18

DETECTION AND CLASSIFICATION OF AN
ANTICOAGULANT USING A CLOTTING
ASSAY

CROSS-REFERENCE TO RELATED APPLICATIONS

This application claims priority to U.S. provisional application No. 62/031,371 filed Jul. 31, 2014 and U.S. provisional application No. 62/111,376 filed Feb. 3, 2015, each of which is hereby incorporated by reference in its entirety.

BACKGROUND

The present invention relates to the field of coagulation and hemostasis.

With the aging of the population the risk of diseases involving the heart and circulation system has become a growing concern. Anticoagulants have been used to combat and/or manage (e.g., prevent) syndromes including atrial fibrillation, pulmonary embolism, deep vein thrombosis, venous thromboembolism, congestive heart failure, stroke, myocardial infarction, and hypercoagulability in patients. In the past, the anticoagulant drug warfarin, which reduced the functional levels of all of the vitamin K-dependent clotting factors, was often used. However, recently improved anticoagulants have been developed that specifically target certain factors in the coagulation cascade.

For example, the introduction of oral anticoagulants has changed the management of patients with venous and arterial thromboembolic diseases. Unlike traditional oral vitamin K antagonists (VKA), the recently developed oral anticoagulant that do not universally reduce vitamin K-dependent factors are given at fixed doses and have a lower potential for drug and food interactions, thus eliminating the requirement for routine laboratory monitoring (Ansell J. et al., Chest 133: 160S-198S, 2008; Ageno W. et al., Chest 141: e44S-88S, 2012). These novel agents show similar or improved efficacy and safety profiles compared with VKA drugs such as warfarin and established parenteral agents including unfractionated heparin and low molecular weight heparin.

However, these new oral anticoagulants present management challenges to both clinicians and laboratory personnel when patients develop bleeding diatheses (e.g., due to a traumatic injury or during surgery). Lack of a readily available method to determine the degree of anticoagulation creates a major challenge to clinicians treating bleeding patients who are potentially receiving an anticoagulant. In some cases, there are no useful methods to detect and monitor these agents (see Miyares and Davis, Am. J. Health. Syst. Pharm. 69: 1473-1484, 2012).

It would be useful to have a rapid method to detect the presence of an anticoagulant in a sample taken from the patient. It would also be useful to identify which type of anticoagulant is in the patient's sample.

SUMMARY OF THE EMBODIMENTS

In some embodiments, the invention provides a rapid and accurate method to detect the presence and reversal of an anticoagulant in a sample taken from the patient. In some embodiments, the invention provides a rapid and accurate method to identify which type of anticoagulant is in the sample.

Accordingly, in a first aspect, the invention provides a method for detecting an anticoagulant at least at a therapeutically relevant amount (i.e., a therapeutically relevant amount or higher) in a patient suspected of having an anticoagulant. The method comprises (a) subjecting a control sample of a control blood component, the control sample known not to contain the anticoagulant, to a clotting assay in the presence of a Factor Xa reagent to obtain a clotting measurement of the control sample; and (b) subjecting a patient sample of a blood component from the patient suspected of having the anticoagulant to the clotting assay in the presence of the Factor Xa reagent to obtain the clotting measurement of the patient sample, wherein the clotting measurement of the patient sample greater than the clotting measurement of the control sample indicates the presence of the anticoagulant at a therapeutically relevant amount in the patient and wherein the clotting measurement of the patient sample less than or equal to the clotting measurement of the control sample indicates the absence of the anticoagulant at a therapeutically relevant amount in the patient. In some embodiments, the anticoagulant is an oral anticoagulant. The oral anticoagulant may be a direct thrombin inhibitor or may be a Factor Xa inhibitor.

In some embodiments, the method further comprising classifying the anticoagulant identified as being present in the patient by (a) subjecting a control sample of the control blood component to a clotting assay in the presence of an ecarin reagent to obtain a control ecarin clotting measurement; and (b) subjecting a patient sample of the blood component from the patient to the clotting assay in the presence of the ecarin reagent to obtain a patient ecarin clotting measurement, wherein the patient ecarin clotting measurement greater than the control ecarin clotting measurement identifies the anticoagulant as a direct thrombin inhibitor (DTI) in the patient and wherein the patient ecarin clotting measurement less than or equal to the control ecarin clotting measurement identifies the anticoagulant as an anti-Factor Xa anticoagulant in the patient.

In another aspect, the invention provides a method for detecting and/or classifying an anticoagulant at a therapeutically relevant amount or higher in a patient suspected of having an anticoagulant comprising subjecting a first sample of a blood component from the patient to a clotting assay in the presence of a Factor Xa reagent to obtain a patient Factor Xa clotting measurement, subjecting a second sample of the blood component from the patient to a clotting assay in the presence of an ecarin reagent to obtain a patient ecarin clotting measurement; and comparing the patient Factor Xa clotting measurement to a control Factor Xa clotting measurement from a control blood component known to lack the anticoagulant and comparing the patient ecarin clotting measurement to a control ecarin clotting measurement from the control blood component; wherein the patient Ecarin clotting measurement greater than the control ecarin clotting measurement identifies the presence of the anticoagulant at or above a therapeutically relevant amount in the patient and identifies the anticoagulant as a Direct Thrombin Inhibitor (DTI), and wherein the patient Factor Xa clotting measurement of greater than the control Factor Xa clotting measurement of identifies the presence of the anticoagulant at or above a therapeutically relevant amount in the patient and identifies the anticoagulant as an anti-Factor Xa anticoagulant, and wherein the patient Factor Xa clotting measurement less than or equal to the control Factor Xa clotting measurement identifies absence of an anticoagulant at or above a therapeutically relevant amount in the patient.

In another aspect, the invention provides a method for detecting and/or classifying an anticoagulant at a therapeutically relevant amount or higher than a therapeutically relevant amount in a blood component from a patient, comprising: detecting the presence of an anticoagulant in the blood component by (i) subjecting a first portion of a control blood component known not to contain the anticoagulant, to a clotting assay in the presence of a Factor Xa reagent to obtain a control Factor Xa clotting measurement; and (ii) subjecting a first portion of the blood component from the patient to the clotting assay in presence of the Factor Xa reagent to obtain a patient Factor Xa clotting measurement, wherein the patient Factor Xa clotting measurement that is greater than the control Factor Xa clotting measurement indicates the presence of the anticoagulant at a therapeutic level in the patient blood component and wherein the patient Factor Xa clotting measurement that is less than or equal to the control Factor Xa clotting measurement indicates the absence of the anticoagulant at a therapeutically relevant amount in the patient blood component and classifying the anticoagulant, if present, in the patient blood component, by (i) subjecting a second portion of the control blood component to a clotting assay in the presence of an ecarin reagent to obtain a control ecarin clotting measurement; and (ii) subjecting a second portion of the patient blood component to the clotting assay in the presence of the ecarin reagent to obtain a patient ecarin clotting measurement, wherein the patient ecarin clotting measurement that is greater than the control ecarin clotting measurement identifies the anticoagulant as a direct thrombin inhibitor (DTI) and wherein the patient ecarin clotting measurement that is less than or equal to the control ecarin clotting measurement identifies the anticoagulant as an anti-Factor Xa anticoagulant.

In some embodiments, the clotting assay is selected from the group consisting of a prothrombin time (PT) assay, an activated partial thromboplastin time (APTT) assay, and the activated clotting time (ACT) assay.

In some embodiments, the clotting measurement of the control sample is a range of at least two clotting measurements of at least two control samples from at least two control blood components known to lack the anticoagulant.

In some embodiments, the clotting assay is a viscoelastic analysis clotting assay. In some embodiments, the viscoelastic analysis is performed using a container containing the sample on an interior of the container. In some embodiments, the viscoelastic analysis is performed using the container and a pin, wherein the pin moves relative to the container. In some embodiments, the viscoelastic analysis is performed using the container and a pin, wherein the container moves relative to the pin. In some embodiments, the container lacks a bottom surface.

In various embodiments, the patient is a human. In some embodiments, patient is undergoing a condition including surgery, trauma, bleeding, stroke, or a thromboembolic event.

In some embodiments, the anticoagulant is an oral anticoagulant (e.g., an anti-Factor Xa anticoagulant or a DTI anticoagulant).

In various embodiments, the patient Factor Xa clotting measurement that is at least 1.25 times greater than the control Factor Xa clotting measurement identifies the presence of the anticoagulant at a therapeutically relevant amount or higher in the patient. In some embodiments, the patient Factor Xa clotting measurement that is at least 1.5 times greater than the control Factor Xa clotting measurement identifies the presence of the anticoagulant at a therapeutically relevant amount or higher in the patient.

In various embodiments, the patient ecarin clotting measurement that is at least 1.25 times greater than the control ecarin clotting measurement identifies the presence of the anticoagulant at a therapeutically relevant amount or higher in the patient. In some embodiments, the patient ecarin clotting measurement that is at least 1.5 times greater than the control ecarin clotting measurement identifies the presence of the anticoagulant at a therapeutically relevant amount or higher in the patient.

In various embodiments, the patient identified as comprising the presence of the anticoagulant at a therapeutically relevant amount or higher is administered a therapeutically relevant amount of a reversal agent. In some embodiments, the reversal agent is prothrombin complex concentrates. In some embodiments, the patient identified as comprising the presence of a DTI anticoagulant at a therapeutically relevant amount or higher is administered a therapeutically relevant amount of a reversal agent that reverses the DTI anticoagulant (e.g., idarucizumab). In some embodiments, the patient identified as comprising the presence of an anti-Factor Xa anticoagulant at a therapeutically relevant amount or higher is administered a therapeutically relevant amount of a reversal agent that reverses the anti-Factor Xa anticoagulant (e.g., andexanet).

In another aspect, the invention provides a method for detecting and/or classifying an anticoagulant at a therapeutically relevant amount (or higher) in a patient suspected of having an anticoagulant. The method includes (a) detecting the presence of an anticoagulant in a blood component from the patient, comprising the steps of: (i) subjecting a first portion of a sample of a control blood component, the control blood component known not to contain the anticoagulant, to a clotting assay in the presence of a Factor Xa reagent to obtain a Factor Xa clotting measurement of the control sample (i.e., a control Factor Xa clotting measurement); and (ii) subjecting a first portion of a sample of a blood component from the patient, the patient suspected of having an anticoagulant, to the clotting assay in the presence of the Factor Xa reagent to obtain the Factor Xa clotting measurement of the patient sample (i.e., a patient Factor Xa clotting measurement), wherein the Factor Xa clotting measurement of the patient sample greater than the Factor Xa clotting measurement of the control sample indicates the presence of the anticoagulant at a therapeutically relevant amount in the patient and wherein the Factor Xa clotting measurement of the second sample less than or equal to the Factor Xa clotting measurement of the control sample indicates the absence of the anticoagulant at a therapeutically relevant amount in the patient; and (b) classifying the anticoagulant, if detected as being present, in the patient, comprising the steps (i) subjecting a second portion of the sample of the control blood component to the clotting assay in the presence of an ecarin reagent to obtain the ecarin clotting measurement of the control sample (i.e., the control ecarin clotting measurement); and (ii) subjecting a second portion of the sample of the blood component from the patient to the clotting assay in the presence of the ecarin reagent to obtain the ecarin clotting measurement of the patient sample (i.e., the patient ecarin clotting measurement), wherein the ecarin clotting measurement of the patient sample greater than the ecarin clotting measurement of the control sample identifies the anticoagulant as a direct thrombin inhibitor (DTI) and wherein the ecarin clotting measurement of the patient sample that is less than or equal to the ecarin clotting measurement of the control sample identifies the anticoagulant as an anti-Factor Xa reagent.

In some embodiments, the clotting assay is selected from the group consisting of a prothrombin time (PT) assay, an activated partial thromboplastin time (APTT) assay, and the activated clotting time (ACT) assay.

In some embodiments, the clotting measurement of the control sample is a range of at least two clotting measurements of at least two control samples from at least two control blood components known to lack the anticoagulant. For example, in some embodiments, the control Factor Xa clotting measurement is a range of at least two Factor Xa clotting measurements of at least two control blood components known to lack the anticoagulant. In some embodiments, the control ecarin clotting measurement is a range of at least two ecarin clotting measurements of at least two control blood components known to lack the anticoagulant.

In some embodiments, the clotting assay is a viscoelastic analysis clotting assay. In some embodiments, the viscoelastic analysis is performed using a container containing the sample on an interior of the container. In some embodiments, the viscoelastic analysis is performed using the container and a pin, wherein the pin moves relative to the container. In some embodiments, the viscoelastic analysis is performed using the container and a pin, wherein the container moves relative to the pin. In some embodiments, the container lacks a bottom surface.

In various embodiments, the patient is a human. In some embodiments, patient is undergoing a condition including surgery, trauma, bleeding, stroke, or a thromboembolic event.

In some embodiments, the anticoagulant is an oral anticoagulant (e.g., an anti-Factor Xa anticoagulant or a DTI anticoagulant).

In various embodiments, the patient Factor Xa clotting measurement that is at least 1.25 times greater than the control Factor Xa clotting measurement identifies the presence of the anticoagulant at a therapeutically relevant amount or higher in the patient. In some embodiments, the patient Factor Xa clotting measurement that is at least 1.5 times greater than the control Factor Xa clotting measurement identifies the presence of the anticoagulant at a therapeutically relevant amount or higher in the patient.

In various embodiments, the patient ecarin clotting measurement that is at least 1.25 times greater than the control ecarin clotting measurement identifies the presence of the anticoagulant at a therapeutically relevant amount or higher in the patient. In some embodiments, the patient ecarin clotting measurement that is at least 1.5 times greater than the control ecarin clotting measurement identifies the presence of the anticoagulant at a therapeutically relevant amount or higher in the patient.

In various embodiments, the patient identified as comprising the presence of the anticoagulant at a therapeutically relevant amount or higher is administered a therapeutically relevant amount of a reversal agent. In some embodiments, the reversal agent is prothrombin complex concentrates. In some embodiments, the patient identified as comprising the presence of a DTI anticoagulant at a therapeutically relevant amount or higher is administered a therapeutically relevant amount of a reversal agent that reverses the DTI anticoagulant (e.g., idarucizumab). In some embodiments, the patient identified as comprising the presence of an anti-Factor Xa anticoagulant at a therapeutically relevant amount or higher is administered a therapeutically relevant amount of a reversal agent that reverses the anti-Factor Xa anticoagulant (e.g., andexanet).

In another aspect, the method for detecting reversal of an anticoagulant at a therapeutically relevant amount or higher in a patient suspected of having an anticoagulant. The method includes by (a) subjecting a sample of the control blood component known to lack (i.e., have the absence of) an anticoagulant to a clotting assay in the presence of an ecarin reagent to obtain a control ecarin clotting measurement; (b) subjecting a sample of the control blood component known to lack (i.e., have the absence of) an anticoagulant to a clotting assay in the presence of a Factor Xa reagent to obtain a control Factor Xa clotting measurement; (c) subjecting a blood component from a patient known or suspected to contain a reversal agent or antidote (e.g., idarucizumab or andexanet) in the presence or absence of an anticoagulant to a clotting assay in the presence of an Ecarin reagent to obtain a patient Ecarin clotting measurement and (d) subjecting a blood component from a patient known or suspected to contain a reversal agent or antidote (e.g., idarucizumab or andexanet) in the presence or absence of an anticoagulant to a clotting assay in the presence of a Factor Xa reagent to obtain a patient Factor Xa clotting measurement, and comparing the control ecarin clotting measurement to the patient ecarin clotting measurement and comparing the control Factor Xa clotting measurement to the patient Factor Xa measurement. When the patient Ecarin clotting measurement and/or the patient Factor Xa clotting measurement is less than or equal to the control Ecarin clotting measurement and/or the control Factor Xa clotting measurement, the patient is identified as comprising a reversal agent that has reversed the anticoagulation activity of the anticoagulant in the patient. In some embodiments, the reversal is complete reversal of the anticoagulation activity of the anticoagulant in the patient. In some embodiments, the reversal is partial reversal of the anticoagulation activity of the anticoagulant in the patient. In some embodiments, the reversal agent is a prothrombin complex concentrate (PCC) or an active substance (such as a monoclonal antibody or peptide) specific for reversing a direct thrombin inhibitor (e.g., idarucizumab) or for reversing a Factor Xa inhibitor (e.g., andexanet) or an agent that reverses both Direct Thrombin Inhibitors and Factor Xa inhibitors.

In some embodiments, the anticoagulant is an oral anticoagulant. The oral anticoagulant may be a direct thrombin inhibitor or may be a Factor Xa inhibitor.

In some embodiments, the clotting assay is selected from the group consisting of a prothrombin time (PT) assay, an activated partial thromboplastin time (APTT) assay, and the activated clotting time (ACT) assay.

In some embodiments, the clotting measurement of the control sample is a range of at least two clotting measurements of at least two control samples from at least two control blood components known to lack the anticoagulant.

In some embodiments, the clotting assay is a viscoelastic analysis clotting assay. In some embodiments, the viscoelastic analysis is performed using a container containing the sample on an interior of the container. In some embodiments, the viscoelastic analysis is performed using the container and a pin, wherein the pin moves relative to the container. In some embodiments, the viscoelastic analysis is performed using the container and a pin, wherein the container moves relative to the pin. In some embodiments, the container lacks a bottom surface.

In various embodiments, the patient is a human. In some embodiments, patient is undergoing a condition including surgery, trauma, bleeding, stroke, or a thromboembolic event.

In some embodiments, the Factor Xa clotting measurement of the control sample is a range of at least two Factor Xa clotting measurements of at least two control samples from at least two control blood components known to lack the anticoagulant. In some embodiments, the ecarin clotting measurement of the control blood component is a range of at least two ecarin clotting measurements of at least two control blood components known to lack the anticoagulant.

In another aspect, the invention provides a method for detecting an anticoagulant at a therapeutically relevant amount or higher in a patient suspected of having an anticoagulant, the method comprising subjecting a patient sample of a blood component from the patient to a clotting assay in the presence of a Factor Xa reagent to obtain a clotting measurement of the patient sample, wherein the clotting measurement of the patient sample greater than a clotting measurement of a control sample of a control blood component known to lack the anticoagulant identifies the presence of the anticoagulant at a therapeutically relevant amount in the patient.

In some embodiments, the clotting measurement of the patient sample that is at least 1.25 times greater than a clotting measurement of the control sample identifies the presence of the anticoagulant at a therapeutically relevant amount in the patient. In some embodiments, the clotting measurement of the patient sample that is at least 1.5 times greater than a clotting measurement of the control sample identifies the presence of the anticoagulant at a therapeutically relevant amount in the patient.

In some embodiments, the clotting assay is selected from the group consisting of a prothrombin time (PT) assay, an activated partial thromboplastin time (APTT) assay, and the activated clotting time (ACT) assay.

In some embodiments, the clotting measurement of the control sample is a range of at least two clotting measurements of at least two control samples from at least two control blood components known to lack the anticoagulant.

In some embodiments, the clotting assay is a viscoelastic analysis clotting assay. In some embodiments, the viscoelastic analysis is performed using a container containing the sample on an interior of the container. In some embodiments, the viscoelastic analysis is performed using the container and a pin, wherein the pin moves relative to the container. In some embodiments, the viscoelastic analysis is performed using the container and a pin, wherein the container moves relative to the pin. In some embodiments, the container lacks a bottom surface.

In various embodiments, the patient is a human. In some embodiments, patient is undergoing a condition including surgery, trauma, bleeding, or a thromboembolic event.

In some embodiments, the clotting measurement of the control sample is a range of at least two clotting measurements of at least two control samples from at least two control blood components known to lack the anticoagulant.

In some embodiments, the anticoagulant is an oral anticoagulant. The oral anticoagulant may be a direct thrombin inhibitor or may be a Factor Xa inhibitor.

In yet a further aspect, the invention provides a method for classifying an anticoagulant at a therapeutically relevant amount or higher in a patient suspected of having an anticoagulant. The method includes (a) subjecting a first patient sample of a blood component from the patient to a clotting assay in the presence of a Factor Xa reagent to obtain a Factor Xa clotting measurement of the patient blood component, wherein the Factor Xa clotting measurement of the patient blood component greater than a Factor Xa clotting measurement of a control blood sample of a control blood component known to lack the anticoagulant identifies the presence of the anticoagulant at a therapeutically relevant amount in the patient; and (b) subjecting a second patient sample of the blood component from the patient to the clotting assay in the presence of an ecarin reagent to obtain the ecarin clotting measurement of the patient blood component; wherein the ecarin clotting measurement of the second patient sample greater than an ecarin clotting measurement of a control sample of the control blood component identifies the anticoagulant as a direct thrombin inhibitor (DTI) and wherein the ecarin clotting measurement of the second patient sample less than or equal to the ecarin clotting measurement of the control sample identifies the anticoagulant as an anti-Factor Xa reagent.

In another aspect, the invention provides a method for detecting and classifying an anticoagulant at a therapeutically relevant amount or higher in a patient. The method includes subjecting a control sample of a control blood component (known not to contain the anticoagulant), to a clotting assay in the presence of an ecarin reagent to obtain a control ecarin measurement; and subjecting a sample of a blood component from the patient suspected of having the anticoagulant to the clotting assay in the presence of the ecarin reagent to obtain a patient ecarin clotting measurement, wherein the clotting measurement of the patient sample greater than the clotting measurement of the control sample indicates the presence of the anticoagulant at a therapeutically relevant amount or higher in the patient and classifies it as a DTI.

The invention also provides a method for detecting and classifying an anticoagulant at a therapeutically relevant amount or higher in a patient suspected of having an anticoagulant. The method includes (a) subjecting a first patient sample of a blood component from the patient to a clotting assay in the presence of an ecarin reagent to obtain an ecarin clotting measurement of the patient blood component, wherein the ecarin clotting measurement of the patient blood component greater than an ecarin clotting measurement of a control blood sample of a control blood component known to lack the anticoagulant identifies the presence of the anticoagulant at a therapeutically relevant amount in the patient and identifies the anticoagulant as a direct thrombin inhibitor (DTI); and (b) subjecting a second patient sample of the blood component from the patient to the clotting assay in the presence of a Factor Xa reagent to obtain the Factor Xa clotting measurement of the second patient sample; wherein the Factor Xa clotting measurement of the second patient sample greater than a Factor Xa clotting measurement of a control sample of the control blood component identifies the presence of the anticoagulant at a therapeutically relevant amount in the patient and identifies the anticoagulant as an anti-Factor Xa and wherein the Factor Xa clotting measurement of the second patient sample less than or equal to the Factor Xa clotting measurement of the control sample identifies the sample as having no anticoagulant.

In some embodiments, the Factor Xa clotting measurement of the patient sample that is at least 1.25 times greater than a Factor Xa clotting measurement of the control sample identifies the presence of the anticoagulant at a therapeutically relevant amount in the patient. In some embodiments, the Factor Xa clotting measurement of the patient sample that is at least 1.5 times greater than a Factor Xa clotting measurement of the control sample identifies the presence of the anticoagulant at a therapeutically relevant amount in the patient.

In some embodiments, the ecarin clotting measurement of the patient sample that is at least 1.25 times greater than the ecarin clotting measurement of the control sample identifies the anticoagulant as a direct thrombin inhibitor (DTI). In some embodiments, the ecarin clotting measurement of the patient sample that is at least 1.5 times greater than the ecarin clotting measurement of the control sample identifies the anticoagulant as a direct thrombin inhibitor (DTI).

In some embodiments, the anticoagulant is an oral anticoagulant. The oral anticoagulant may be a direct thrombin inhibitor or may be a Factor Xa inhibitor.

In some embodiments, the clotting assay is selected from the group consisting of a prothrombin time (PT) assay, an activated partial thromboplastin time (APTT) assay, and the activated clotting time (ACT) assay.

In some embodiments, the clotting measurement of the control sample is a range of at least two clotting measurements of at least two control samples from at least two control blood components known to lack the anticoagulant.

In some embodiments, the clotting assay is a viscoelastic analysis clotting assay. In some embodiments, the viscoelastic analysis is performed using a container containing the sample on an interior of the container. In some embodiments, the viscoelastic analysis is performed using the container and a pin, wherein the pin moves relative to the container. In some embodiments, the viscoelastic analysis is performed using the container and a pin, wherein the container moves relative to the pin. In some embodiments, the container lacks a bottom surface.

In various embodiments, the patient is a human. In some embodiments, patient is undergoing a condition including surgery, trauma, bleeding, stroke, or a thromboembolic event.

In some embodiments, the Factor Xa clotting measurement of the control sample is a range of at least two Factor Xa clotting measurements of at least two control samples from at least two control blood components known to lack the anticoagulant. In some embodiments, the ecarin clotting measurement of the control blood component is a range of at least two ecarin clotting measurements of at least two control blood components known to lack the anticoagulant.

In various embodiments, the patient identified as comprising the presence of the anticoagulant at a therapeutically relevant amount or higher is administered a therapeutically relevant amount of a reversal agent. In some embodiments, the reversal agent is prothrombin complex concentrates. In some embodiments, the patient identified as comprising the presence of a DTI anticoagulant at a therapeutically relevant amount or higher is administered a therapeutically relevant amount of a reversal agent that reverses the DTI anticoagulant. In some embodiments, the reversal agent that reverses the DTI anticoagulant is idarucizumab. In some embodiments, the patient identified as comprising the presence of an anti-Factor Xa anticoagulant at a therapeutically relevant amount or higher is administered a therapeutically relevant amount of a reversal agent that reverses the anti-Factor Xa anticoagulant. In some embodiments, the reversal agent that reverses the anti-Factor Xa anticoagulant is andexanet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIG. 2A depicts the prothrombin time (PT) clotting assay; FIG. 2B shows the activated Partial Thromboplastin Time (aPTT) clotting assay; FIG. 2C shows the activated clotting time (ACT) assay.

FIGS. 7A-7C show the results of the TEG kaolin test R time sensitivity as a function of different concentrations of drug. FIG. 7A shows rivaroxaban; FIG. 7B shows apixaban; and FIG. 7C shows dabigatran. FIG. 7D-7F show the results of Rapid TEG test ACT time sensitivity as a function of different concentrations of drug. FIG. 7D shows rivaroxaban; FIG. 7E shows apixaban; and FIG. 7F shows dabigatran. R times for all doses of dabigatran as well as the highest concentration of apixaban and rivaroxaban tested were significantly higher than the non-spiked blood sample. ACT times for all concentrations of dabigatran as well as the medium and higher concentrations of apixaban and rivaroxaban tested significantly higher than the non-spiked blood sample for ACT. Dotted parallel bars show the normal ranges of R and ACT. Statistically significant between: ¥—higher dose and medium dose; ¤—higher dose and lower dose; ◊—medium dose and lower dose; *—control. In FIGS. 7A-7F, 1 symbol $p<0.05$; 2 symbols $p<0.01$; 3 symbols $p<0.001$. Error bars represent the standard error of three independent experiments measured in triplicate.

FIG. 9A shows the increase in R time as the dosage of dabigatran increases. FIG. 9B (which is an enlargened view of FIG. 7C) shows the increase in R time of the dabigatran-spiked blood as compared the Kaolin R-time of control (unspiked) blood. FIG. 9C (which is an enlargened view of FIG. 8C) shows that when the dabigratran-spiked blood is subjected to the clotting assay in the presence of ecarin and Kaolin, a decrease in the R time results.

FIG. 11A shows an increase in R time at the highest dosage of rivaroxaban. FIG. 11B shows the increase in R time of rivaroxaban-spiked blood as compared to the Kaolin R time of control (unspiked) blood. FIG. 11C shows that when the rivaroxaban-spiked blood is subjected to the clotting assay in the presence of ecarin, a dramatic decrease in the R time results, such that at even the highest dosage, the R time of the rivaroxaban-spiked blood was shorter than the lower boundary of the Kaolin normal range for R time (from control, unspiked blood).

FIG. 15A shows that for the "before" samples, the detection and the classification R times were within the normal R range from control blood. FIG. 15B shows that in the "after" sample in the detection step (i.e., in the presence of the FXa reagent), the R time lengthened such that it was no longer in the normal R range from the control blood. FIG. 15C shows that in the classification step (i.e., in the presence of the ecarin reagent), the R time was within the normal range. These results identified that there was an anticoagulant in the "after" sample, and that the anticoagulant was an anti-Factor Xa anticoagulant.

FIG. 17 shows the TEG Kaolin test coagulation parameters' sensitivity in healthy donor spiked samples with different doses of apixaban, rivaroxaban and dabigatran in the presence or absence of ecarin. In FIG. 17, R—Reaction Time; MRTG—Maximum Rate to Thrombus Generation; TMRTG—Time to Maximum Rate of Thrombus Generation. Statistically significant between: ¥—higher dose and medium dose; ¤—higher dose and lower dose; ◊—medium dose and lower dose;*—the control. §—paired sample with or without Ecarin. SDR—standard error of the mean of three independent experiments measured in triplicate. 1 symbol p<0.05; 2 symbols p<0.01; 3 symbols p<0.001.

FIG. 18 shows the Rapid TEG test coagulation parameters' sensitivity in healthy donor spiked samples with different doses of apixaban, rivaroxaban and dabigatran in the presence or absence of ecarin. Statistically significant between: §—paired sample with or without Ecarin. SDR—standard error of the mean of three independent experiments measured in triplicate. 1 symbol p<0.05; 2 symbols p<0.01; 3 symbols p<0.001.

DETAILED DESCRIPTION OF SPECIFIC EMBODIMENTS

Figure 1:
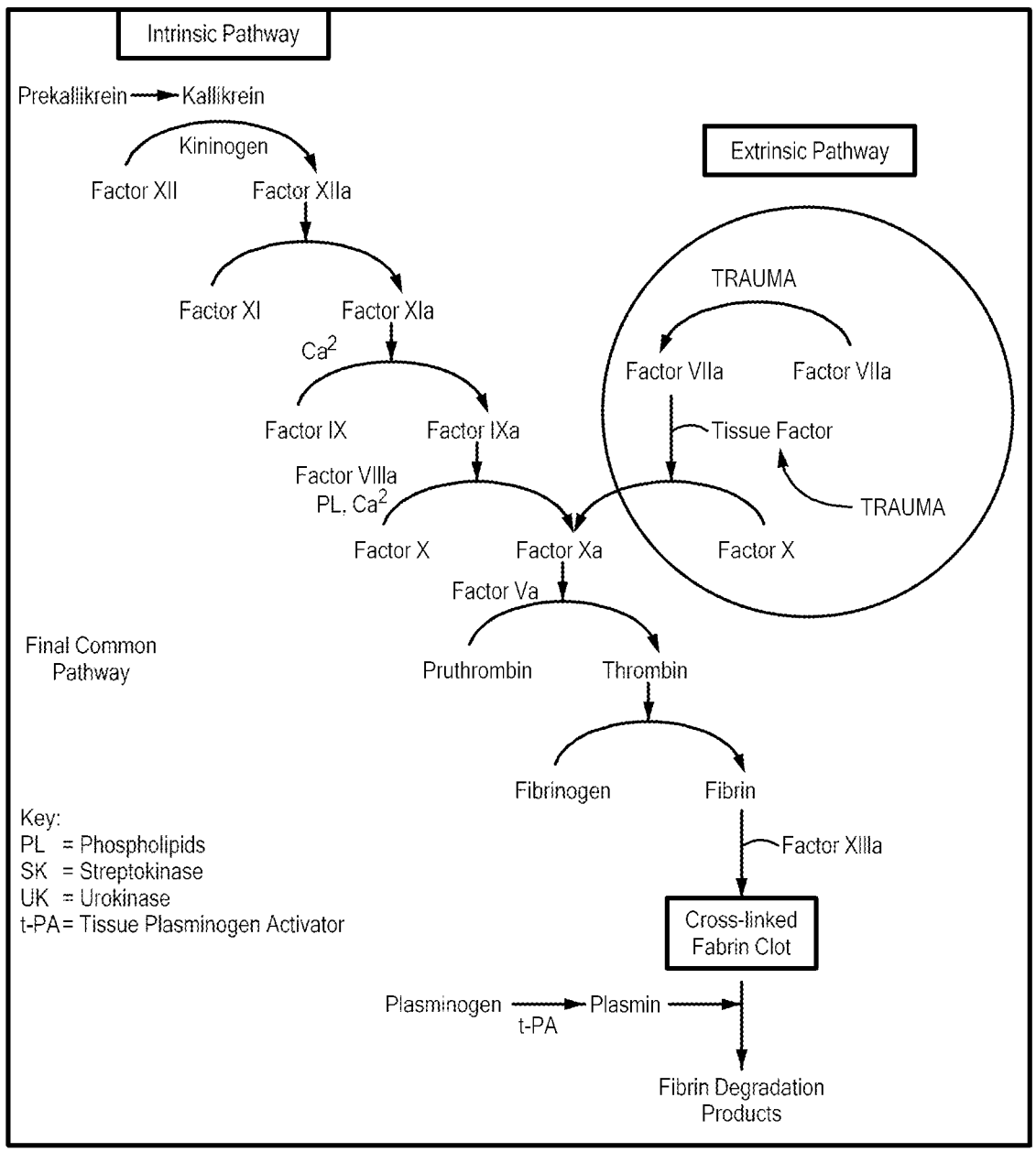
FIG. 1 is a schematic diagram showing the clotting cascade that leads eventually to the formation of a fibrin clot made of cross-linked fibrin. Both an anti-Factor Xa reagent (or drug) and a direct thrombin inhibitor will affect both the extrinsic and intrinsic pathways.

In some embodiments, the invention provides methods and reagents (e.g., cups) for detecting the presence of an anticoagulant in a blood component (e.g., from a patient). In some embodiments, the invention provides methods and reagents for identifying which type of anticoagulant is present in the blood component. In some embodiments, the invention also provides methods and reagents for demonstrating reversal of the anticoagulant effect with a reversal agent or antidote.

The publications (including patent publications), web sites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

In a first aspect, the invention provides a method for detecting an anticoagulant at a therapeutically relevant amount in a patient suspected of having an anticoagulant, the method comprising (a) subjecting a control sample of a control blood component, the control sample known not to contain the anticoagulant, to a clotting assay in the presence of a Factor Xa reagent to obtain a clotting measurement of the control sample; (b) subjecting a patient sample of a blood component from the patient suspected of having the anticoagulant to the clotting assay in the presence of the Factor Xa reagent to obtain the clotting measurement of the patient sample, and (c) comparing the clotting measurement of the patient sample to the clotting measurement of the control sample wherein the clotting measurement of the patient sample greater than the clotting measurement of the control sample indicates the presence of the anticoagulant at a therapeutically relevant amount in the patient and wherein the clotting measurement of the patient sample less than or equal to the clotting measurement of the control sample indicates the absence of the anticoagulant at a therapeutically relevant amount in the patient.

In another aspect, the invention provides a method for detecting an anticoagulant at a therapeutically relevant amount (or higher than a therapeutically relevant amount) in a patient suspected of having an anticoagulant, the method comprising subjecting a patient sample of a blood component from the patient to a clotting assay in the presence of a Factor Xa reagent to obtain a clotting measurement of the patient sample, wherein the clotting measurement of the patient sample greater than a clotting measurement of a control sample of a control blood component known to lack the anticoagulant identifies the presence of the anticoagulant at a therapeutically relevant amount in the patient.

The degree of elongation of the clotting measurement depends on the concentration of the oral anticoagulant in the blood component. The higher the concentration, the greater will be the clotting measurement compared to blood components known to lack any oral anticoagulant. In some embodiments, the clotting measurement of the test blood component that is at least 1.25 times greater than a clotting measurement of a blood component known to lack the anticoagulant identifies the presence of the anticoagulant at a therapeutically relevant amount in the blood component. In some embodiments, the clotting measurement of the test blood component that is at least 1.5 times greater than a clotting measurement of a blood component known to lack the anticoagulant identifies the presence of the anticoagulant at a therapeutically relevant amount in the blood component. In some embodiments, the clotting measurement of the test blood component that is at least 1.75 times greater than a clotting measurement of a blood component known to lack the anticoagulant identifies the presence of the anticoagulant at a therapeutically relevant amount in the blood component. In some embodiments, the clotting measurement of the test blood component that is at least two times greater than a clotting measurement of a blood component known to lack the anticoagulant identifies the presence of the anticoagulant at a therapeutically relevant amount in the blood component.

In some embodiments, the clotting measurement of the control sample may be an average, a median, or a range of at least two clotting measurements of at least two control samples from at least two control blood components known to lack the anticoagulant. For example, a range (which may be referred to as a reference range) may be created from control samples from multiple control blood components (e.g., from multiple donors known to lack the anticoagulant). If an average or mean is used, the clotting measurements from multiple control samples are averaged, and that average number is used as the clotting measurement of the control sample.

In some embodiments, the invention utilizes a clotting assay to assess the functioning of the clotting cascade in the blood component from the patient.

The clotting cascade (or coagulation cascade) is a tightly regulated process by which blood changes from liquid to a solid clot. This process is called coagulation or clotting. FIG. 1 provides a schematic diagram of the clotting cascade. Clotting can be triggered by the extrinsic tissue factor pathway (e.g., by injury or damage to a blood vessel) or by the intrinsic contact activation pathway. The two pathways join in the activation of Factor Xa which then activates prothrombin to thrombin.

By "blood component" is meant one or more components of blood taken, for example, from a patient, where the blood component contains a sufficient quantity of plasma to form a fibrin mediated clot. The blood component may contain at least about 8% plasma on a volume basis (i.e., 8% v/v plasma). The blood component may contain at least about 10% v/v plasma, or at least about 12% v/v plasma, or at least about 15% v/v plasma, or at least about 20% v/v plasma. The patient may be a human, but may also be any other animal (e.g., veterinary animal or exotic animal). Blood is the circulating tissue of an organism that carries oxygen and nutritive materials to the tissues and removes carbon dioxide and various metabolic products for excretion. Blood includes a pale yellow or gray yellow fluid, plasma, in which are suspended red blood cells, white blood cells, and platelets. Blood (sometimes referred to as whole blood) can be fractionated into various components or fractions following density gradient centrifugation. Thus, a blood component includes, without limitation, whole blood (which may be simply referred to as blood), white blood cells including at least about 10% volume plasma, red blood cells including at least about 10% volume plasma, platelets including at least about 10% volume plasma, plasma, and various fractions of blood including at least about 10% volume plasma including the platelet fraction, the red blood cell fraction (e.g., comprised of a majority of red blood cells, and a minority of some white blood cells and plasma), and the buffy coat fraction (e.g., comprised of a majority of white blood cells and platelets, and a minority of some red blood cells and plasma). A blood component also includes any of the above-listed components that also includes a substance (e.g., citric acid or citrate, or heparin) added after the blood component is obtained from the patient that prevents or reduces the coagulation of the blood component.

By "anticoagulant" is meant a substance (i.e., a reagent or a drug) that prevents or reduces coagulation (i.e., clotting) that is present in a blood component of the patient if that substance is taken by or administered to the patient prior to obtaining the blood component from the patient. Such administration may be by any route including oral, parenteral, intravenous, intraperitoneal, intramuscular, subcutaneous, etc. Note that a substance (e.g., heparin or citrate) that is added to a blood component after the blood component is obtained from the patient is not an anticoagulant within this definition.

In some embodiments, the anticoagulant is administered to the patient orally. The orally administered anticoagulant may be referred to as an oral anticoagulant.

By "reversal agent" is meant a substance (e.g., a reagent, antibody, protein or a drug) that reverses the effect of anticoagulation (e.g., the reversal agent reverses the bleeding effected by the anticoagulant) that is present in a blood component of the patient if that substance is taken by or administered to the patient prior to obtaining the blood component from the patient. Such administration may be by any route including oral, parenteral, intravenous, intraperitoneal, intramuscular, subcutaneous, etc.

In some embodiments, the reversal agent is administered to the patient orally.

By a "patient suspected of having an anticoagulant" is meant that the patient (e.g., a human patient) is suspected of having taken an anticoagulant (e.g., through oral administration) before the blood component is obtained from the patient. For example, an unconscious patient may be brought into the emergency room. During surgery, one of the methods described herein may be performed on a sample of the patient's blood component to determine if he/she has taken an anticoagulant by detecting the presence or absence of the anticoagulant in the blood component sample. This information is helpful in attending to the needs of the patient and for reversing the anticoagulant effect as required. A blood component from a patient suspected of having an anticoagulant may be referred to as a "blood component suspected of having an anticoagulant". A sample of a blood component from a patient suspected of having an anticoagulant may be referred to as a "sample suspected of having an anticoagulant".

In some embodiments, the patient from whom the blood component is obtained is a patient suspected of having bleeding diatheses. In some embodiments, the bleeding diatheses may be due to any cause including a congenital hemophilia condition, a vitamin K deficiency. In some cases, the bleeding diatheses may be due to the intake of an anticoagulant by the patient such that it is not known if the patient has bleeding diatheses and, if the patient does have bleeding diatheses, it is not known why the patient has bleeding diatheses. Using the methods described herein, the identification and classification of an anticoagulant (if the patient has taken the anticoagulant) and reversal (if a reversal agent has been administered to the patient) can be determined. In some embodiments, the patient is undergoing (or will shortly be undergoing) a condition that may involve bleeding. For example, the patient may be undergoing surgery, may be being prepared for surgery, may be injured or wounded, may be bleeding, or may have had or is currently having or is suspected to imminently have a thromboembolic event including, without limitation, a stroke, a venous thromboembolic event (VTE), a heart attack, heart failure, an arterial thromboembolic event, and a pulmonary embolism. The patient may be a trauma patient and/or may have internal bleeding.

The recently developed oral anticoagulants that do not universally inhibit all vitamin K-dependent clotting factors can be classified generally into two categories, depending upon the particular clotting factor that the anticoagulant targets.

In some embodiments, the oral anticoagulant is a direct thrombin inhibitor, and may be referred to as a DTI. Thrombin (Clotting Factor IIa) is a central player in the blood clotting process (see FIG. 1). Thrombin plays multiple roles including (a) converting soluble fibrinogen to fibrin; (b) activating factors VI, VIII, XI, and XIII and (c) stimulating platelets. By activating Factors XI and XIII, thrombin generates more thrombin and favors formation of crosslinked fibrin molecules, thereby strengthening the blood clot.

A DTI is an anticoagulant that binds thrombin and blocks thrombin's interaction with its substrates. DTIs may be bivalent (blocking thrombin at the active site and one of the exosites) or univalent (blocking thrombin at the active site). Bivalent DTIs include, without limitation, hirudin and bivalirudin. Univalent DTIs include, without limitation, argatroban, melagatran, ximelagatran, and dabigatran. Dabigatran is sold commercially by Boehringer Ingelheim International GmbH, Ingelheim, Germany under the name PRADAXA®. Dabigatran is an oral direct inhibitor of thrombin (Factor IIa) that is "not permanent," selective and competitive. Dabigatran is licensed in Europe and the USA to reduce the risk of venous thromboembolism (VTE) in orthopedic surgical patients as well as stroke and systemic embolism in patients with non-valvular atrial fibrillation.

In some embodiments, the oral anticoagulant is an inhibitor of Factor Xa and may be referred to as an anti-Factor Xa reagent, a Factor Xa inhibitor, or an xaban. An xaban acts directly upon Factor Xa in the blood clotting cascade (see FIG. 1A). Two non-limiting commercially available inhibitors of Factor Xa are Rivaroxaban (sold under the name of XARELTO® by Bayer Pharma AG, Leverkusen, Germany and Janssen Pharmaceuticals, Inc., Titusville, N.J.) and Apixaban (sold under the name ELIQUIS® by Bristol-Myers Squibb, New York, N.Y. and Pfizer EEIG Sandwich, United Kingdom). Rivaroxaban and Apixaban are licensed in Europe and the USA to reduce the risk of venous thromboembolism (VTE) in orthopedic surgical patients as well as stroke and systemic embolism in patients with non-valvular atrial fibrillation. Rivaroxaban is also approved in the EU for the secondary prevention of acute coronary syndrome. Rivaroxaban can be administered in combination with acetylsalicylic acid (ASA) or with ASA plus clopidogrel or ticlopidine for the prevention of thrombotic events in adult patients with elevated cardiac biomarkers after a coronary event according to the product information provided by Bayer Pharma.

Additional non-limiting inhibitors of Factor Xa include betrixaban (LY517717; Portola Pharmaceuticals), darexaban (YM150; Astellas), edoxaban (Lixiana; DU-176b; Daiichi), TAK-442 (Takeda), and eribaxaban (PD0348292; Pfizer).

In various embodiments, the methods described herein involve the use of a Factor Xa reagent. By "Factor Xa reagent" is meant Factor Xa (FXa) and/or any combination of clotting Factors that include Factor Xa. This Factor Xa reagent may contain other substances for performance and/or stability improvement (including salts, buffers, sugars etc.). Factor Xa reagent is added to a blood component after that blood component has been obtained from the patient. Alternatively, the Factor Xa reagent may be prepared from the Factor X endogenous in the blood component sample by the addition of another reagent such as Russel's Viper venom that activates the Factor X zymogen (precursor of active Factor Xa).

By "clotting measurement" is a measurement of clot formation. This measurement can be taken any time during the formation of a clot including, without limitation, the time of the initial formation of fibrin or the time the clot achieves a certain level of strength. If the clotting assay used to determine the clotting measurement is a thromboelastography (TEG) assay (e.g., performed on the thromboelastograph coagulation analyzer model 5000 platform), the time of the initial formation of fibrin is the "R" time and the time the clot achieves a certain level of strength is the "K" time. If the clotting assay used to determine the clotting measurement is a thromboelastometry (TEM) assay (e.g., performed on the ROTEM platform), then the time of the initial formation of fibrin is the "Reaction Time (RT)" and the time the clot achieves a certain level of strength is the "Clot Formation Time (CFT)". It should be noted that the clotting measurement can be taken on a blood component taken directly from a patient, or a blood component that has been treated with a clotting activator such as kaolin or a clotting inhibitor such as citrate that has been suitably reversed by the addition of calcium.

By "clotting assay" is meant any type of assay that can be used to measure the ability of blood or a blood component to form a clot. Clotting assays including, without limitation, a viscoelastic assay (including a thromboelastography (TEG) assay or a thromboelastometry (TEM) assay), a prothrombin time (PT) assay, an activated partial thromboplastin time (aPTT) assay, and an activated clotting time (ACT) assay.

Figures 2A, 2B, 2C:
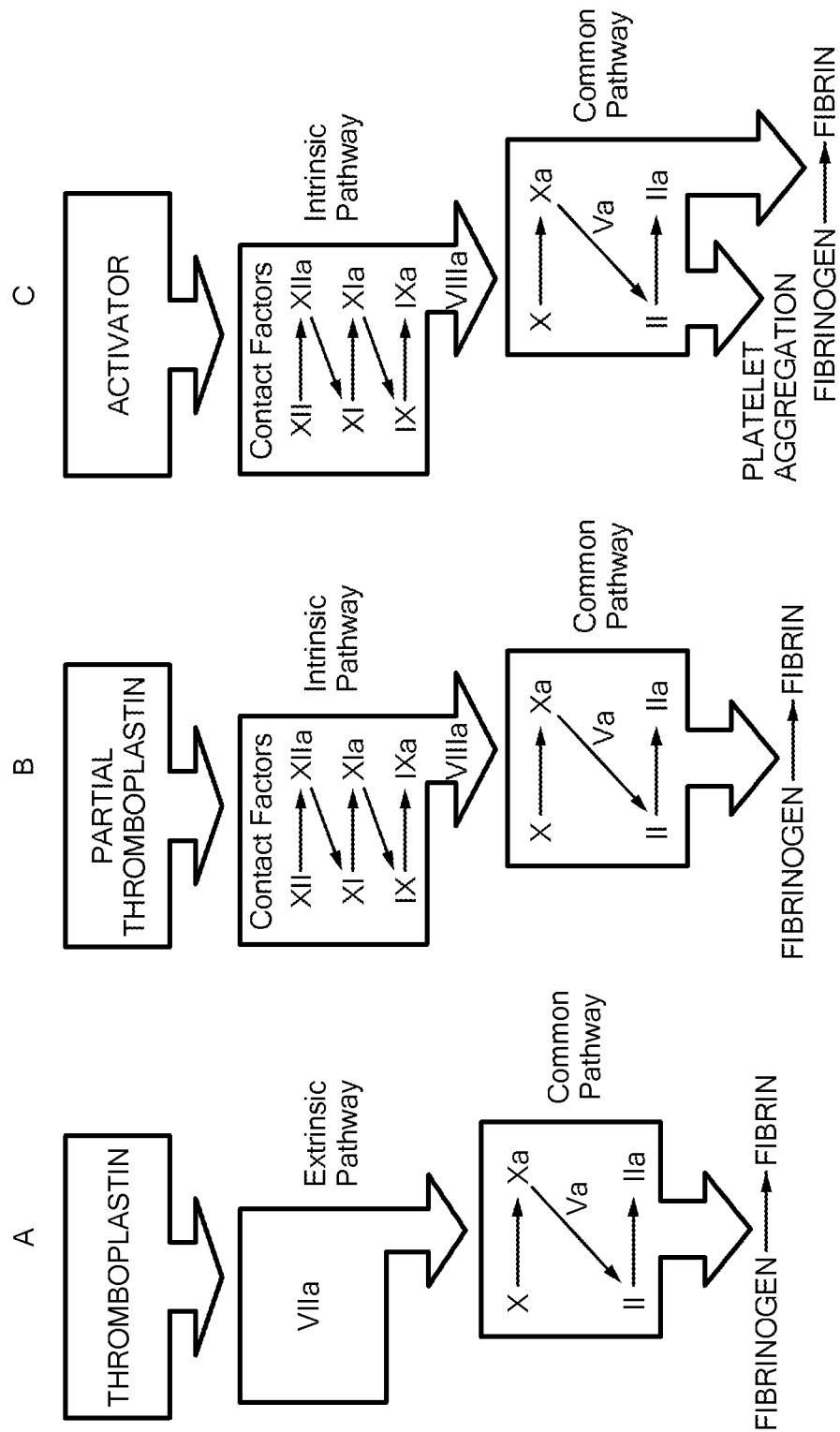
FIGS. 2A-2C are a series of flow charts showing different types of clotting assays that are useful in embodiments of the invention.

In some embodiments, the clotting assay is a prothrombin time (PT) clotting assay. FIG. 2A schematically depicts the prothrombin time (PT) clotting assay. The PT assay is performed by adding a thromboplastin reagent that contains tissue factor (which can be recombinant in origin or derived from an extract of brain, lung, or placenta) and calcium to plasma (or other blood component, which may be citrated, for example) and measuring the clotting time. The prothrombin time (PT) varies with reagent and coagulometer but typically ranges between 10 and 14 second (see Bates and Weitz, Circulation 112: e53-e60, 2005; White et al., "Approach to the bleeding patient", In: Colman R W et al. (eds) *Hemostasis and Thrombosis: Basic Principles and Clinical Practice*. 3rd ed. Philadelphia, Pa.: JB Lippincott Co. 1134-1147, 1994). The PT value may be used as a non-limiting clotting measurement in accordance with the methods described herein. The PT may be abnormal (e.g., may be prolonged) when the blood being tested contains an anticoagulant (e.g., an anticoagulant that was orally administered to the person whose blood is being tested) when the blood being tested is from a patients with a deficiency in a clotting factor (e.g., a deficiency of factors VII, X, and V, prothrombin, or fibrinogen). This test also is abnormal in patients with inhibitors of the fibrinogen-to-fibrin conversion reaction, including high doses of heparin and the presence of fibrin degradation products.

In some embodiments, the clotting assay is the activated partial thromboplastin time (aPTT) clotting assay. FIG. 2B schematically depicts the steps involved in the activated partial thromboplastin time (aPTT) clotting assay. The aPTT assay is also known as the Kaolin Cephalin Clotting Time assay (cephalin is a platelet phospholipid substitute) or a partial thromboplastin time with Kaolin (PTTK) assay. The aPTT is typ performed by first adding a surface activator (e.g., kaolin, celite, ellagic acid, or silica) and diluted phospholipid (e.g., cephalin) to citrated plasma (FIG. 2B). The phospholipid in this assay is called partial thromboplastin because tissue factor is absent. After incubation to allow optimal activation of contact factors (e.g., factor XII, factor XI, prekallikrein, and high-molecular-weight kininogen) and the generation of Factor IXa, calcium is then added, and the clotting time is measured. Thus, the APTT time is the time taken from the addition of calcium to the formation of a fibrin clot. Although the clotting time varies according to the reagents (e.g., type of surface activator) and coagulometer used, the aPTT typically ranges between 22 and 40 seconds (see Bates and Weitz, supra). The aPTT time may be used as a non-limiting clotting measurement in accordance with the methods described herein. The aPTT may be abnormal (e.g., may be prolonged) when the blood being tested contains an anticoagulant (e.g., an anticoagulant that was orally administered to the person whose blood is being tested). The aPTT may be prolonged with deficiencies of contact factors; factors IX, VIII, X, or V; prothrombin; or fibrinogen. Specific factor inhibitors, as well as nonspecific inhibitors, may also prolong the aPTT. Fibrin degradation products and anticoagulants (e.g., heparin, direct thrombin inhibitors, or warfarin) also prolong the aPTT.

In some embodiments, the clotting assay is an activated clotting time (ACT) assay. FIG. 2C schematically depicts the steps involved in the activated clotting time (ACT) assay. Typically, whole blood is collected into a tube or cartridge containing a coagulation activator (e.g., celite, kaolin, or glass particles) and a magnetic stir bar. Once thrombin is generated, it induces both platelet aggregation and fibrin formation, and the time taken for the blood to clot is then measured (see also Van Cott and Laposata, "Coagulation". In: Jacobs D S et al. (eds), *The Laboratory Test Handbook*, 5th ed. Cleveland, Ohio: Lexi-Comp; 2001:327-358, 2001). The reference value for the ACT ranges between 70 and 180 seconds. The ACT value may be used as a non-limiting clotting measurement in accordance with the methods described herein. The ACT time is prolonged when the blood being tested contains an anticoagulant (e.g., an anticoagulant that was orally administered to the person whose blood is being tested).

In some embodiments, the clotting assay is a viscoelastic assay. By "viscoelastic analysis" is meant any analysis method that measures the characteristics of elastic solid (e.g., fibrin solids) and fluids. In other words, viscoelastic analysis allows the study of properties of a viscous fluid, such as blood, plasma, or a blood sample.

In some embodiments, the viscoelastic analysis is performed under conditions that mimic the conditions in vivo that result in haemostasis. For example, the condition may include a temperature that mimics a body temperature (e.g., a temperature of 37° C.). The condition may also include clot formation and dissolution at flow rates that mimic those found in blood vessels.

In some embodiments, viscoelastic analysis of a blood sample may include subjecting the blood sample to analysis on a hemostasis analyzer instrument. One non-limiting viscoelastic analysis method is the thromboelastography ("TEG") assay. Thus in some embodiments, the viscoelastic analysis includes subjecting a blood sample to analysis using thromboelastography (TEG), which was first described by Helmut Hartert in Germany in the 1940's.

Various devices that perform thromboelastography, and methods for using it are described in U.S. Pat. Nos. 5,223,227; 6,225,126; 6,537,819; 7,182,913; 6,613,573; 6,787,363; 7,179,652; 7,732,213, 8,008,086; 7,754,489; 7,939,329; 8,076,144; 6,797,419; 6,890,299; 7,524,670; 7,811,792; 20070092405; 20070059840; U.S. Pat. No. 8,421,458; US 20120301967; and U.S. Pat. No. 7,261,861, the entire disclosures of each of which are hereby expressly incorporated herein by reference.

Thromboelastography (TE) monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood. In essence, the clot is the elementary machine of hemostasis. Haemostasis instruments that measure haemostasis are able to measure the ability of the clot to perform mechanical work throughout its structural development. These haemostasis analyzers measure continuously all phases of patient hemostasis as a net product of whole blood components in a non-isolated, or static fashion from the time of test initiation until initial fibrin formation, through clot rate strengthening and ultimately clot strength through clot lysis.

In some embodiments, the viscoelastic analysis and/or the haemostais analyzer comprises a container which is in contact with the blood.

As used herein, by "container" is meant a rigid surface (e.g., a solid surface), a portion of which contacts a portion of a blood sample placed into the container at any point during the viscoelastic analysis. The portion of the container that contact the portion of blood sample may also be referred to as the "interior" of the container. Note that the phase "into the container" does not mean that the container has a bottom surface which is in contact with the portion of the blood sample. Rather, the container can be a ring-shaped structure, where the inside of the ring is the interior of the container, meaning that the inside of the ring is the portion of the ring-shaped container that contacts a portion of the blood sample. A blood sample can flow into the container and be held there, for example, by vacuum pressure or surface tension.

Still additional types of containers that are included in this definition are those present on plates and cassettes (e.g., a microfluidic cassette), where the plate or cassette has multiple channels, reservoirs, tunnels, and rings therein. Each of the contiguous channels (comprising, for example, a channel, a reservoir, and a ring) is a container, as the term is used herein. Hence, there may be multiple containers on one cassette. U.S. Pat. No. 7,261,861 (incorporated herein by reference) describes such a cassette with multiple channels or containers. Any of the surfaces in any of the channels or tunnels of the cassette may be an interior of the container if that surface comes into contact with any portion of the blood sample, at any time during the viscoelastic analysis.

One non-limiting haemostasis analyzer instrument is described in U.S. Pat. No. 7,261,861; US Patent Publication No. US US20070092405; and US Patent Publication No. US20070059840.

Another non-limiting haemostasis analyzer instrument that performs viscoelastic analysis using thromboelastography is the TEG® thromboelastograph hemostasis analyzer system sold commercially by Haemonetics, Corp. (Braintree, Mass.).

Thus, the TEG assay may be performed using the TEG thromboelastograph hemostasis analyzer system that measures the mechanical strength of an evolving blood clot. To run the assay, the blood sample is placed into a container (e.g., a cup or a cuvette), and a plastic pin goes into the center of the container. Contact with the interior walls of the container (or addition of a clot activator to the container) initiates clot formation. The TEG thromboelastograph hemostasis analyzer then rotates the container in an oscillating fashion, approximately 4.45 degrees to 4.75 degrees, every 10 seconds, to imitate sluggish venous flow and activate coagulation. As fibrin and platelet aggregates form, they connect the inside of the container with the plastic pin, transferring the energy used to move the container in the pin. A torsion wire connected to the pin measures the strength of the clot over time, with the magnitude of the output directly proportional to the strength of the clot. As the strength of the clot increases over time, a classic TEG tracing curve develops (See FIG. 3A). The curve depicted is from a normal human patient who is known to be not taking any anticoagulants.

Figure 3A:
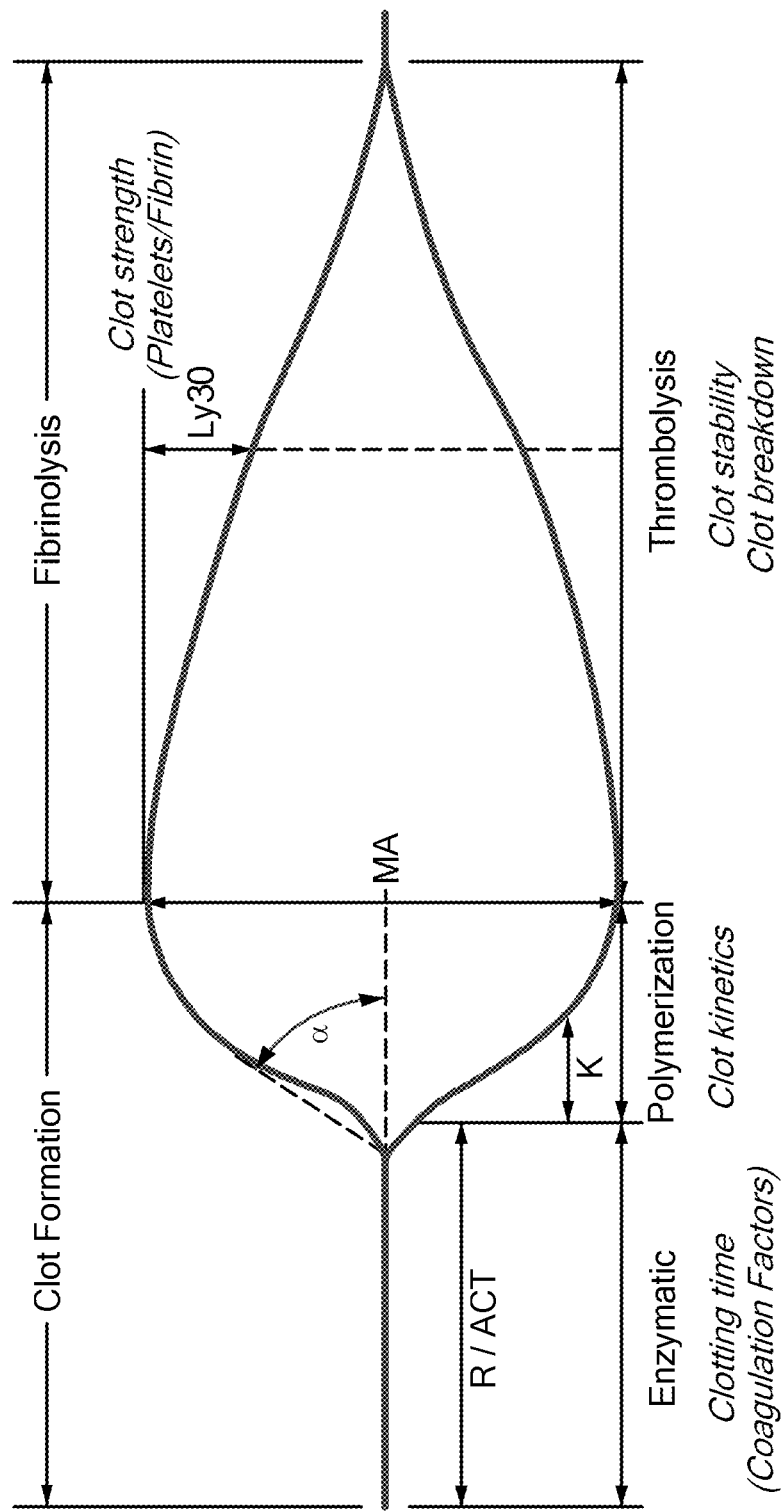
FIG. 3A is schematic diagram showing a TEG tracing measured throughout the clot's lifespan of a blood component sample taken from a normal human. The R (reaction time) and ACT (activated clotting time) is the time of formation of the fibrin strand polymers, K (coagulation time) is a measurement of time until a certain clot strength is attained, a (alpha angle) is the slope of a line drawn from R tangent to the curve, and MA (maximum amplitude, measured in mm) is the strength of the clot. The LY30 is a percent lysis measurement which is measured until 30 minutes after MA is defined.

The rotational movement of the pin is converted by a transducer to an electrical signal, which can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the skills of one having ordinary skill in the art. As shown in FIG. 3A, the resulting hemostasis profile (i.e., a TEG tracing curve) is a measure of the time it takes for the first fibrin strand to be formed, the kinetics of clot formation, the strength of the clot (measured in millimeters (mm) and converted to shear elasticity units of dyn/cm2) and dissolution of clot. See also Donahue et al., *J. Veterinary Emergency and Critical Care:* 15(1): 9-16. (March 2005), herein incorporated by reference.

The descriptions for several of these measured parameters, any of which can be used as a clotting measurement in accordance with the methods described here, are as follows:

R is the period of time of latency from the time that the blood was placed in the thromboelastography analyzer until the initial fibrin formation. This typically takes about 30 second to about 10 minutes; however the R range will vary based on the particular TEG assay performed (e.g., type of blood component being tested, whether the blood component is citrated or not, etc.). For example, in Example 1 below, the normal R range (i.e., from a citrated blood component in the presence of Kaolin) is between about 5 minutes to about 10 minutes. For patients in a hypocoagulable state (i.e., a state of decreased coagulability of blood), the R number is longer which indicates slower clot formation, while in a hypercoagulable state (i.e., a state of increased coagulability of blood), the R number is shorter. In the methods described herein, the R value (in minutes or seconds) that can be used as a non-limiting clotting measurement. Note that in FIG. 3A, the R value is labeled as "R/ACT" because when the TEG assay is performed with a kaolin-Tissue Factor treated blood component, the R value is sometimes referred to as the ACT value (the activated clotting time value) in reference to the older activated clotting time (ACT) assay described above and in FIG. 2C.

K value (measured in minutes) is the time from the end of R until the clot reaches 20 mm and this K value represents the speed of clot formation. This K value is typically about 0 to about 4 minutes (i.e., after the end of R). In a hypocoagulable state, the K number is longer, while in a hypercoagulable state, the K number is shorter. This K value may be used as a non-limiting clotting measurement in accordance with the methods described herein.

α angle (or simply a) measures the rapidity of fibrin build-up and cross-linking (clot strengthening). It is angle between the line formed from the split point tangent to the curve and the horizontal axis. This angle is typically about 47° to 74°. In a hypocoagulable state, the α degree is lower, while in a hypercoagulable state, the α degree is higher. This a angle value may be used as a non-limiting clotting measurement in accordance with the methods described herein.

MA or Maximum Amplitude in mm, is a direct function of the maximum dynamic properties of fibrin and platelet bonding and represents the ultimate strength of the fibrin-platelet clot. This number is typically from about 54 mm to about 72 mm, and the MA occurs typically between about 15 to about 35 minutes after the start of the viscoelastic assay. Note that if the blood sample tested has a reduced platelet function, this MA represents the strength of the clot based on fibrin only. Decreases in MA may reflect a hypocoagulable state (e.g., with platelet dysfunction or thrombocytopenia), whereas an increased MA (e.g., coupled with decreased R) may be suggestive of a hypercoagulable state. This MA value may be used as a non-limiting clotting measurement in accordance with the methods described herein.

LY30 is a measurement of tracing area-reduction 30 minutes after MA. The LY30 is a percentage decrease in amplitude 30 minutes after the MA. This number is typically 0% to about 8%—a non-limiting clotting measurement in accordance with the methods described herein. When no fibrinolysis occurs, the amplitude value at the MA tracing stays constant or may decrease slightly due to clot retraction. However, as fibrinolysis occurs (e.g., in a hypocoagulable state), the curve of the TEG tracing starts to decay. The resultant loss in potential area-under-the-curve in the 30 minutes following Maximum Amplitude in the TEG assay is called the LY30 (see FIG. 3A). LY30, the percentage of lysis 30 minutes after the maximum amplitude point (expressed as a percentage of the clot lysed) indicates the rate of clot lysis.

It should be noted that modifications of the TEG assay can be performed, such as the modified TEG assays described below in the Examples section. For example, in Example 1 below, the RapidTEG (rTEG) test incorporates both tissue factor and kaolin to generate the conventional kaolin parameters as well as the TEG-ACT parameter, which is measured in seconds. The TEG-ACT is equivalent to the Activated Clotting Time (see Chavez J J., Anesth. Analg. 99: 1290-1294, 2004). A prolonged TEG-ACT time (as compared to the ACT time from a normal blood component) indicates slower clot formation.

Figure 3B:
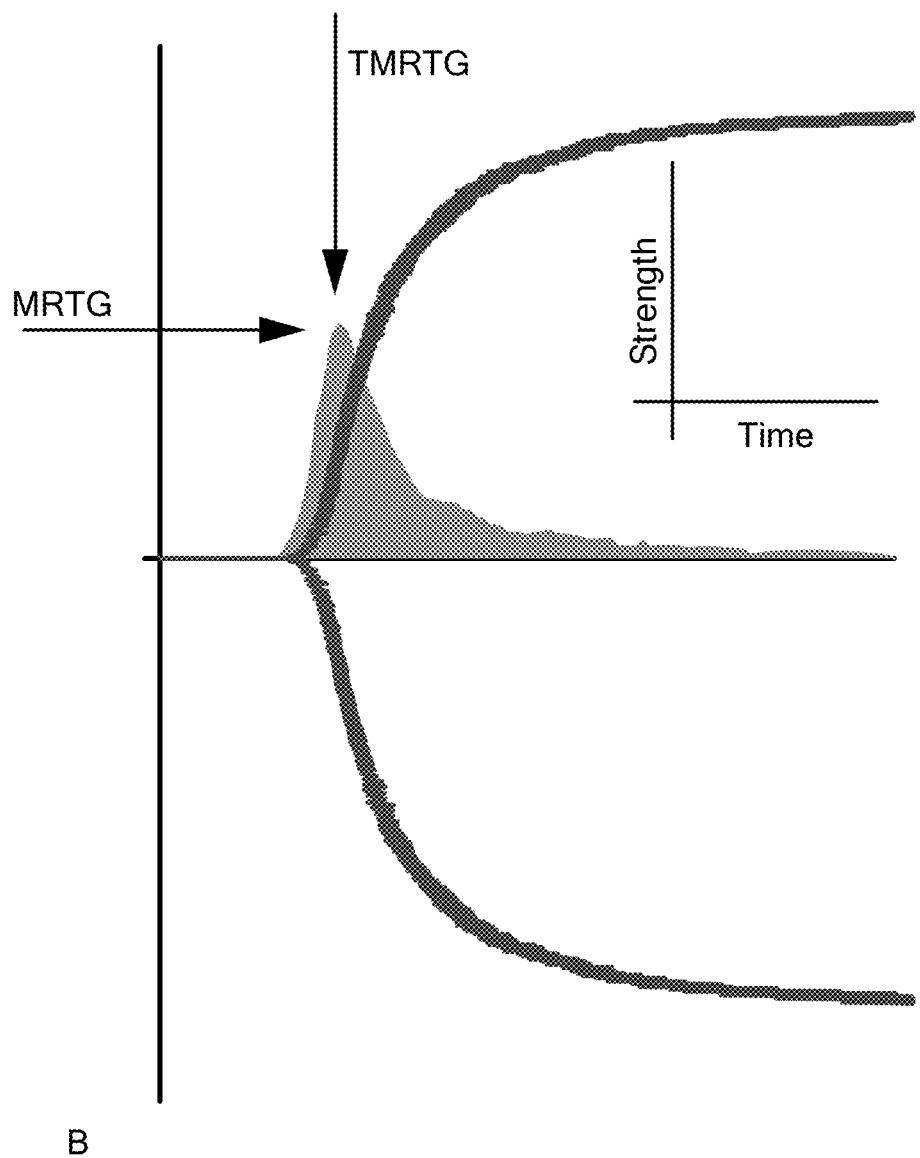
FIG. 3B is a schematic diagram representing a Thrombus Generation Curve (V-Curve in green) overlaying a TEG tracing. The V-curve is plotted from the first derivative of changes in clot resistance expressed as a change in clot strength per unit of time (dynes/cm2/s), representing the maximum velocity of clot formation. MRTG stands for Maximum Rate of Thrombus Generation; and TMRTG stands for Time to Maximum Rate of Thrombus Generation.

Finally, it should be noted that velocity curves can be derived from the kaolin TEG tests and RapidTEG tests (incorporating both kaolin and tissue factor). These velocity curves can be plotted using TEG software. These curves represent the speed of clot propagation (MRTG, Maximum Rate of Thrombus Generation; and TMRTG, Time to Maximum Rate of Thrombus Generation) (see FIG. 3B). Either or both of the MRTG or the TMRTG may be used as a non-limiting clotting measurement in accordance with the methods described herein.

Viscoelastic measurements of coagulation provided by devices such as TEG are increasingly being employed to assess trauma patients who arrive in shock secondary to massive bleeding as well as for acute care of surgical patients with bleeding diatheses. TEG is widely used as a management tool for cardiac surgery and transplant patients and provides information to guide administration of blood products (see Holcolmb J. B. et al., Ann. Surg. 256: 476-486, 2012). TEG is able to detect both low molecular weight and unfractionated heparin and, with the use of a heparinase cup, can illustrate whether the effects of these agents have been completely reversed. Furthermore, the TEG PlateletMapping Assay is used to quantify the response to antiplatelet therapies including clopidogrel and aspirin that can be used in combination with an oral anticoagulant. TEG assays using ecarin have been employed to monitor recombinant hirudin as well as bivalirudin during cardiac surgery (Koster, A. et al., J. Card. Surg. 23: 321-323, 2008; Choi, T. S. et al., Am. J. Clin. Path. 125: 290-295, 2006).

Figure 4:
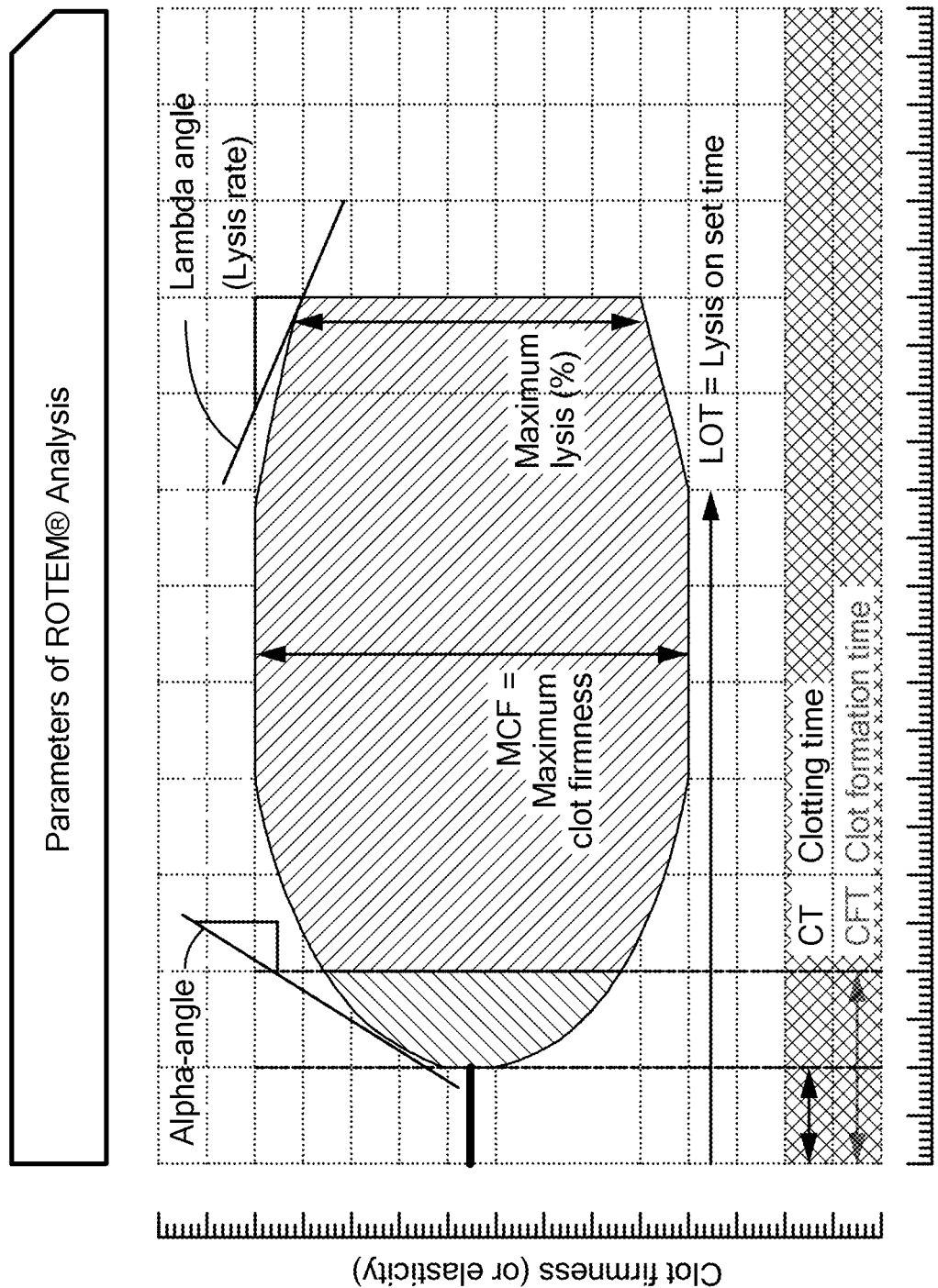
FIG. 4 is schematic diagram showing a TEMogram tracing. CT indicates clotting time, CFT indicates clot formation time, alpha is the alpha-angle, lambda-angle is the lysis rate, MCF is the maximum clot firmness, and ML is maximum lysis.

Another viscoelastic hemostasis assay that can be used is the thromboelastometry ("TEM") assay. This TEM assay may be performed using the ROTEM Thromboelastometry Coagulation Analyzer (TEM International GmbH, Munich, Germany), the use of which is well known (See, e.g., Sorensen, B., et al., J. Thromb. Haemost., 2003. 1(3): p. 551-8. Ingerslev, J., et al., Haemophilia, 2003. 9(4): p. 348-52. Fenger-Eriksen, C., et al. Br J Anaesth, 2005. 94(3): p. 324-9]. In the ROTEM analyzer, the blood sample is placed into a container (also called a cuvette or cup) and a cylindrical pin is immersed. Between pin and the interior wall of the container there is a gap of 1 mm which is bridged by the blood. The pin is rotated by a spring to the right and the left. As long as the blood is liquid (i.e., unclotted), the movement is unrestricted. However, when the blood starts clotting, the clot increasingly restricts the rotation of the pin with rising clot firmness. The pin is connected to an optical detector. This kinetic is detected mechanically and calculated by an integrated computer to the typical tracing curves (TEMogram) and numerical parameters (see FIG. 4).

Figure 5:
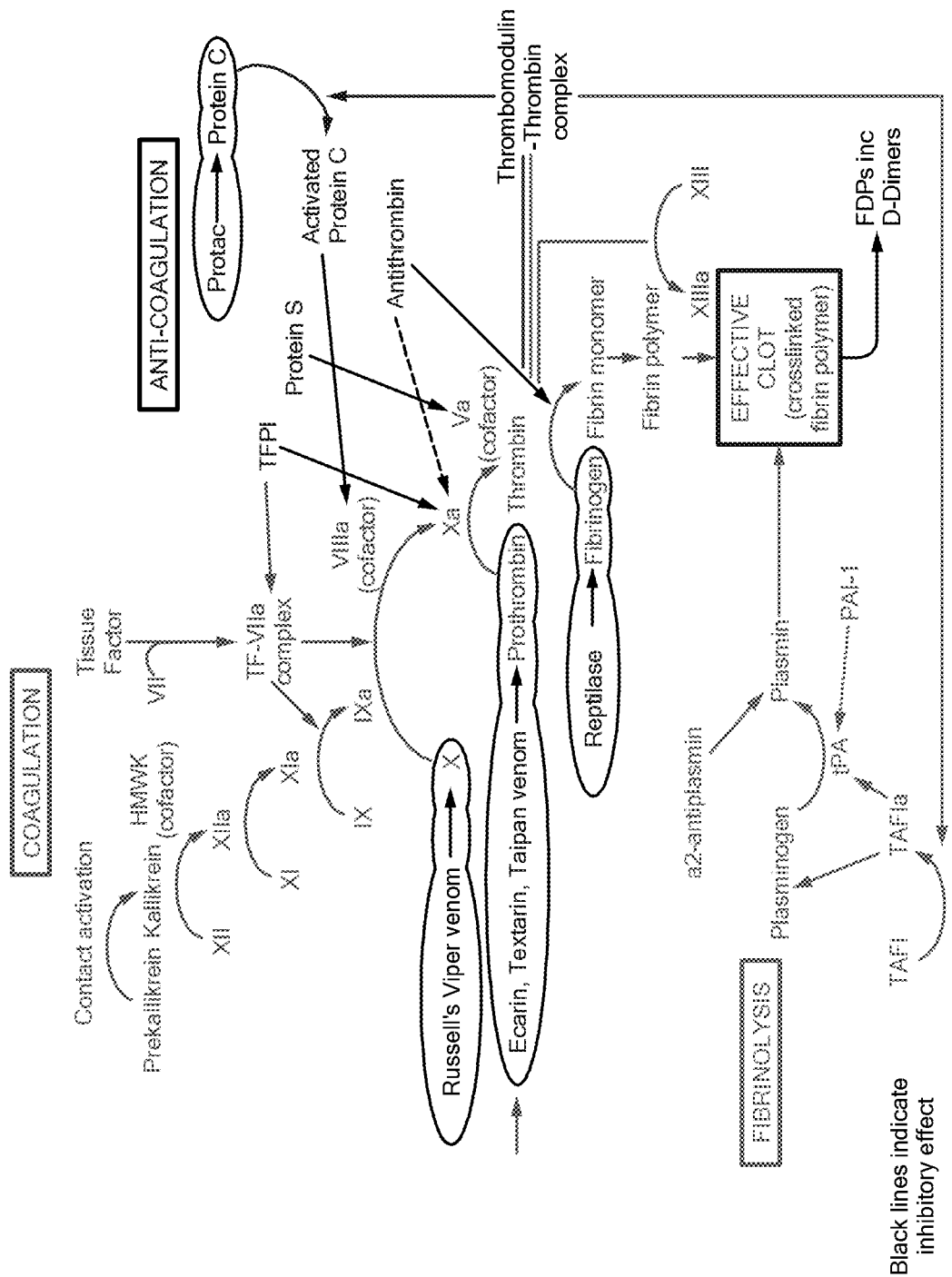
FIG. 5 is a schematic diagram of the clotting cascade showing the stages at which various ecarin reagents (which includes ecarin and similar enzymes) interfere with the cascade.

In the ROTEM Thromboelastometry Coagulation Analyzer, the movement of the pin can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile (called a TEMogram). Such a configuration of the computer is well within the skills of one having ordinary skill in the art. As shown in FIG. 5, the resulting hemostasis profile (i.e., a TEM tracing curve) is a measure of the time it takes for the first fibrin strand to be formed, the kinetics of clot formation, the strength of the clot (measured in millimeters (mm) and converted to shear elasticity units of dyn/cm2) and dissolution of clot. The descriptions for several of these measured parameters, any of which can be used as a clotting measurement in accordance with the methods described here, are as follows:

CT (clotting time) is the period of time of latency from the time that the blood was placed in the ROTEM analyzer until the clot begins to form. This CT time may be used as a non-limiting clotting measurement in accordance with the methods described herein.

CFT (Clot formation time): the time from CT until a clot firmness of 20 mm point has been reached. This CFT time may be used as a non-limiting clotting measurement in accordance with the methods described herein.

alpha-angle: The alpha angle is the angle of tangent at 2 mm amplitude. This alpha angle may be used as a non-limiting clotting measurement in accordance with the methods described herein.

MCF (Maximum clot firmness): MCF is the greatest vertical amplitude of the trace. MCF reflects the absolute strength of the fibrin and platelet clot. The MCF value may be used as a non-limiting clotting measurement in accordance with the methods described herein.

A10 (or A5, A15 or A20 value). This A10 value describes the clot firmness (or amplitude) obtained after 10 (or 5 or 15 or 20) minutes and provide a forecast on the expected MCF value at an early stage. Any of these A values (e.g., A10) may be used as a non-limiting clotting measurement in accordance with the methods described herein.

LI30 (Lysis Index after 30 minutes). The LI30 value is the percentage of remaining clot stability in relation to the MCF value at 30 min after CT. This LI30 value may be used as a non-limiting clotting measurement in accordance with the methods described herein. When no fibrinolysis occurs, the amplitude value at the MCF on a TEM tracing stays constant or may decrease slightly due to clot retraction. However, as fibrinolysis occurs (e.g., in a hypocoagulable state), the curve of the TEM tracing starts to decay. LI30 corresponds to the LY30 value from a TEG tracing.

ML (Maximum Lysis). The ML parameter describes the percentage of lost clot stability (relative to MCF, in %) viewed at any selected time point or when the test has been stopped. This ML value may be used as a non-limiting clotting measurement in accordance with the methods described herein.

Thus, parameters of interest in TEG or TEM assays, each of which can be used as a clotting measurement in accordance with the methods described herein, include the maximum strength of the clot which is a reflection of clot strength. This is the MA value in the TEG assay, and the MCF value in the TEM assay. The reaction time (R) in TEG (measured in seconds or minutes) and clotting time (CT) in TEM is the time until there is first evidence of clot; clot kinetics (K, measured in minutes) is a parameter in the TEG test indicating the achievement of clot firmness; and a in TEG or alpha-angle in TEM is an angular measurement from a tangent line drawn to the curve of the TEG tracing or TEM tracing starting from the point of clot reaction time that is reflective of the kinetics of clot development. (See Trapani, L. M. Thromboelastography: Current Applications, Future Directions", Open Journal of Anesthesiology 3(1): Article ID: 27628, 5 pages (2013); and Kroll, M. H., "Thromboelastography: *Theory and Practice in Measuring Hemostasis,*" *Clinical Laboratory News: Thromboelastography* 36(12), December 2010; instruction manuals for the TEG instrument (available from Haemonetics, Corp.), and the instruction manual for the ROTEM instrument (available from TEM International GmbH), all of which documents are herein incorporated by reference in their entireties.

In some embodiments, the parameters (and hence the clotting measurements) are recorded by observation of different excitation levels of the sample as coagulation occurs. For example, where the container is a microfluidic cassette or a particular channel in the cassette, the blood component sample may be excited at a resonant frequency and its behavior observed by an electromagnetic or light source as coagulation occurs. In other embodiments the blood component sample's clotting measurement may be observed for changes with a light source without exciting the sample.

Because a single cassette may have multiple containers (e.g., different channels in the cassette), the different samples (e.g., portions of the blood component from the patient) are easily directly comparable one another. For example, one channel may be untreated, one channel may be treated with the Factor Xa reagent, and one channel may be treated with the ecarin reagent. In another example, blood components from different individuals can be measured in the different channels, and the results from the different individuals obtained simultaneously from a single cassette.

By "therapeutically relevant amount" is meant an amount of an anticoagulant in the blood component being tested that is within the therapeutically effective concentration range for the anticoagulant. The therapeutically relevant amount will differ for each anticoagulant, and is affected by the bioavailability of the anticoagulant and also the half-life of the anticoagulant following ingestion by the patient. For example, dabigatran has a half-life of 12-17 hours which is lengthened in patients with renal dysfunction (Boehringer Ingelheim International G. Pradaxa (dabigatran etexilate) product information). Apixaban and rivaroxaban have shorter half-lives than dabigatran. However, apixaban has also an increased half-life of up to 44% in patients with severe renal impairment compared to healthy volunteers (see Dager et al., Crit. Care Med. 41: e42-46, 2013). The anticoagulant effect of apixaban or rivaroxaban can be expected to persist for at least 10-30 hours after the last dose, i.e. for about two half-lives. Generally, however, the therapeutically relevant amount of an anticoagulant is between about 75 ng/ml to about 500 ng/ml in the blood (or blood component). For example, for apixaban, a therapeutically relevant amount is between about 275 to about 775 ng/ml, or between about 300 to about 650 ng/ml, or between about 400 to about 600 ng/ml, or at about 500 ng/ml in the blood or blood component. For rivaroxaban, a therapeutically relevant amount is between about 40 to about 350 ng/ml, or between about 55 to about 250 ng/ml, or between about 70 to about 150 ng/ml, or at about 89 ng/ml in the blood or blood component. For dabigatran, a therapeutically relevant amount is between about 100 to about 350 ng/ml, or between about 150 to about 300 ng/ml, or between about 175 to about 250 ng/ml, or at about 200 ng/ml in the blood or blood component.

In another aspect, the invention provides a method for classifying an anticoagulant at a therapeutically relevant amount or higher than a therapeutically relevant amount in a blood component from a patient, the method comprising: (a) identifying the presence of an anticoagulant in the blood component, comprising the steps of (i) subjecting a control blood component sample (known not to contain anticoagulant) to a clotting assay in the presence of a Factor Xa reagent to obtain a control clotting measurement; and (ii) subjecting a blood component sample from the same donor (unknown regarding presence of anticoagulant) to the clotting assay in presence of the Factor Xa reagent to obtain the clotting measurement of the second blood component, wherein the clotting measurement of the second sample that is greater than the clotting measurement of the first sample indicates the presence of the anticoagulant at a therapeutic level in the blood component and wherein the clotting measurement from the second sample that is less than or equal to the clotting measurement of the first sample indicates the absence of the anticoagulant at a therapeutically relevant amount in the blood component and (b) classifying the anticoagulant in the blood component, comprising the steps of: (i) subjecting a second portion of the blood component (known to contain anticoagulant according to the steps described in (a) to a clotting assay in the presence of an ecarin reagent to obtain the clotting measurement of the second portion; and (ii) subjecting a second portion of the blood (known not to contain anticoagulant) to the clotting assay in the presence of the ecarin reagent to obtain the clotting measurement of this portion, wherein the clotting measurement of the portion (known to contain anticoagulant) that is greater than the clotting measurement of the portion (known not to contain anticoagulant) identifies the anticoagulant as a direct thrombin inhibitor (DTI) and wherein the clotting measurement of the portion (known to contain anticoagulant) that is less than or equal to the clotting measurement of the portion (known not to contain anticoagulant) identifies the anticoagulant as an anti-Factor Xa anticoagulant.

In yet another aspect, the invention provides a method for classifying an anticoagulant at a therapeutically relevant amount or higher than a therapeutically relevant amount in a patient suspected of having an anticoagulant, the method comprising: (a) identifying the presence of an anticoagulant in a blood component from the patient, comprising the steps of (i) subjecting a control sample of a control blood component, the control blood component known not to contain the anticoagulant, to a clotting assay in the presence of a Factor Xa reagent to obtain a Factor Xa clotting measurement of the control sample; and (ii) subjecting a patient sample of a blood component from the patient to the clotting assay in the presence of the Factor Xa reagent to obtain the Factor Xa clotting measurement of the patient sample, wherein the Factor Xa clotting measurement of the patient sample greater than the Factor Xa clotting measurement of the control sample indicates the presence of the anticoagulant at a therapeutically relevant amount in the patient and wherein the Factor Xa clotting measurement of the second sample less than or equal to the Factor Xa clotting measurement of the control sample indicates the absence of the anticoagulant at a therapeutically relevant amount in the patient; and (b) classifying the anticoagulant in the patient, comprising the steps of: (i) subjecting a second control sample of the control blood component to the clotting assay in the presence of an ecarin reagent to obtain the ecarin clotting measurement of the second control sample; and (ii) subjecting a second patient sample of the blood component from the patient to the clotting assay in the presence of the ecarin reagent to obtain the ecarin clotting measurement of the second patient sample, wherein the ecarin clotting measurement of the second patient sample greater than the ecarin clotting measurement of the second control sample identifies the anticoagulant as a direct thrombin inhibitor (DTI) and wherein the ecarin clotting measurement of the second patient sample that is less than or equal to the ecarin clotting measurement of the second control sample identifies the anticoagulant as an anti-Factor Xa reagent.

In another aspect, the invention provides a method for classifying an anticoagulant at a therapeutically relevant amount or higher than a therapeutically relevant amount in a patient suspected of having an anticoagulant, the method comprising: (a) subjecting a first patient sample of a blood component from the patient to a clotting assay in the presence of a Factor Xa reagent to obtain a Factor Xa clotting measurement of the patient blood component, wherein the Factor Xa clotting measurement of the patient blood component greater than a Factor Xa clotting measurement of a control blood sample of a control blood component known to lack the anticoagulant identifies the presence of the anticoagulant at a therapeutically relevant amount in the patient; and (b) subjecting a second patient sample of the blood component from the patient to the clotting assay in the presence of an ecarin reagent to obtain the ecarin clotting measurement of the second patient sample; wherein the ecarin clotting measurement of the second patient sample greater than an ecarin clotting measurement of a control sample of the control blood component identifies the anticoagulant as a direct thrombin inhibitor (DTI) and wherein the ecarin clotting measurement of the second patient sample less than or equal to the ecarin clotting measurement of the control sample identifies the anticoagulant as an anti-Factor Xa reagent.

In another aspect, the invention provides a method for identifying and classifying an anticoagulant at a therapeutically relevant amount or higher in a patient suspected of having an anticoagulant (or known to have an anticoagulant), the method comprising subjecting a first patient sample of a blood component from the patient to a clotting assay in the presence of an ecarin reagent to obtain ecarin clotting measurement of the patient blood component, wherein the ecarin clotting measurement of the patient blood component greater than an ecarin clotting measurement of a control blood sample of a control blood component known to lack the anticoagulant identifies the presence of the anticoagulant at a therapeutically relevant amount in the patient and classifies it as a DTI. In some embodiments, the method further includes subjecting a second patient sample of the blood component from a patient known or suspected to contain anticoagulant to the clotting assay in the presence of a FXa reagent to obtain the FXa clotting measurement of the second patient sample; wherein the FXa clotting measurement of the second patient sample greater than the FXa clotting measurement of a control sample of the control blood component known to lack the anticoagulant identifies the presence of an anticoagulant at a therapeutically relevant amount and classifies it as a FXa inhibitor and wherein the FXa clotting measurement of the second patient sample less than or equal to the FXa clotting measurement of the control sample indicates lack of any anticoagulant.

In some embodiments, the Factor Xa clotting measurement of the patient sample that is at least 1.25 times greater than the Factor Xa clotting measurement of the control sample identifies the presence of the anticoagulant at a therapeutically relevant amount in the patient. In some embodiments, the Factor Xa clotting measurement of the patient sample that is at least 1.5 times, or at least 1.75 times, or at least 2.0 times, or at least 2.25 times greater than the Factor Xa clotting measurement of the control sample identifies the presence of the anticoagulant at a therapeutically relevant amount in the patient.

In some embodiments, the ecarin clotting measurement of the patient sample that is at least 1.25 times greater than the ecarin clotting measurement of the control sample identifies the anticoagulant as a direct thrombin inhibitor (DTI). In some embodiments, the ecarin clotting measurement of the patient sample that is at least 1.5 times, or at least 1.75 times, or at least 2.0 times, or at least 2.25 times greater than the ecarin clotting measurement of the control sample identifies the anticoagulant as a direct thrombin inhibitor.

By "ecarin reagent" is meant a molecule that activates a prothrombin zymogen (precursor of active thrombin) and produces an activated form with thrombin-like enzymatic activity. In some embodiments, an ecarin reagent also includes enzymes similar to ecarin. Some non-limiting ecarin reagents are shown in FIG. 5. In some embodiments, the ecarin reagent activates the prothrombin zymogen (precursor of active thrombin) and is derived from the venom of the saw-scaled viper, *Echis carinatus*. In some embodiments, the ecarin reagent is textarin.

Figure 6:
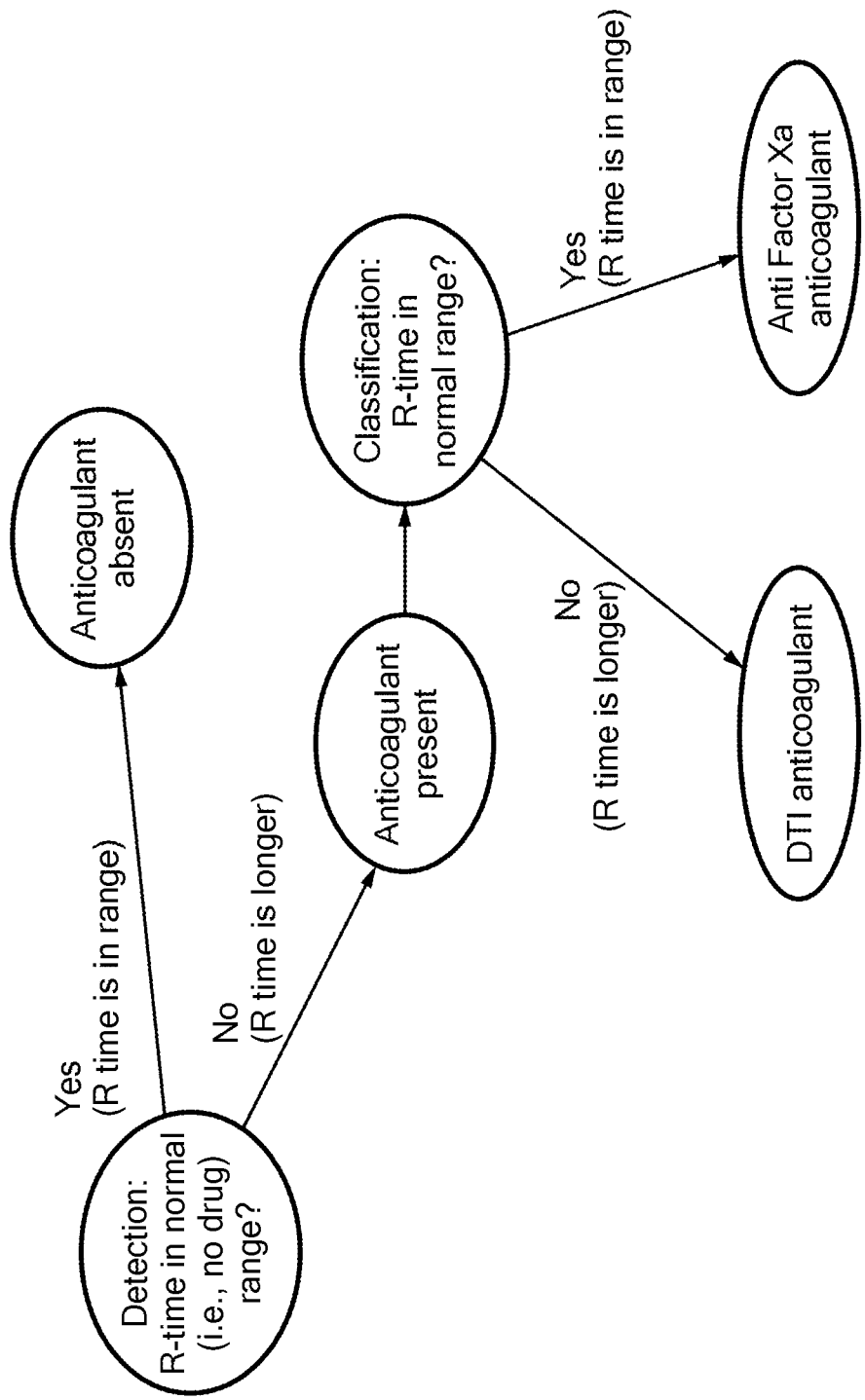
FIG. 6 is a schematic diagram of a decision tree showing the steps involved in a non-limiting aspect of the invention. A blood component taken from a patient suspected of being on an anticoagulant is first subjected to a detection step (to see if there is an anticoagulant in the test blood component) and then subjected to a classification step to determine if the anticoagulant is a DTI or an anti-Factor Xa anticoagulant.

FIG. 6 schematically diagrams the decision tree involved in this non-limiting aspect of the invention. As shown in FIG. 6, step (a) of the above-described method may be referred to as the "detection" step. Using a clotting assay in the presence of the Factor Xa reagent, if the clotting measurement (the "R-time" in FIG. 6) of the tested blood component is within the normal range (where the normal range is based on a blood component from a donor known not to be taking an anticoagulant), the patient from whom the tested blood component was obtained is identified as not being on an anticoagulant (i.e., the patient was not being administered an anticoagulant prior to the test blood component being obtained). If, however, the clotting measurement (the "R-time" in FIG. 6) of the tested blood component is not within the normal range (e.g., has a R-time longer than the normal range), then patient from whom the tested blood component was obtained is identified as being on an anticoagulant. Step (b) of the above-described method may be referred to as the "classification" step (see FIG. 6). Once the test blood component is identified as being obtained from a patient on an anticoagulant (i.e., a patient being administered an anticoagulant), using an ecarin reagent in a clotting assay, the anticoagulant can be identified as being either a DTI or an anti-Factor Xa anticoagulant depending upon whether or not the clotting measurement is within the ecarin normal range. As shown in FIG. 6, if the R time in a clotting assay using ecarin is within the normal range (i.e., the range of R times in the presence of ecarin of blood component from a healthy donors known not to be on an anticoagulant), then the anticoagulant in the patient is identified as being an Factor Xa inhibitor. However, if the R time in a clotting assay using ecarin is longer than (i.e., outside of) the normal range (i.e., the range of R times in the presence of ecarin of blood component from donors known not to be on an anticoagulant), then the anticoagulant in the patient is identified as being a DTI inhibitor.

In some embodiments, once the patient has been identified as patient being administered an anticoagulant, if desired, the patient can be treated with a reversal agent (e.g., in a therapeutically relevant amount). For example, if the patient is identified as having a dabigatran anticoagulant (a DTI anticoagulant), a non-limiting reversal agent that can be administered to the patient to reverse the anticoagulant effect of the dabigatran is Idarucizumab (Boehringer Ingelheim). Similarly, if the patient is identified as having a Factor Xa inhibitor anticoagulant, a non-limiting reversal agent that can be administered to the patient to reverse the anticoagulant effect of the Factor Xa inhibitor is andexanet alfa (Portola Pharmaceuticals). Another non-limiting reversal agent that can be administered to the patient to reverse the anticoagulant effect of a DTI or a Factor Xa inhibitor anticoagulant is prothrombin complex concentrates (PCC) (for example, the PCC-4 factor sold under the name KCENTRA® (registration owned by CSL Behring GmbH), OCTAPLEX® (registration owned by Octapharma AG AKTIENGESELLSCHAFT), and Beriplex).

It should be noted that FIG. 6 is merely one example of the disclosed methods. In some embodiments, the classification steps and detection steps occur simultaneously. For example, if the clotting assay is an assay performed using the method and apparatus where multiple clotting assays are performed simultaneously (using, for example, the TEG method and apparatus disclosed in U.S. Pat. No. 7,261,861), one can easily envision the scenario where, if a single cassette contains four channels, the four channels may contain (a) control blood component from a donor known not to be taking an anticoagulant in the presence of a Factor Xa reagent, (b) test blood component in the presence of a Factor Xa reagent, (c) control blood component in the presence of an ecarin reagent, and (d) test blood component in the presence of an ecarin reagent. Where the normal ranges of the control blood component is pre-determined, the four channels may be, for example, (a) test blood without Factor Xa reagent, (b) test blood with Factor Xa reagent, (c) test blood without ecarin reagent, and (d) test blood with ecarin reagent. Of course, the routinely skilled practitioner can utilize any clotting assay to determine the information needed to determine if the patient is taking an anticoagulant and, if so, whether that anticoagulant is a DTI or an antiFactor Xa anticoagulant.

The following examples are provided which are meant to illustrate but not limit the various embodiments of the invention described herein.

Example 1

The TEG clotting assay was used to determine if low, normal, and high doses of dabigatran, rivaroxaban, and apixaban could be detected in blood spiked with these compounds. Three oral anticoagulants (OAC), namely dabigatran, rivaroxaban, and apixaban, were spiked into blood obtained from 14 healthy volunteer human donors. For each OAC tested, citrated blood from three donors was spiked with three different concentrations of the active drug (i.e., the compound). The spiked blood samples and control samples spiked with diluent were tested with the TEG® 5000 Thrombelastograph® Hemostasis Analyzer (Haemonetics Corporation, Braintree, Mass., USA) using the Kaolin and RapidTEG® reagents (Haemonetics). Each sample was run in triplicate. All samples were tested with and without ecarin (purchased from Enzyme Research Laboratories, South Bend, Ind.). This study was IRB approved and all donors were over 18 and signed informed consent forms.

Sample Preparation

Blood was drawn using standard venipuncture technique and a Becton Dickinson Vacutainer Push Button Collection set with a 21-gauge needle. Blood was spiked and tested within two hours of being drawn.

Dabigatran stock was prepared from the active dabigatran moiety (Alsachim, France) by dissolution in 0.1M HCl and further dilution in 1:1 DMSO:H2O. The final stock used to spike the blood had a concentration of 20 ng/pL in 0.1M HCl/DMSO/H2O. Tubes of citrated blood were spiked with this dabigatran stock to create final concentrations of 500, 200, and 50 ng/mL of citrated whole blood.

Dabigatran is approved for prevention of venous thromboembolism (VTE) following elective knee or hip replacement (220 mg/day for patients without renal impairment and 150 mg/day for patients with moderate renal impairment and for prevention of stroke in patients with renal impairment and atrial fibrillation (AF) in the US (at a reduced 75 mg/day dose). (Boehringer Ingelheim International, dabigatran etexilate product and prescribing information) A 150 mg oral dose of dabigatran has a maximum plasma concentration (C.) of 110 ng/mL (see Stangier et al., *Clin. Pharmacokinet.* 47: 285-295, 2008; Mueck, W., et al., *Thrombosis Journal* 11:10 (2013).

Rivaroxaban stock was prepared by agitation of a 20 mg Xarelto tablet (Jannsen, Titusville, N.J.) in a 1:1 DMSO:H$_2$O solution, which was diluted to a final concentration of 20 ng/uL rivaroxaban in 1:1 DMSO:H2O. Tubes of citrated blood were spiked with this rivaroxaban stock to create final concentrations of 500, 89, and 22 ng/mL in citrated whole blood. Rivaroxaban is approved for the prevention of stroke and systemic embolism in adults with non-valvular AF (20 mg/day; EU and US), for the treatment of deep venous thrombosis (DVT) and pulmonary embolism (PE) and for the prevention of recurrent DVT and PE in adult patients (15 mg twice daily for 3 weeks followed by 20 mg/day; EU and US) (see Wong et al., J. Thromb. Haemost. 6: 820-829, 2008; Janssen Pharmaceuticals, rivaroxaban prescribing information. An oral dose of 10 mg of rivaroxaban has a $C_{max}$ of 141 ng/mL (see Mueck, W., et al., *Thrombosis Journal* 11:10, 2013; Kubitza D. et al., Clin Pharmacol Ther. 78:412-421, 2005). Apixaban stock was prepared in a similar manner from a 2.5 mg Eliquis tablet (Bristol-Myers Squibb, New York, N.Y.), with final concentrations of 1000, 500, and 250 ng/mL in whole blood. Apixaban is approved for prevention of VTE in elective hip or knee replacement surgery (2.5 mg BID) and for prevention of stroke and systemic embolism in patients with non-valvular AF (5 mg BID) (see Bristol-Myers SP, EEIG. apixaban summary of product characteristics). An oral dose of 20 mg of apixaban has a Cmax of 460 ng/mL mL (see Mueck, W., et al., *Thrombosis Journal* 11:10, 2013; Raghavan N et al., *Drug Metab Dispos.* 37:74-81, 2009). Control samples, prepared for each tested drug, included a solvent control containing only citrated blood and the diluent used to dilute the drug stock, and an unadulterated citrate blood tube.

Thromboelastography

Testing was performed on TEG-5000 analyzers (Haemonetics Corp., Braintree, Mass., USA) using Kaolin vials, 0.2M CaCl2, RapidTEG (rTEG) vials, diluent water, and disposable clear cups and pins provided by the manufacturer (Haemonetics, Braintree, Mass.), and ecarin (Enzyme Research Laboratories, South Bend, Ind.). All testing was performed in triplicate at each dose, and allowed to continue until the MA (maximum amplitude) parameter defined. The various components of the TEG tracing are depicted in FIG. 3A. The Kaolin test generates an R parameter, which is measured in minutes, and is the time elapsed from the initiation of the test until the point where the onset of clotting provides enough resistance to produce a 2 mm amplitude reading on the TEG tracing. This parameter represents the initiation phase of coagulation related to the function of enzymatic clotting factors. The R parameter has a normal range of 5 to 10 min for kaolin. A prolonged R time indicates slower clot formation. K is a measurement of the time interval from the split point to the point where fibrin cross-linking provides enough clot resistance to produce a 20 mm amplitude reading. The α angle is the angle formed by the slope of a tangent line traced from the R to the K time and a central line measured in degrees. K time and the α angle denote the rate at which the clot strengthens, and is representative of thrombin's cleaving of the available fibrinogen into fibrin. The MA indicates the point at which clot strength reaches its maximum amplitude, measured in millimeters on the TEG tracing, and reflects the end result of maximal platelet-fibrin interaction via the GPIIb-IIIa receptors (see Khurana S et al., *J Lab Clin Med.* 130:401-411, 1997).

The RapidTEG (rTEG) test incorporated both tissue factor and kaolin to generate the conventional kaolin parameters as well as the TEG-ACT parameter, which is measured in seconds. The TEG-ACT is equivalent to the Activated Clotting Time (see Chavez J. J. et al., Anesth. Analg. 99:1290-1294, 2004) and has a normal range of 86 to 118 seconds. A prolonged TEG-ACT time indicates slower clot formation. In addition, velocity curves derived from the above mentioned kaolin and rTEG tests were plotted using TEG software. These curves represent the speed of clot propagation (MRTG, Maximum Rate of Thrombus Generation; and TMRTG, Time to Maximum Rate of Thrombus Generation) (see FIG. 3B).

For the kaolin test, 1 mL of citrated blood sample was mixed with kaolin and 340 microliters (μL) of this blood was added to a TEG cup containing 20 μL of 0.2M CaCl2 for recalcification. The kaolin with ecarin test was performed in a similar fashion, using 20 μL of an ecarin/CaCl2 solution (0.16 M CaCl2; 19 EU/mL ecarin).

For the RapidTEG (rTEG) test, the reagent was reconstituted with 20 μL diluent water, and allowed to stand for 5 minutes per manufacturer instructions. Ten μL of this reconstituted reagent was added to the TEG cup with 20 μl 0.2M CaCl2 for recalcification.

340 μL of the citrated blood sample was added to the cup with these two reagents, and the contents of the cup were mixed 3 times by drawing the contents of the cup up into the pipette and redispensing it into the cup. The test was started immediately after mixing and allowed to run until the MA parameter had defined. The rTEG with ecarin test was performed as the rTEG test above, using 20 μL of an ecarin/CaCl2 solution (0.16M CaCl2; 19 EU/mL ecarin).

Statistical Analysis

Statistical analyses were done using a two-tailed Student's t test. For all analyses, a P value of <0.05 was deemed statistically significant.

Figure 7A:
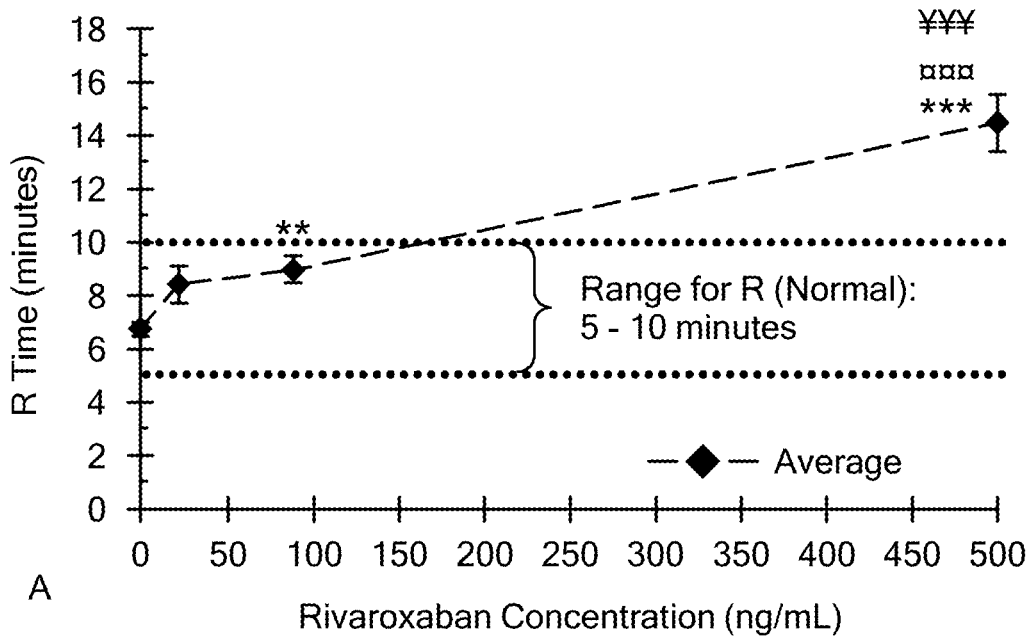
FIGS. 7A-7F are line graphs.
Figure 7B:
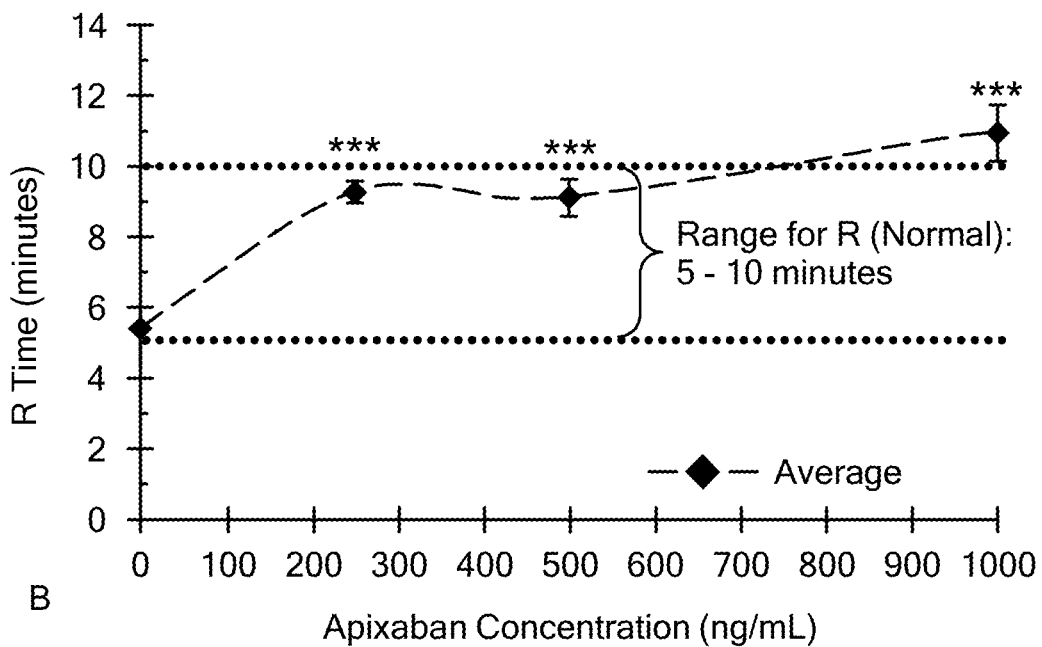
Figure 7C:
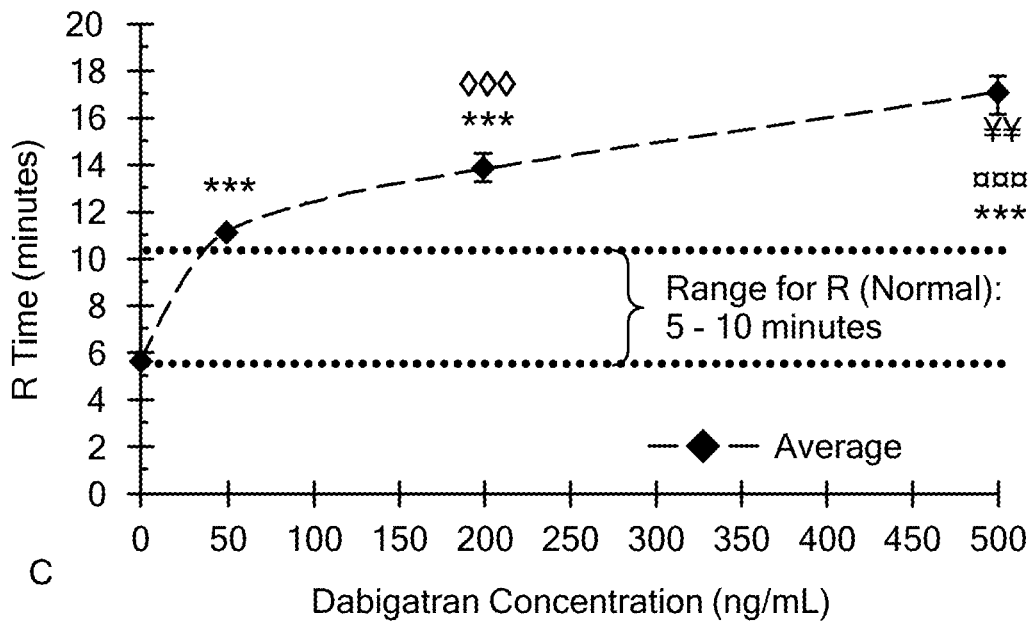

Results:

The results of the Kaolin test are shown in Table 1 and in FIGS. 7A, 7B, and 7C.

Figure 17:
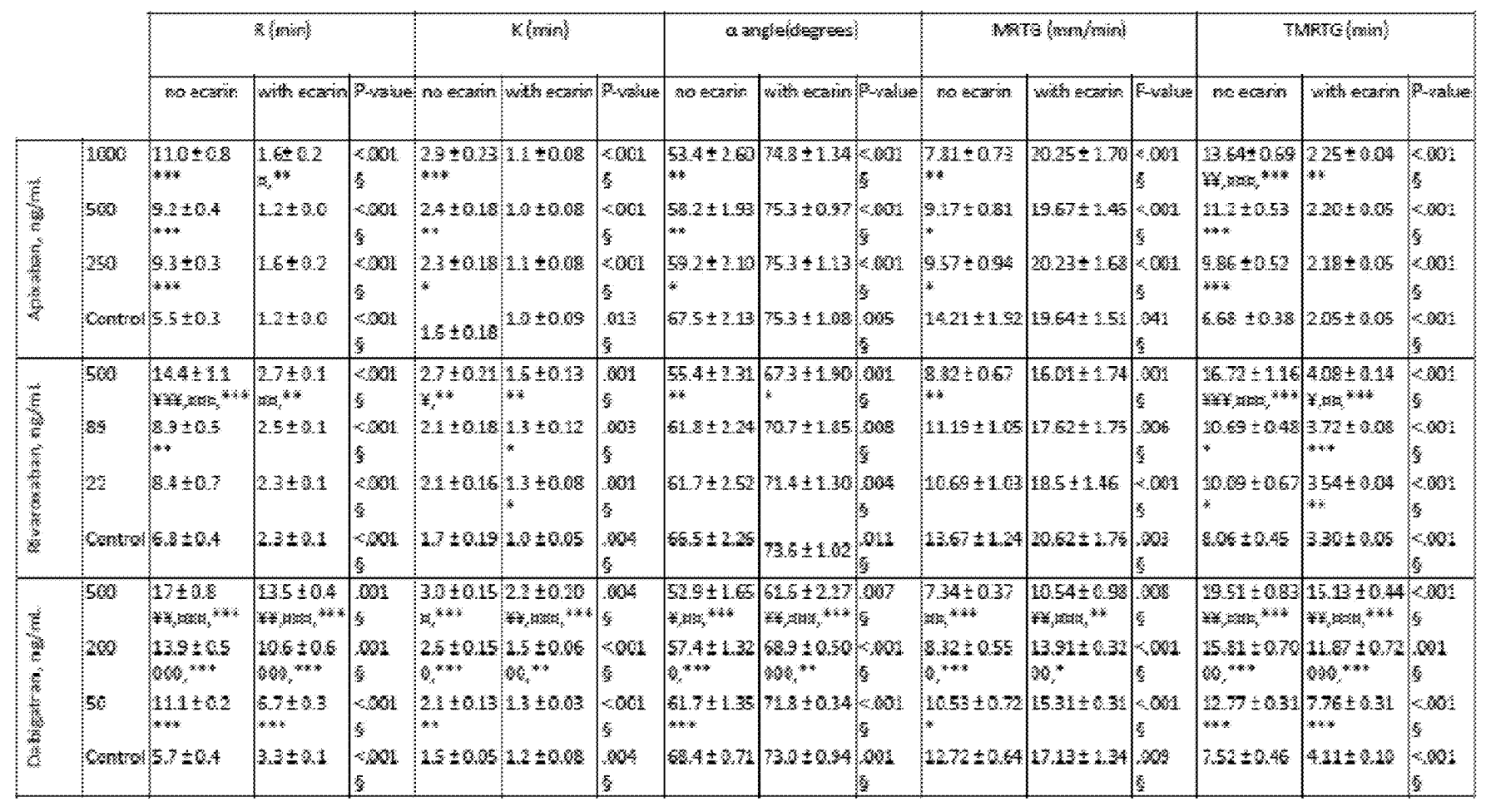

FIG. 17 shows the TEG Kaolin test coagulation parameters' sensitivity in healthy donor spiked samples with different doses of apixaban, rivaroxaban and dabigatran in the presence or absence of ecarin. In FIG. 17, R—Reaction Time; MRTG—Maximum Rate to Thrombus Generation; TMRTG—Time to Maximum Rate of Thrombus Generation. Statistically significant between: ¥—higher dose and medium dose; ¤—higher dose and lower dose; ◊—medium dose and lower dose; *—the control. §—paired sample with or without Ecarin. SDR—standard error of the mean of three independent experiments measured in triplicate. 1 symbol p<0.05; 2 symbols p<0.01; 3 symbols p<0.001.

The R, K, α, and MRTG parameters in the kaolin test only achieved statistical significance for the higher concentrations of rivaroxaban (FIG. 17, FIG. 7A) but were able to detect the presence of all tested concentrations of Apixaban (P<0.045) (FIG. 17, FIG. 7B) and Dabigatran (P<0.038) (FIG. 17, FIG. 7C). In addition, for all drugs the TMRTG parameter was statistically different between the control group and all tested concentrations. Furthermore, the R, α, and TMRTG parameters for the dabigatran samples were significantly different between all concentrations indicating an appropriate dose response (FIG. 17, FIG. 7C). Finally, the MA values from the kaolin test for rivaroxaban and dabigatran did not change with the addition of the studied NOAC when compared to the control, illustrating the lack of effect of these agents on platelet/fibrin contribution to clot strength. However, apixaban tracing at a concentration of 250 ng/mL demonstrated that the MA was significantly different from the control group (P<0.001), however was still within normal range (data not shown).

FIG. 18 shows the Rapid TEG test coagulation parameters' sensitivity in healthy donor spiked samples with different doses of apixaban, rivaroxaban and dabigatran in the presence or absence of ecarin. Statistically significant between: §—paired sample with or without Ecarin. SDR—standard error of the mean of three independent experiments measured in triplicate. 1 symbol p<0.05; 2 symbols p<0.01; 3 symbols p<0.001

Figure 7D:
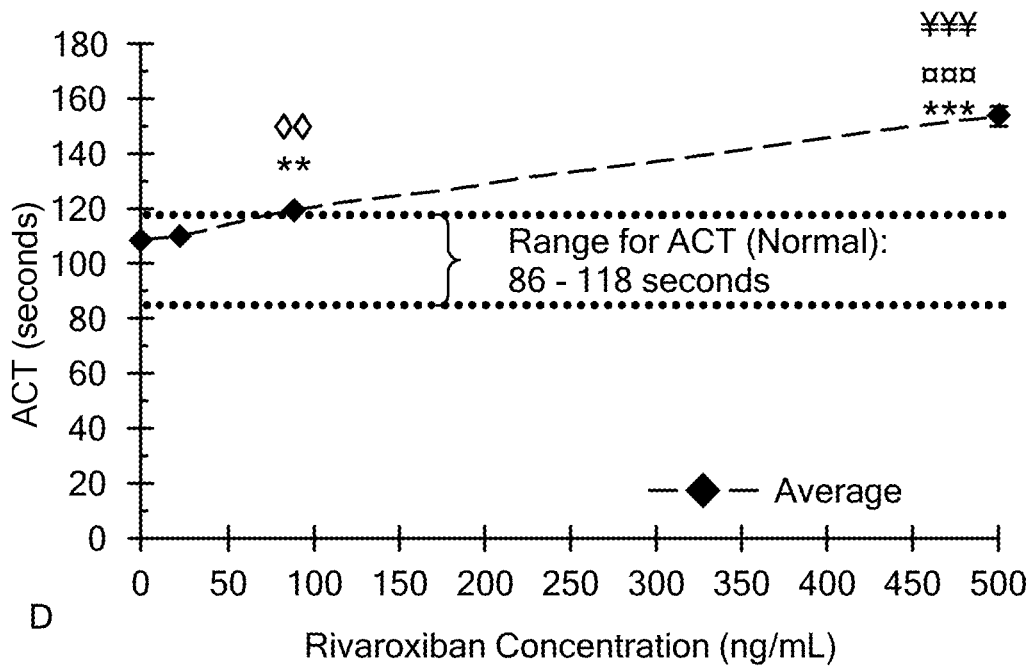
Figure 7E:
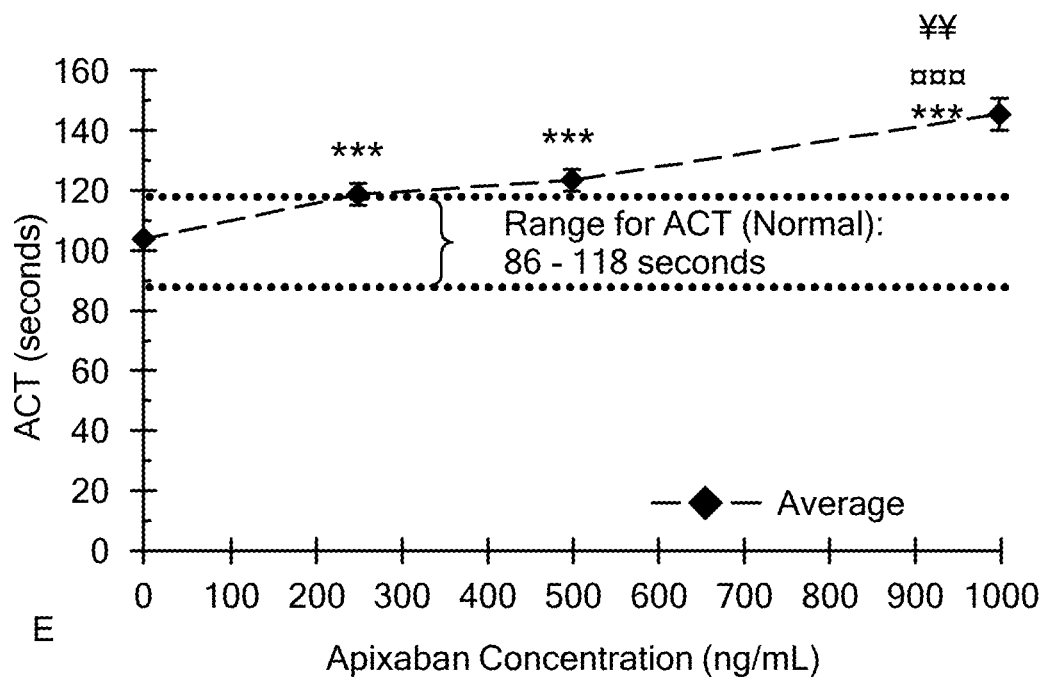
Figure 7F:
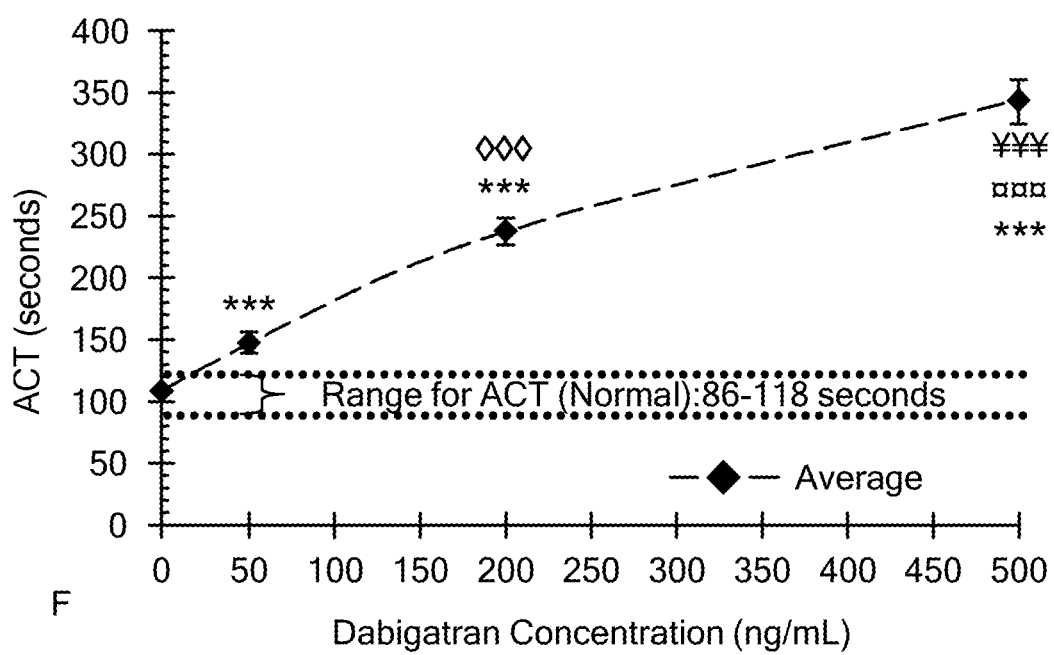

The TEG ACT parameter for all tested drugs in the RapidTEG test was significantly different between the control group and all tested concentrations of rivaroxaban, apixaban, and dabigatran. The results of this test are shown FIG. 18 and in FIGS. 7D, 7E, and 7F) with the exception of the rivaroxaban concentration of 22 ng/mL (P=0.576) (see FIG. 18, FIG. 7D).

Furthermore, the TEG ACT parameter was able to distinguish between concentrations of rivaroxaban (See the results in FIG. 18 and in FIG. 7D) and dabigatran (FIG. 18, FIG. 7F) indicating a good dose response curve. The K, α and MRTG parameters for both apixaban and rivaroxaban from the RapidTEG test did not show any statistical difference between the control or between studied concentrations. However, the K parameter for the dabigatran group was statistically different from control for the lower tested concentrations (200 ng/mL, P=0.003; 50 ng/mL, P=0.003) but not for the concentration of 500 ng/mL (P=0.438) and the α parameter from the dabigatran group was statistically different from control for the concentration of 500 ng/mL (P<0.01) and 50 ng/mL (P<0.001) but not for the concentration of 200 ng/mL (P=0.383). In addition, both K and a parameters were able to differentiate between the highest dabigatran concentration from the other concentrations (500 ng/mL vs 200 ng/mL, P=0.002; 500 ng/mL vs 50 ng/mL, P<0.001). Furthermore, the MRTG parameter was sensitive to the two lowest concentrations of dabigatran (500 ng/mL, P=0.061; 200 ng/mL, P=0.0015; 50 ng/mL, P<0.001). The TMRTG parameter from the RapidTEG test is sensitive to the presence of both rivaroxaban and dabigatran but not apixaban. Furthermore, the TMRTG parameter is able to differentiate between concentrations of dabigatran (500 ng/mL vs 200 ng/mL, P<0.001; 200 ng/mL vs 50 ng/mL, P<0.001). Finally, the MA values of the RapidTEG test for rivaroxaban and apixaban did not change with the addition of the studied drug concentrations when compared to control and only the MA values of the dabigatran 500 ng/mL concentration were significantly different from the control group (P<0.01), however was still within normal range (data not shown).

Ecarin is derived from the venom of the saw-scaled viper, *Echis carinatus*. Ecarin activates prothrombin (the precursor of thrombin—see FIG. 5). This activation of prothrombin by ecarin produces meizothrombin, a prothrombin-thrombin intermediate which has a low level of procoagulant enzymatic activity.

Figure 8A:
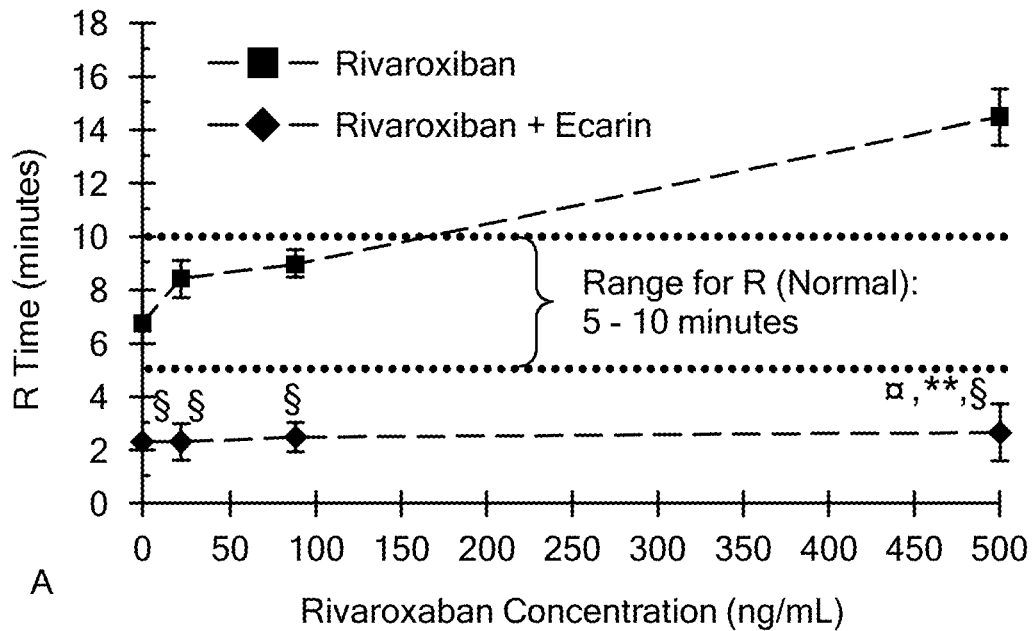
FIGS. 8A-8C are line graphs showing the results of TEG kaolin test R time as a function of drug concentrations in the presence or absence of ecarin for rivaroxaban (FIG. 8A), apixaban (FIG. 8B) and dabigatran (FIG. 8C). Rivaroxaban and apixiban both show an equivalent and significant shortening of R time due to a the presence of ecarin despite concentration of drug. Dabigatran has a concentration dependent decrease in R time. Dotted parallel bars show the normal ranges of R for normal donors. Statistically significant between: ¥—higher dose and medium dose; ¤—higher dose and lower dose; ◊—medium dose and lower dose; *—control. §—Statistically significant between paired sample with or without ecarin, p<0.001. Error bars represent the standard error of three independent experiments measured in triplicate.
Figure 8B:
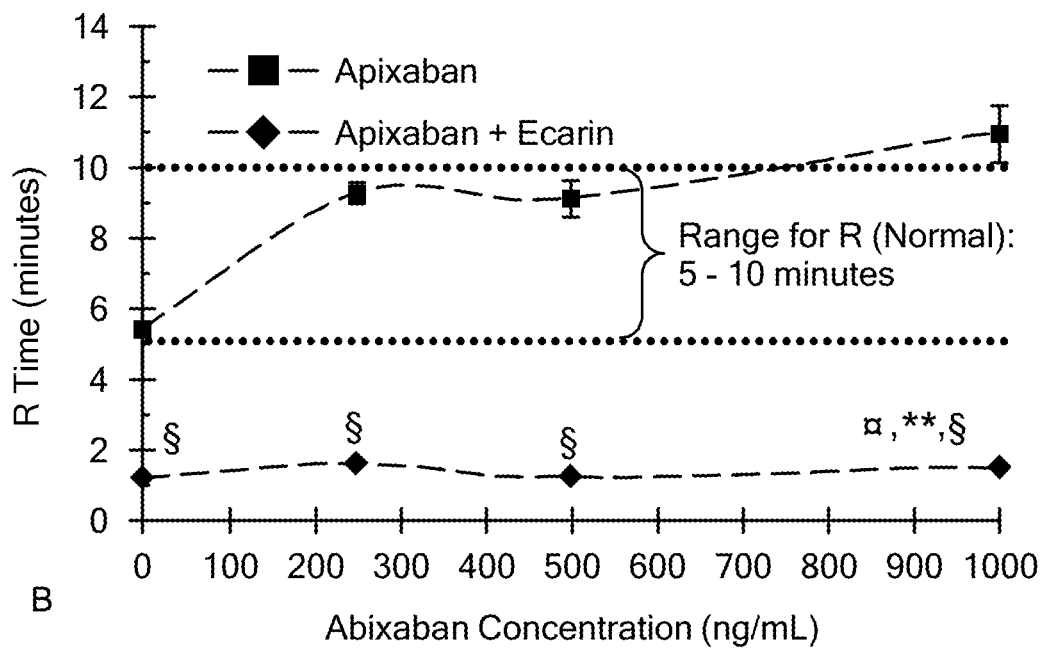
Figure 8C:
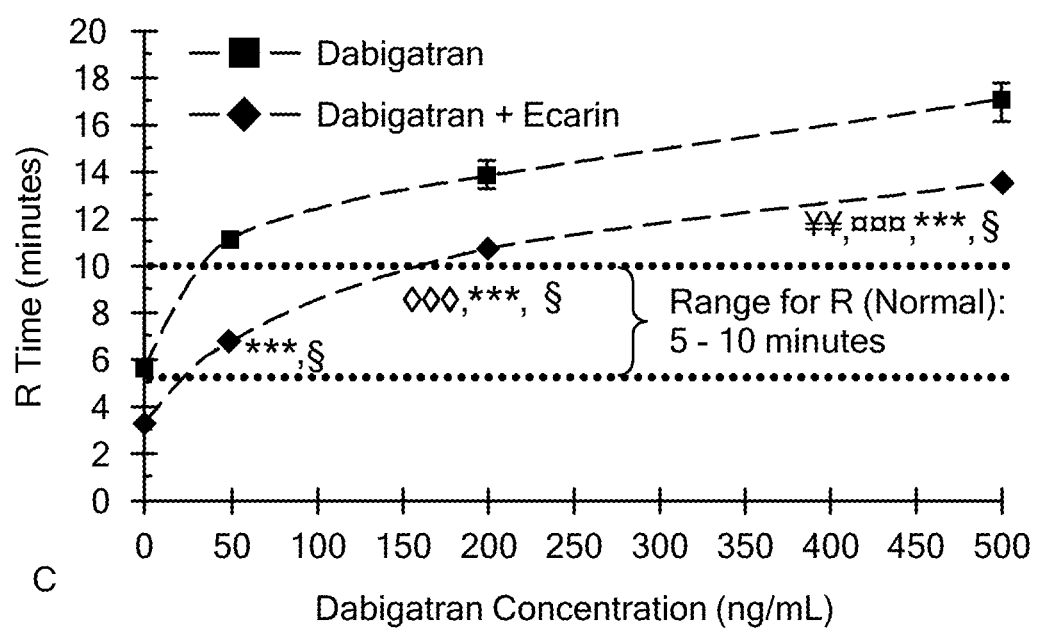

As can be seen in FIG. 17 and also in FIGS. 8A-8C, the addition of ecarin to the kaolin test caused a significant decrease of the R, K and TMRTG values for both treated and control groups (apixaban P<0.001; rivaroxaban P<0.003; dabigatran P<0.004) and a significant increase of the α and MRTG values for both treated and control groups (apixaban P<0.001; rivaroxaban P<0.008; dabigatran P<0.008) (see FIG. 17). Furthermore, the addition of ecarin to the kaolin test in the presence of anti-Factor Xa drugs (also simply called anti-Xa drugs) severely decreases the R values to the hypercoagulable range (<5 min) with no statistical difference from the control with the exception of the higher studied dosages (Apixaban: 1000 ng/mL, P=0.026; 500 ng/mL, P=0.756; 250 ng/mL, P=0.054), Rivaroxaban (500 ng/mL, P=0.0017; 89 ng/mL, P=0.079; 22 ng/mL, P=0.898) while in the presence of dabigatran there is only a dose related decrease of the R (FIG. 17, see also FIG. 8C). The addition of ecarin to the kaolin test did not change the MA values of the samples for dabigatran or rivaroxaban relative to samples run without ecarin, but in the presence of apixaban the MA values were statistically different (1000 ng/mL, P=0.020; 500 ng/mL, P=0.009; 250 ng/mL, P<0.001) from samples run without ecarin, however was still within normal range (data not shown).

As can be seen in FIG. 18, the addition of ecarin to the RapidTEG test significantly decreases the TEG-ACT times for both anti-Xa and DTI drugs (apixaban, P<0.001; rivaroxaban, P≤0.001; dabigatran, P<0.001) as well as the TMRTG times in the presence of both rivaroxaban and dabigatran (rivaroxaban, P<0.001; dabigatran, P<0.001) increasing the hypercoagulable status (see FIG. 18). On the other hand, the RapidTEG α angle did not change for any of the studied concentrations when ecarin was added in the presence of rivaroxaban or apixaban. However, for the lowest concentrations of dabigatran there was a decrease of the angle value (200 ng/mL, P=0.047; 50 ng/mL, P=0.016). The RapidTEG K values significantly decreased for the highest and lowest concentrations of apixaban (1000 ng/mL, P=0.017; 250 ng/mL, P=0.17) and the middle concentration of rivaroxaban (89 ng/mL, P=0.044) but increased in the middle concentration of dabigatran (200 ng/mL, P=0.004) when ecarin was added. Finally, the addition of ecarin to the RapidTEG test only significantly decreased the MA value of the 200 ng/mL concentration of dabigatran (p<0.05), however this was still within normal range (data not shown).

Example 2

Healthy human volunteers (who are not being administered any anticoagulant), donated blood. Following donation, the blood collected from the donors (which was added to citrate to prevent clotting) was divided into portions, and portions of the blood were spiked with either nothing, dabigatran, or rivaroxaban. The portions were then assayed using thromboelastography, including assays performed in the presence of ecarin.

For these studies, blood from three healthy human volunteers was collected. For each dose, three thromboelastography assays were run, and the reported number indicates the averaged result. The direct thrombin inhibitor used was dabigatran. The stock of dabigatran was 1 ml DMSO+750 ul saline (0.9% NaCl)+1 mg active dabigatran moiety. The anti-Factor Xa drug used was rivaroxaban. The stock of rivaroxaban was a 20 mg tablet dissolved in 1 ml saline plus 9 ml DMSO.

Three dosages of each of dabigatran and rivaroxaban were used, namely a low dose, a normal dose, and a high dose. For dabigatran, the low dose was 50 ng/ml, the normal dose was 200 ng/ml, and the high dose was 500 ng/ml. For rivaroxaban, the low dose was 22 ng/ml, the normal dose was 89 ng/ml, and the high dose was 500 ng/ml.

Figure 9A:
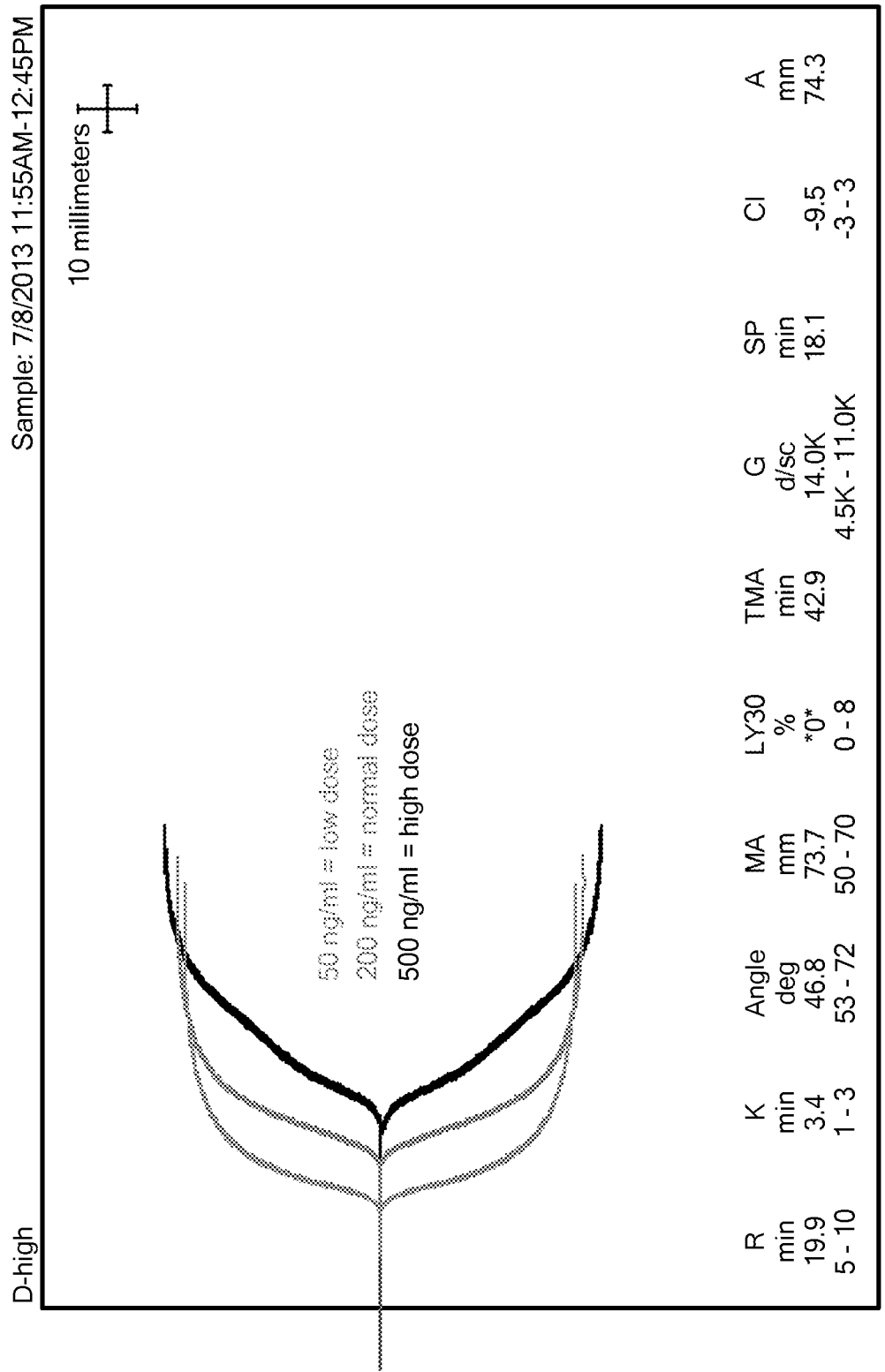
FIGS. 9A-9C are TEG tracings and line graphs showing clotting measurements of blood spiked with 50 ng/ml, 200 ng/ml, or 500 ng/ml of dabigatran in a standard Kaolin test.
Figure 9B:
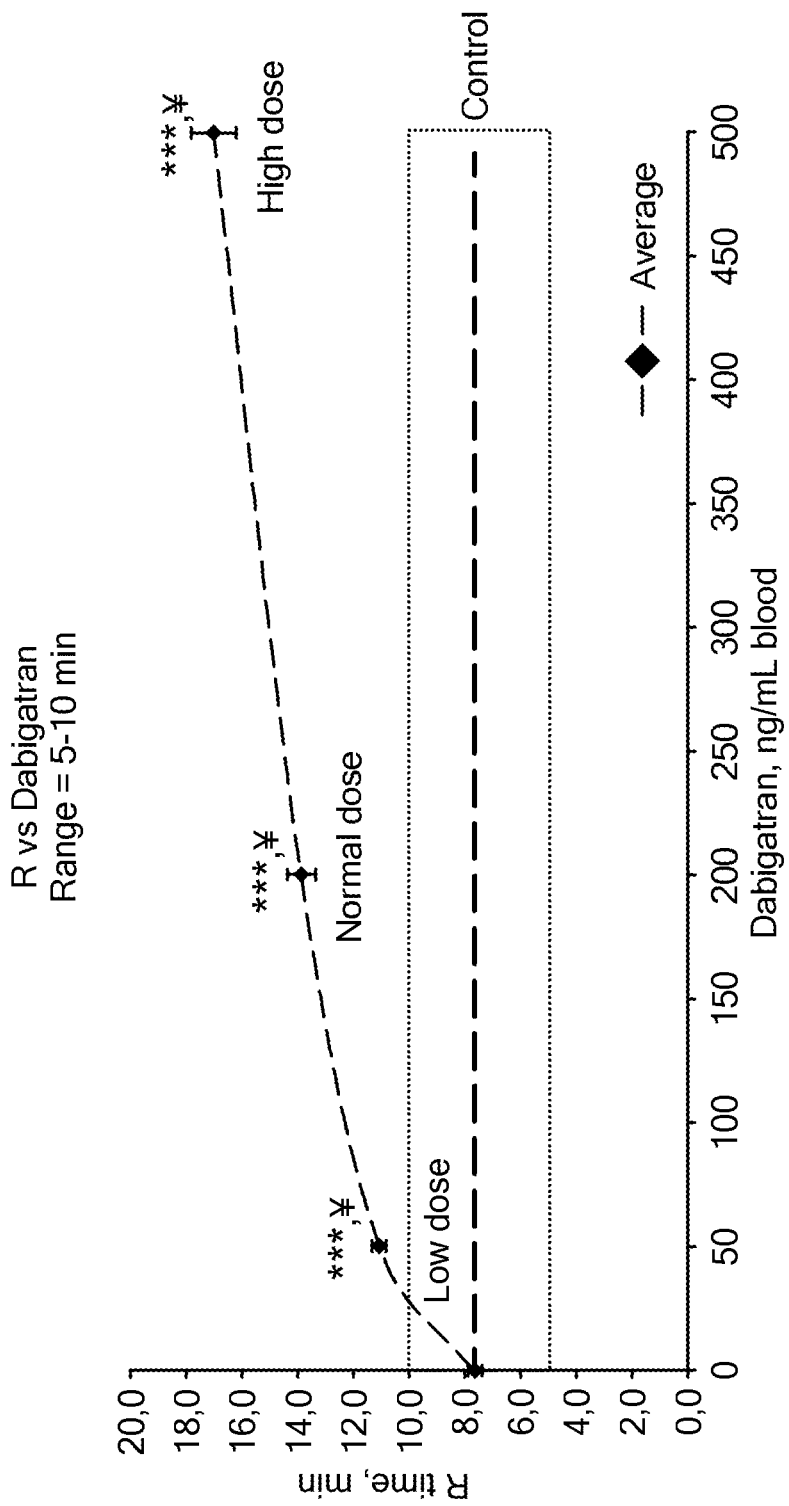
Figure 9C:
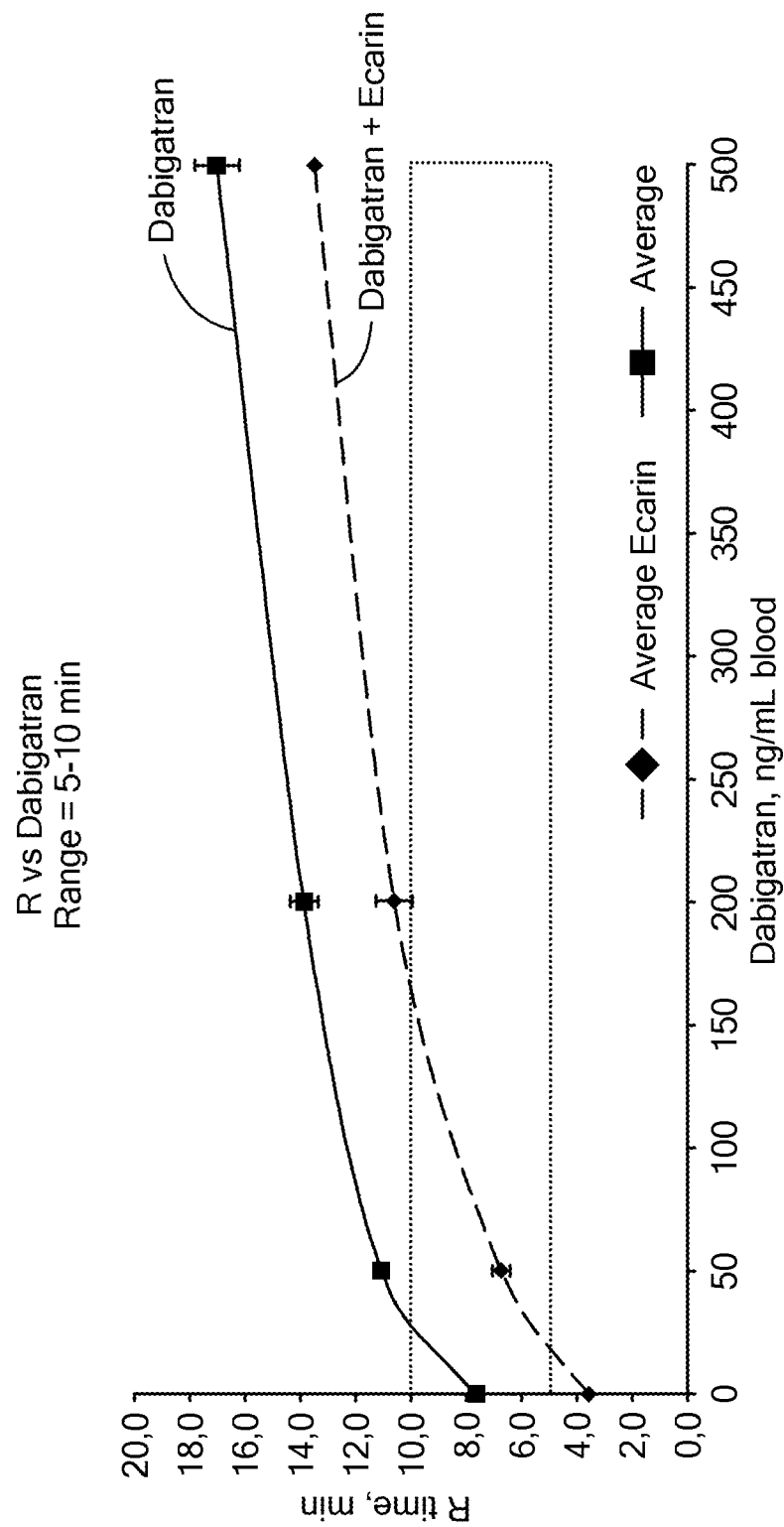

FIG. 9A shows the kaolin TEG tracing from blood components spiked with 50 ng/ml dabigatran (red line), 200 ng/ml dabiggatran (green line) and 500 ng/ml dabigatran (black line). As can be seen in FIG. 9A, the presence of dabigatran increases the R value of the tested blood components in a dose dependent manner. FIG. 9B is a plot of the R values of the spiked blood components compared to the R value of control blood component (i.e., taken from a volunteer known to not be taking an anticoagulant and whose blood was not spiked with an anticoagulant). Note that FIG. 9B is an enlargened view of FIG. 7C. As FIG. 9B shows, the reference range of the R value for the control blood was between about 5 minutes to about 10 minutes, where the average R value was about 7.9 minutes. The lowest dosage of dabigatran (50 ng/ml) resulted in an R value that was outside of the normal (i.e., control) reference range. Interestingly, when the blood components are treated with ecarin, the R value of the dabigatran-spiked blood is shortened and approaches the normal reference range (see FIG. 9C). Note that FIG. 9C is an enlargened view of FIG. 8C.

Figure 10:
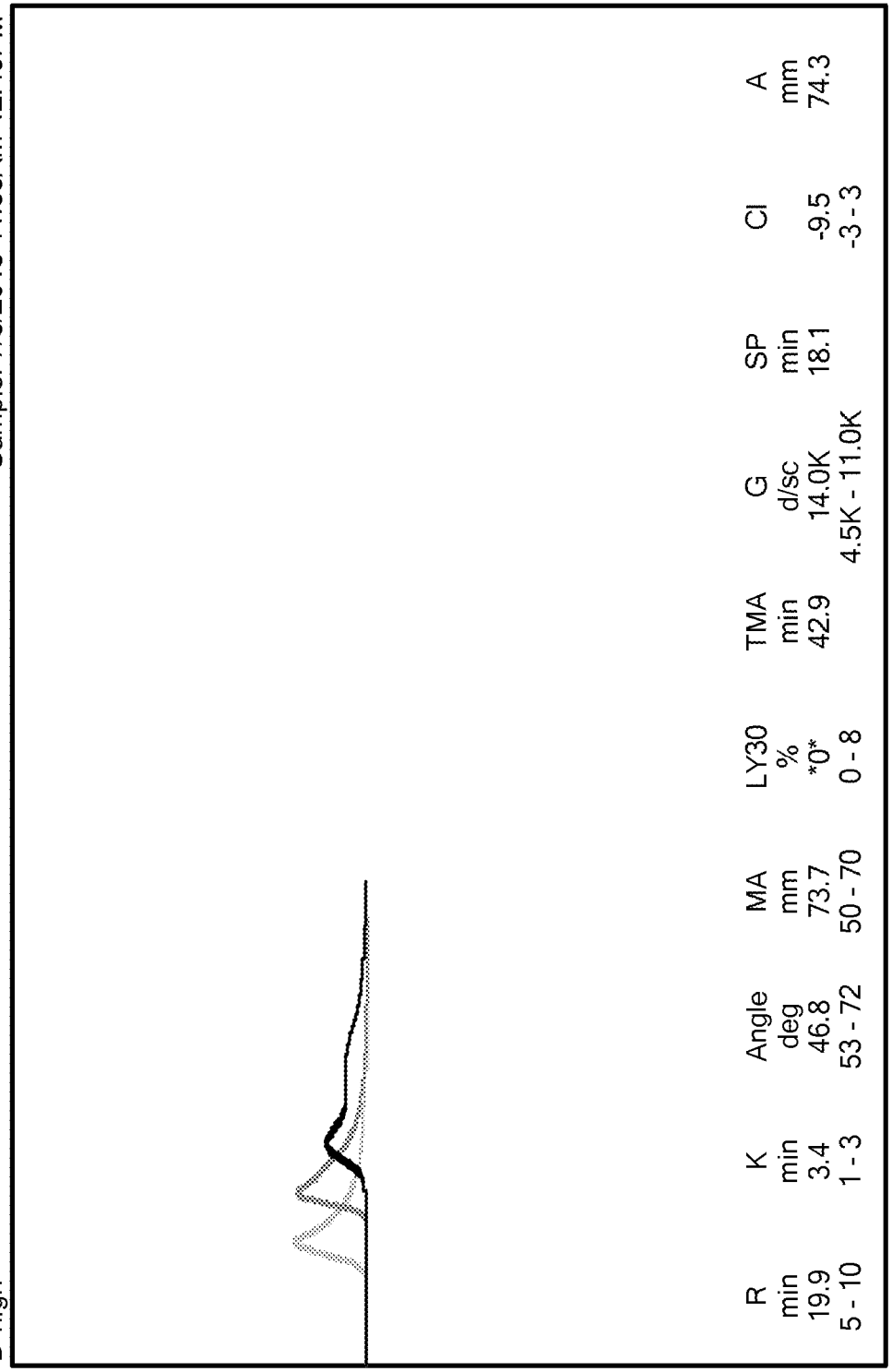
FIG. 10 is a schematic diagram showing standard TEG tracings which show the rate of thrombus generation in blood spiked with 50 ng/ml of dabigatran (pink, far leftline), 200 ng/ml of dabigatran (green, center line), or 500 ng/ml of dabigatran (white, far right line) using Kaolin.

FIG. 10 shows that the presence of dabigatran decreases the rate and time to achieve thrombus generation. These results are reflected in Table 3 below, measuring the MRTG (mm/min) and TMRTG (min) of the spiked blood. (See FIG. 3B for a description of these parameters).

TABLE 3

| Dabigatran (ng/ml) | MRTG (mm/min) | TMRTG (min) |
| --- | --- | --- |
| 500 | 7 | 22 |
| 200 | 12 | 18 |
| 50 | 13 | 13 |

Figure 11A:
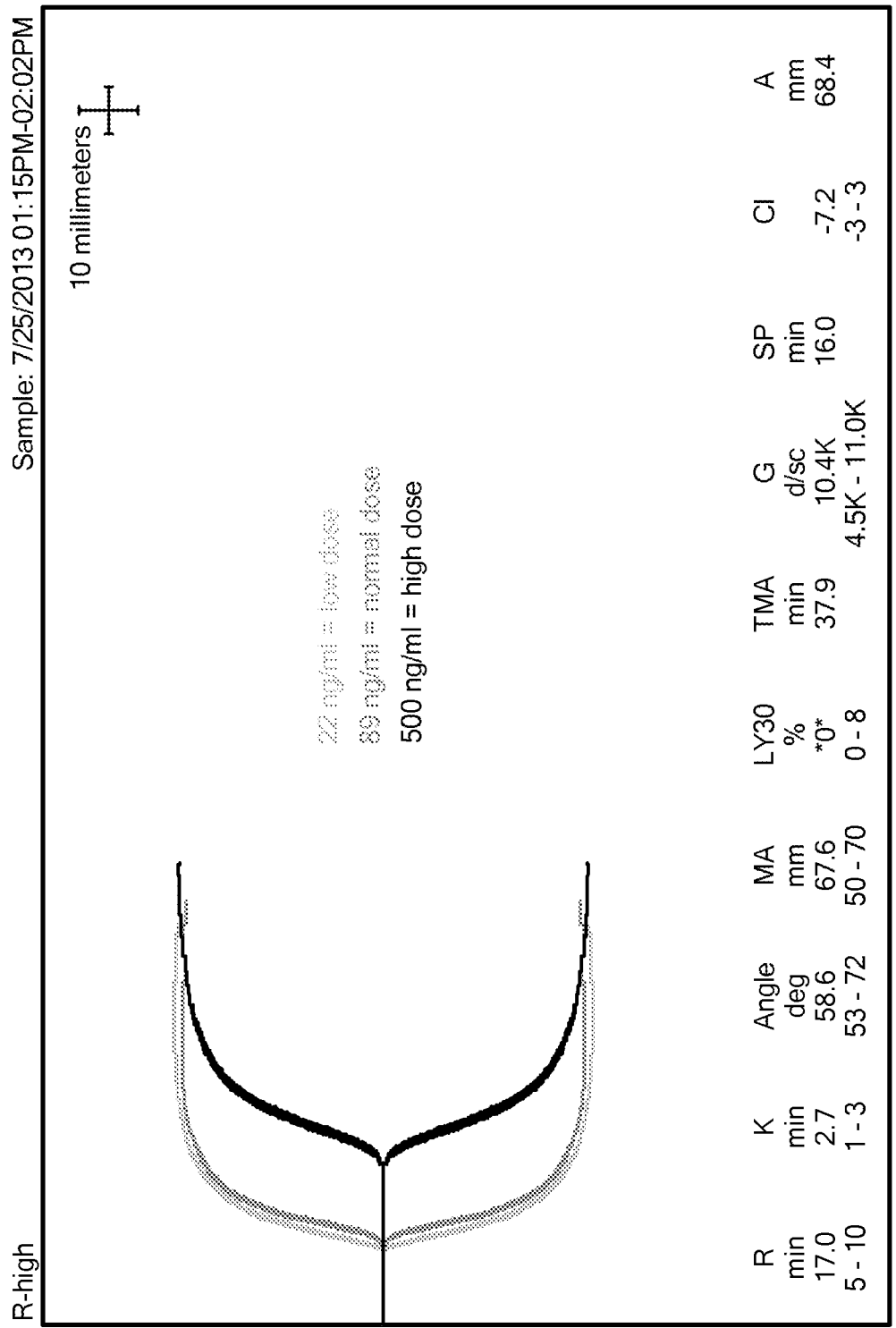
FIGS. 11A-11C are line graphs showing clotting measurements of blood spiked with 22 ng/ml, 89 ng/ml, or 500 ng/ml of rivaroxaban (a Factor Xa inhibitor anticoagulant) in a standard Kaolin test.
Figure 11B:
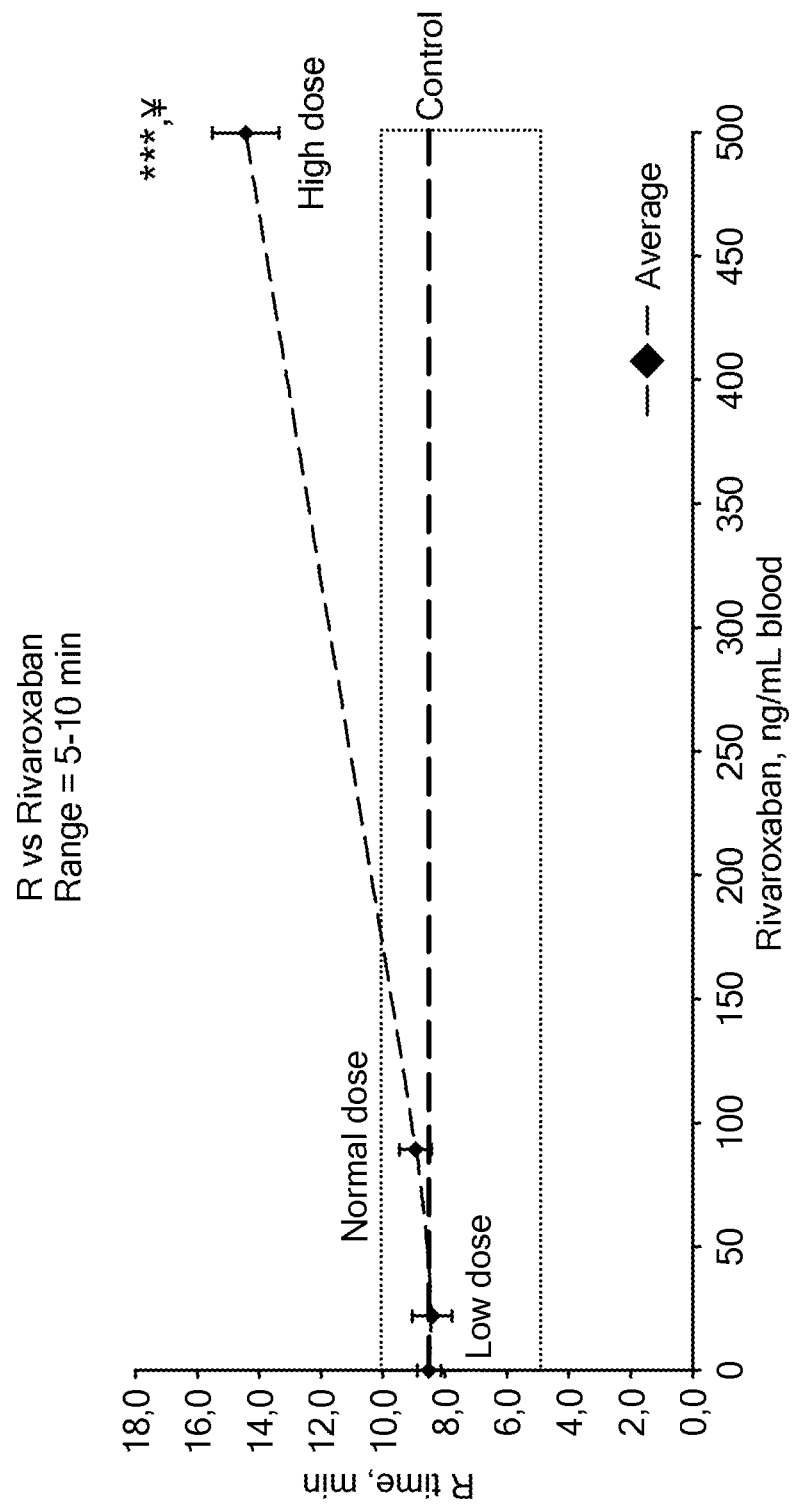
Figure 11C:
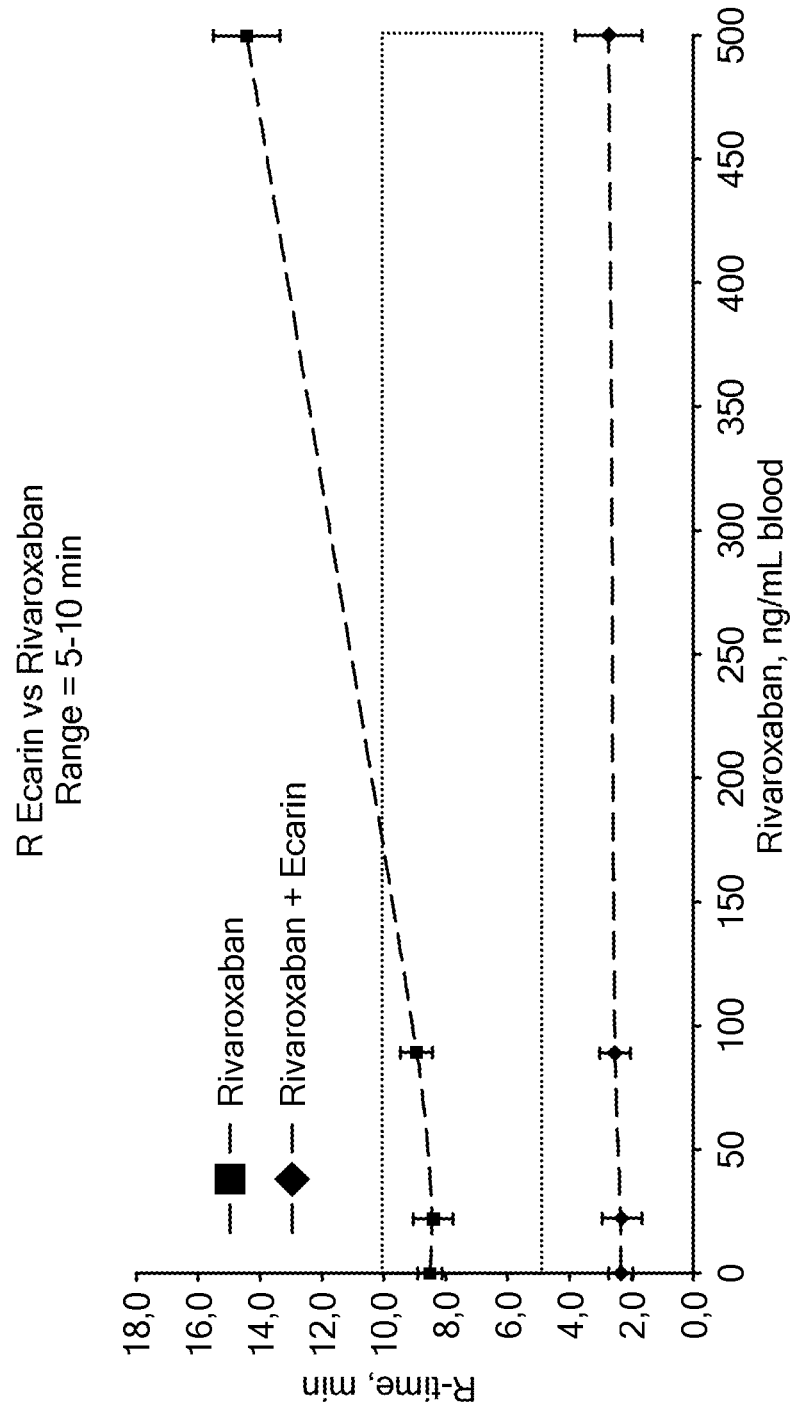

FIG. 11A shows the kaolin TEG tracing from blood components spiked with 22 ng/ml rivaroxaban (red line), 89 ng/ml rivaroxaban (green line) and 500 ng/ml rivaroxaban (black line). As can be seen in FIG. 11A, the presence of the high dosage of rivaroxaban increases the R value of the tested blood components in a dose dependent manner. FIG. 11B is a plot of the R values of the rivaroxaban-spiked blood components compared to the R value of control blood component (i.e., taken from a volunteer known to not be taking an anticoagulant and whose blood was not spiked with an anticoagulant). As FIG. 11B shows, the reference range of the R value for the control blood was between about 5 minutes to about 10 minutes, where the control R value was about 8.2 minutes. The highest dosage of rivaroxaban (500 ng/ml) resulted in an R value that was outside of the normal (i.e., control) reference range, while the lower two doses were within the control reference range. Interestingly, when the blood components are treated with ecarin, the R value of the rivaroxaban-spiked blood is dramatically shortened and all three dosage levels fall outside of the control reference range (see FIG. 11C).

Example 3

This method was performed to determine if TEG could be used to identify the presence of an anticoagulant in a blood component.

Blood from healthy volunteers known not to be taking any oral anticoagulant and without any other significant health issues are analyzed using the FXa or the Ecarin reagent in a TEG® hemostasis analyzer.

The FXa reagent (i.e., the Factor Xa reagent) is used to detect the presence (or absence) of an anticoagulant in the blood component being tested. In absence of any oral anticoagulant, the FXa reagent will accelerate the clotting process and result in a very short R-time. In presence of direct thrombin inhibitors and/or anti-Factor Xa anticoagulant(s), the process is slowed down and will cause elongation of the R-time. This difference in R-time is utilized to detect the presence of the oral anticoagulant.

If before and after blood sample is available then the significant difference in R-time will be used to detect presence. However in an actual patient population it is assumed that before (drug) samples will not be readily available. In such a case a reference range generated from a sample healthy population will be used for detection. If the R-time from a blood sample is within normal range then it is concluded that no oral anticoagulation is present. If the R-time is out of range then the result will indicate the presence of an oral-anticoagulant in that person/donor.

The ecarin reagent is used to classify the type of anticoagulant. The R-time from the Ecarin assay is used to differentiate between the two available classes (Direct thrombin inhibitors and anti-Xa inhibitors). This ecarin reagent may be used in combination with the results from the FXa reagent to make a decision. A reference range will be generated from a sample healthy volunteer population (not on any drug) for this reagent.

According to this non-limiting embodiment of the invention, if the FXa reagent indicates presence of an oral anticoagulant then the Ecarin reagent R-time will be analyzed against the Ecarin reference range for classification purposes. If the R-time is within Ecarin normal range then the anticoagulant present will be an anti-Xa. An R-time that is out of (Ecarin normal) range will indicate the presence of a direct thrombin inhibitor.

The R-time generated from multiple donors was used to construct a reference range. Blood was spiked with either direct thrombin inhibitors or anti-Xa(s) at different concentrations and analyzed using the FXa reagent or the Ecarin reagent. The drug concentrations chosen represent the published therapeutic ranges for these two classes of drugs. This assay was repeated in multiple donors to account for possible donor variations.

Figure 12:
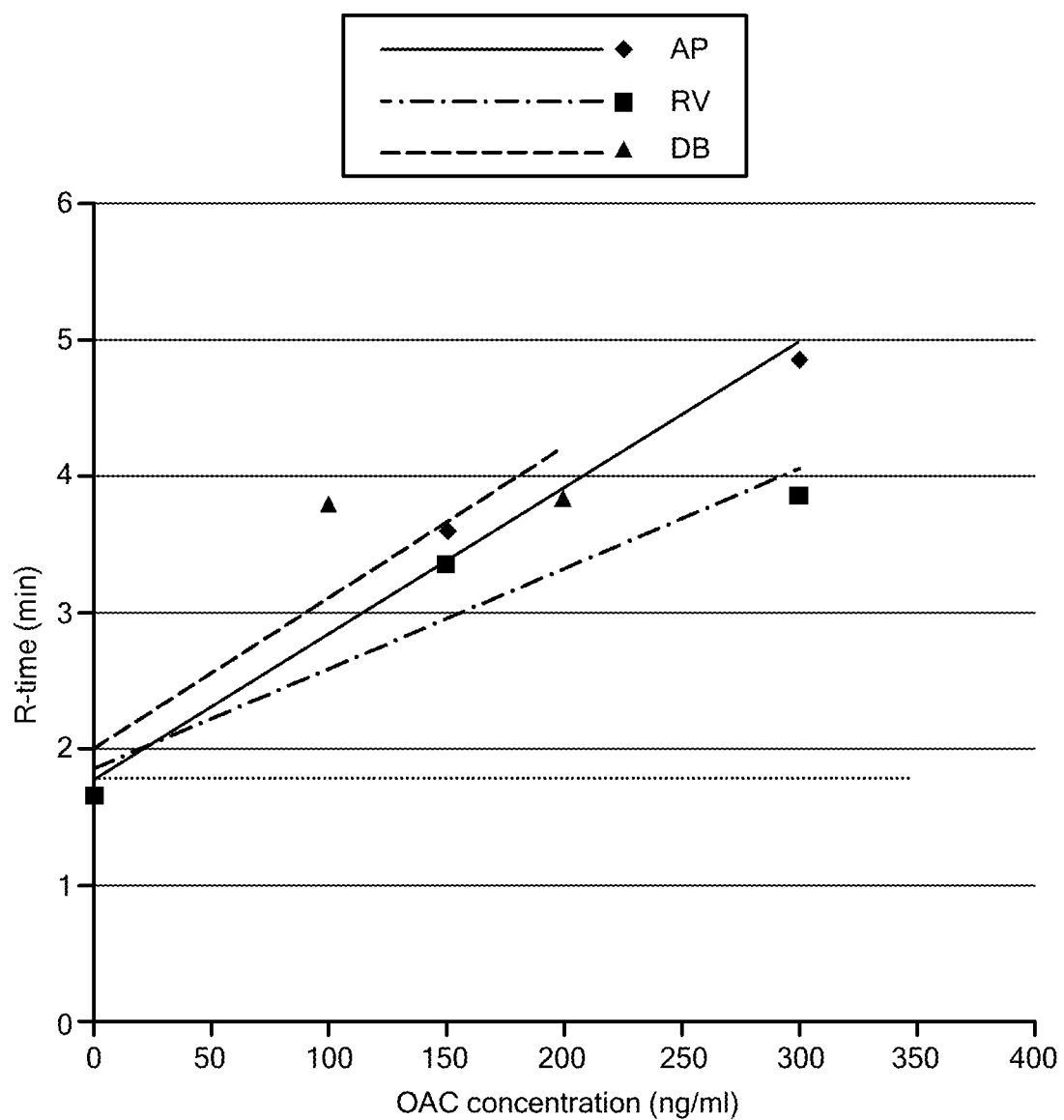
FIG. 12 is a line graph showing the R times in the presence of the FXa reagent from blood spiked with apixaban ("AP"; diamonds), blood spiked with rivaroxaban ("RV"; squares), and blood spiked with dabigatran ("DB"; triangles). The dotted horizontal line represents the R range for control blood (i.e., taken from a donor known not to be taking an anticoagulant and not spiked with any anticoagulant).

FIG. 12 shows the reference ranges for R time (in minutes) in the presence of the FXa reagent. The dotted line in FIG. 12 represents the normal reference range for the FXa reagent (i.e., R time of a blood component known to lack an anticoagulant in the presence of the FXa reagent. In absence of any oral anticoagulant the R-time will fall within this range (i.e., will be below approximately 1.8 minutes). In FIG. 12, AP and RV refer to Apixaban and Rivaroxaban respectively and is representative of two non-limiting anti-Xa drugs. A non-limiting direct thrombin inhibitor (DTI) is represented by DB or Dabigatran in FIG. 12. In vitro spiking of the blood from the same donor (who is known not to be administered with an anticoagulant) with either one of the anti-Xa drugs (i.e., AP or RV) or with the direct thrombin inhibitor (i.e., DB) resulted in a dose dependent elongation of the R-time compared to the reference range.

In some embodiments, the reference range of control blood (i.e., taken from a donor to whom an anticoagulant has not been administered) in the presence of FXa is between about 1.0 min to about 2.0 minutes. In some embodiments, the reference range of control blood (i.e., taken from a donor to whom an anticoagulant has not been administered) in the presence of FXa is between about 1.5 min to about 1.9 minutes. In some embodiments, the reference range of control blood (i.e., taken from a donor to whom an anticoagulant has not been administered) in the presence of FXa is about 1.8 minutes.

As shown in FIG. 12, a concentration of 100 ng/ml of drug in the blood component (where this amount is a therapeutically relevant amount of AP, RV, and DB) raises the R time by at least 1.25 times, or at least 1.5 times, or at least 1.75 times, or at least 2 times above the reference range of approximately 1.8 minutes.

Figure 13:
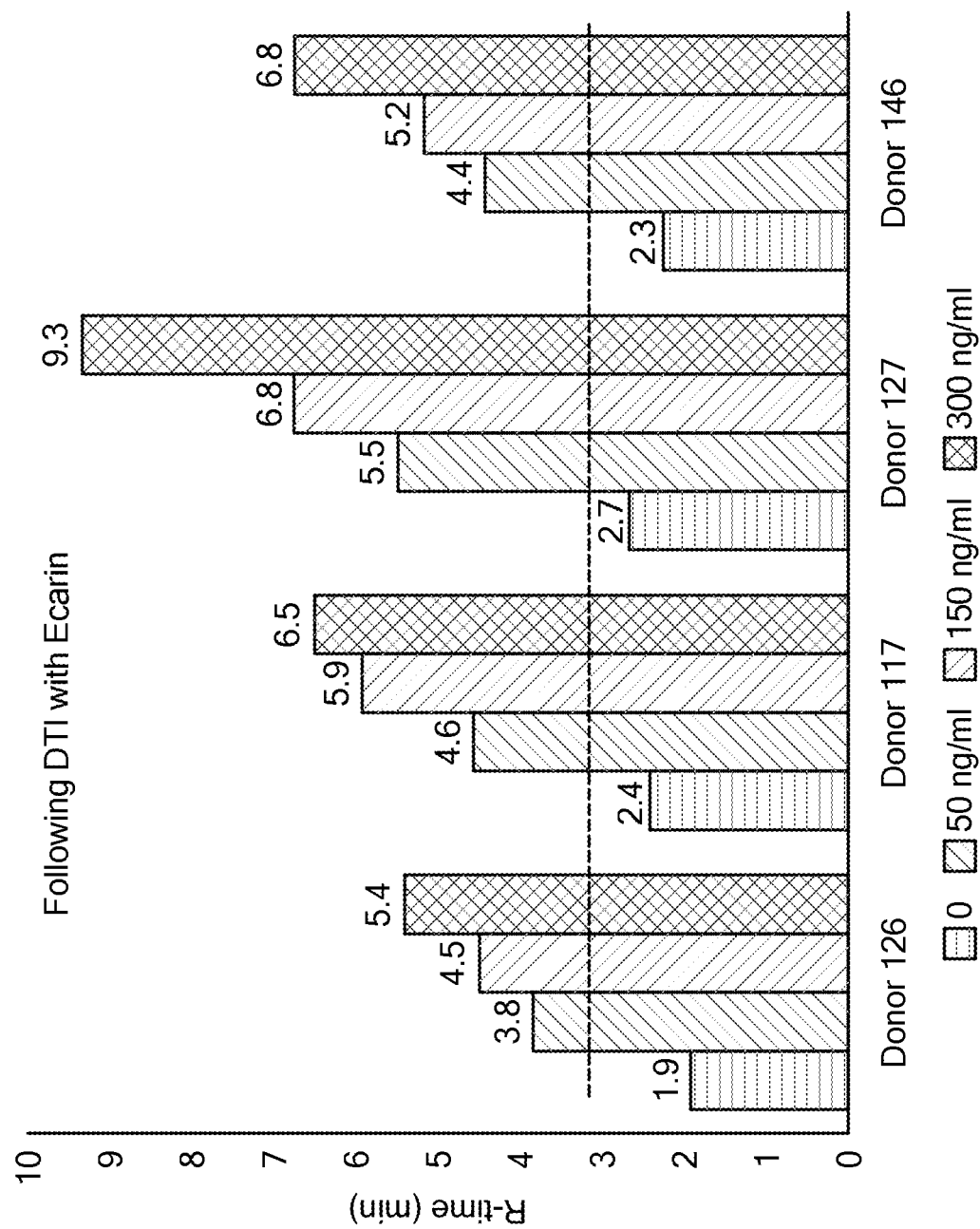
FIG. 13 is a bar graph showing the R times in presence of ecarin from blood from the indicated donors spiked with 0 ng/ml dabigatran, 50 ng/ml dabigatran, 150 ng/ml dabigatran, or 300 ng/ml dabigatran. The horizontal dotted line represents the R range for control blood (blood without anticoagulant).

Using the ecarin reagent, the presence of a direct thrombin inhibitor anticoagulant can be detected in a blood component using thromboelastography. FIG. 13 shows the R time measurements on blood components from four donors, whose blood (after being collected from the donor) was spiked with dabagatran at the indicated amounts and measured using thromboelastography in the presence of the ecarin reagent. The R time (in minutes) was compared to the R time obtained from donor blood with no oral anticoagulant (who is known not to be administered with an anticoagulant) treated with the ecarin reagent and measured using thromboelastography.

In some embodiments, the reference range of control blood (i.e., taken from a donor to whom an anticoagulant has not been administered) in the presence of the ecarin reagent is between about 1.0 minutes to about 3.5 minutes. In some embodiments, the reference range of control blood (i.e., taken from a donor to whom an anti-coagulant has not been administered) in the presence of the ecarin reagent is about 1.5 minutes to about 3.25 minutes. In some embodiments, the reference range of control blood (i.e., taken from a donor to whom an anticoagulant has not been administered) in the presence of the ecarin reagent is between about 1.9 minutes to about 3 minutes. In some embodiments, the reference range of control blood (i.e., taken from a donor to whom an anti-coagulant has not been administered) in the presence of the ecarin reagent is about 3.1 minutes.

As FIG. 13 shows, the reference range from a particular donor can vary. For example, donor 126 has a low untreated R-time (i.e., when the blood from donor 126 is not spiked with DB). Spiking the blood of donor 126 with 50 ng/ml DB, and measuring the R time using thromboelastography in the presence of the ecarin reagent resulted in an increase in R time that was two times longer than the untreated R time of unspiked donor blood 126 (i.e., untreated or control blood). As shown in FIG. 13, this was true for the other donors as well as compared to unspiked blood from the same donors. Furthermore, using an R time of about 3.1 minutes as a collective reference range, the blood from donors 117, 127, and 146 spiked with 50 ng/ml DB (which is lower than the therapeutically relevant amount of 110 ng/ml of DB—see Muek et al., supra) in the presence of ecarin was at least 1.25 times, or at least 1.5 times greater than the reference range of 3.1 minutes. When looking at the R times of 150 ng/ml DB (which is a therapeutically relevant amount of DB), spiked blood from all four donors had an R time (in the presence of ecarin) that exceeded the collective reference range of 3.1 minutes by at least 1.25 times, or at least 1.4 times.

Using the ecarin reagent, the presence of an anti-Factor Xa anticoagulant drug can be detected in a blood component using thromboelastography.

Figure 14:
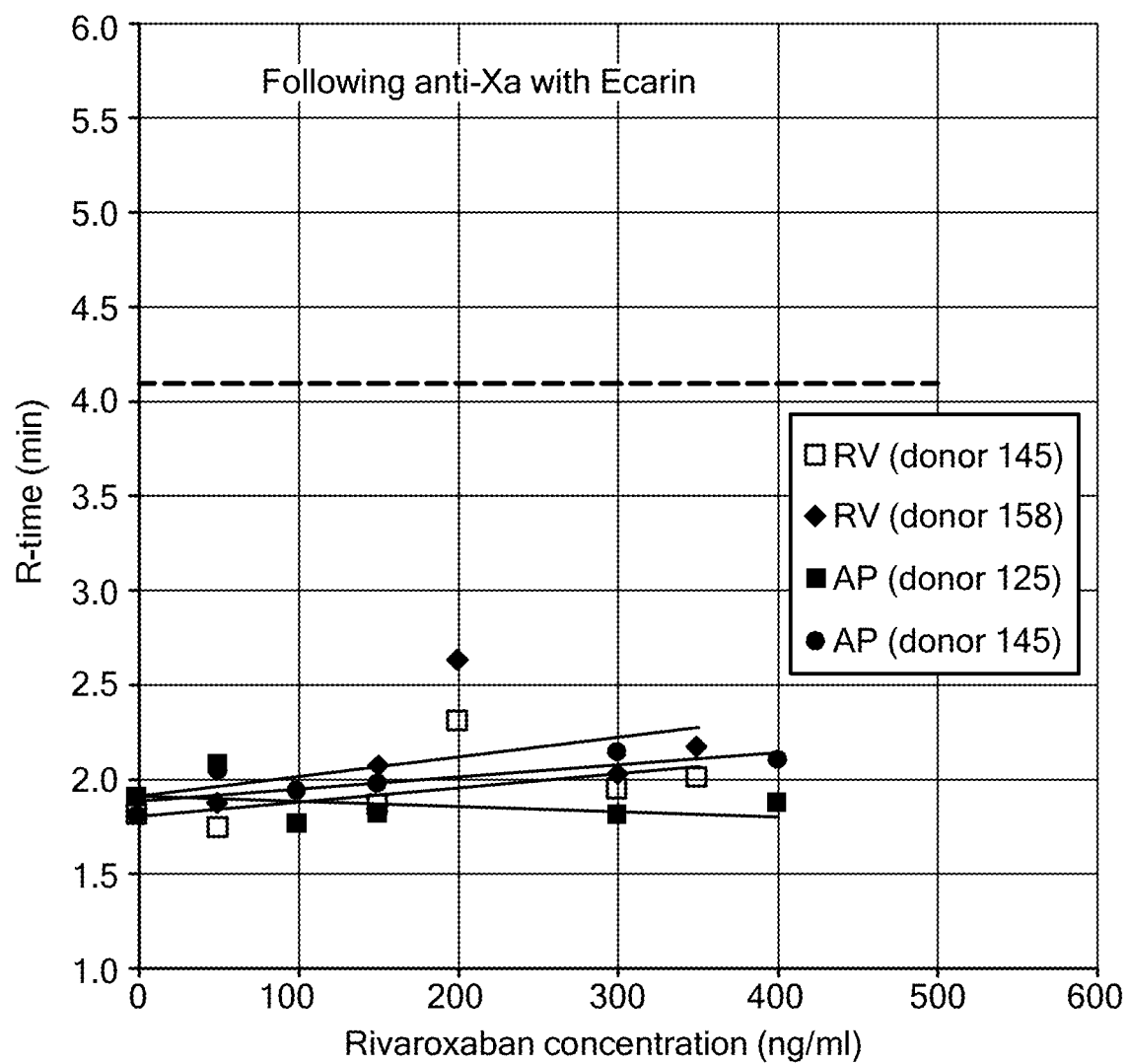
FIG. 14 is a line graph showing the R times of rivaroxaban or apixaban-containing blood from four donors in the presence of ecarin. The horizontal dotted line represents the R range for control blood (without any anticoagulant).

FIG. 14 shows the R time measurements on blood components from four donors, whose blood (after being collected) was spiked with rivaroxaban (an anti-Factor Xa drug) at the indicated amounts and measured using thromboelasography in the presence of the ecarin reagent. The R time (in minutes) was compared to the R time obtained from donor blood with no oral anticoagulant (i.e., taken from a patient who is known not to be administered with an anticoagulant) treated with the ecarin reagent and measured using thromboelastography.

In the assay performed in FIG. 14, the R time (in minutes) of control blood (i.e., taken from a donor to whom an anticoagulant has not been administered) in the presence of ecarin is between about 1 min to about 4.5 minutes (data not shown). In some embodiments, the reference range of control blood (i.e., taken from a donor to whom an anticoagulant has not been administered) in the presence of ecarin is between about 3.9 min to about 4.2 minutes. In some embodiments, the reference range of control blood (i.e., taken from a donor to whom an anticoagulant has not been administered) in the presence of ecarin is about 4.1 minutes.

As shown in FIG. 14, a concentration varying from 50-350 ng/ml of the RV drug in the blood component (where this represents a therapeutically relevant amount of RV) results in an R time that is within the reference range of approximately 1 to 4.1 minutes. Note that the reference range of the R time of the control blood will depend upon the patient from whom the blood was taken. In some embodiments, the R time of the RV-spiked blood is at least 1.25 times, or at least 1.5 times, or at least 1.75 times, or at least 2 times smaller slower than the upper boundary R time of the control blood.

A similar result is found for another anti-Factor Xa drug, namely apixaban (data not shown).

These results in FIG. 14 show that ecarin can be used to classify an anticoagulant as a Factor Xa molecule.

Example 4

Detection and Classification of an Anticoagulant Using the Factor Xa Reagent and Ecarin Blood from a single human volunteer was analyzed using thromboelastography with Factor Xa and ecarin before and after the volunteer was orally administered an anticoagulant.

For these studies, the normal ranges for the particular reagent (i.e., Factor Xa or ecarin) were determined using multiple donors known not to be taking any anticoagulant.

The human volunteer was known not to be taking (i.e., was not being administered) an anticoagulant. In this example, blood was taken from the volunteer before the volunteer was administered any anticoagulant. This is the "before" blood component sample. The volunteer was orally administered 20 mg rivaroxaban, an anti-Factor Xa anticoagulant. Two hours and thirty minutes after oral administration of the rivaroxaban, blood was drawn again from the volunteer. This is the "after" blood component sample.

The "before" and "after" samples were analyzed using thromboelastography in the presence of Factor Xa or in the presence of ecarin. When the R time is determined in the presence of Factor Xa, that time is called the detection time. When the R time is determined in the presence of ecarin, that time is called the classification time.

Figure 15A:
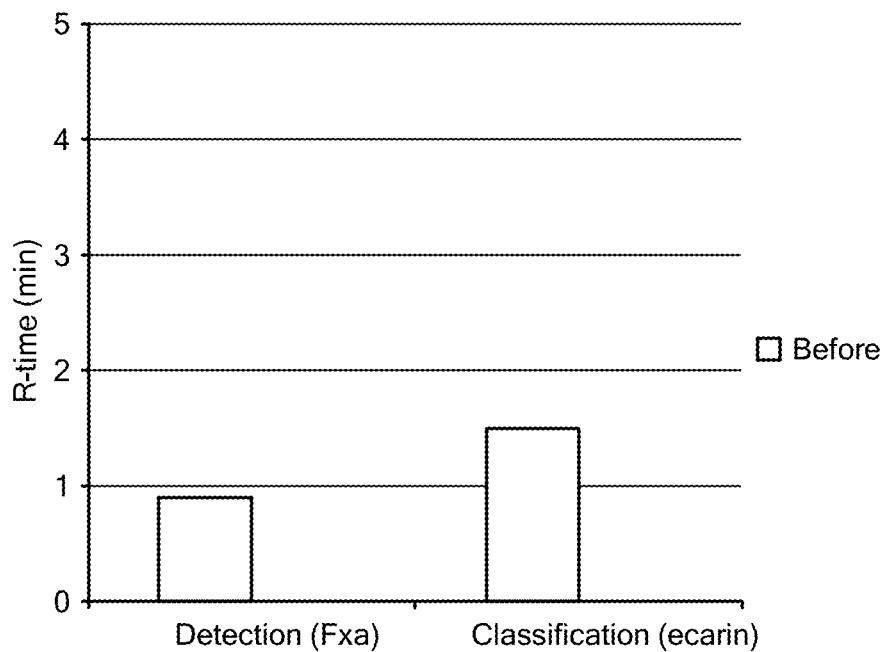
FIGS. 15A-15C are a series of bar graphs depicting the detection and classification steps of blood obtained from a patient before and after the patient had been administered an anticoagulant.

FIG. 15A shows the results of the "before" analyses (i.e., R times taken before the donor is administered an anticoagulant drug). In FIG. 15A, the solid horizontal line at approximately 1.5 minutes (in the detection time) and the solid horizontal line at approximately 4.1 minutes (in the classification time) indicates the upper boundary of the reference range for Factor Xa and ecarin, respectively, as determined from multiple human donors known to not be taking an anticoagulant (i.e., control donors). As shown in FIG. 15A, in the absence of any anticoagulant drug in the volunteer's blood (i.e., in the "before" blood samples), the R-time for the detection reagent (i.e., FXa) falls within normal range (i.e., is below the horizontal line) of the detection time As the R times was within the normal range (i.e., within the range of blood from control donors known not to be taking an anticoagulant), these findings confirmed the absence of any anticoagulant in the volunteer's blood. (See also the decision tree in FIG. 6).

Figure 15B:
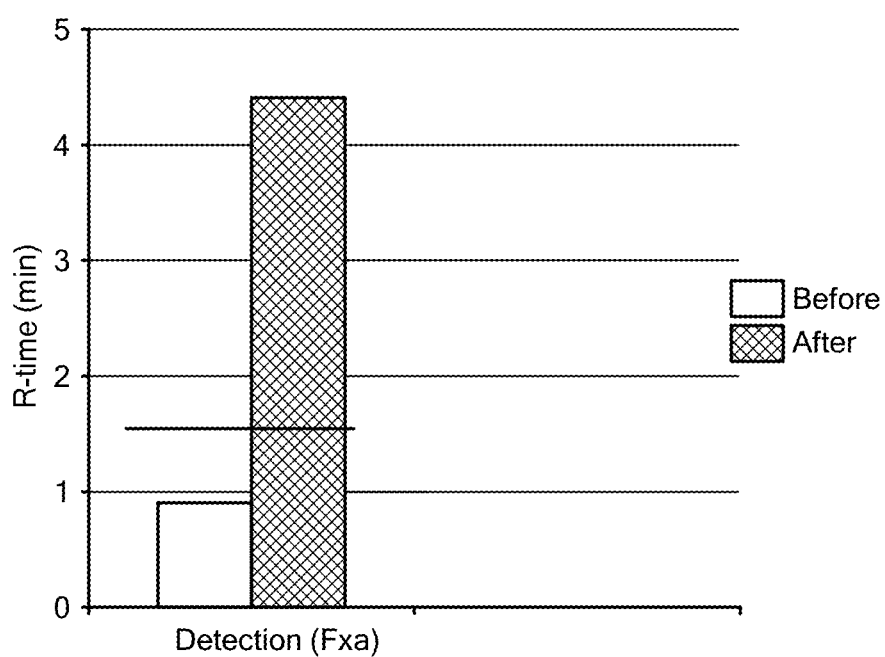

FIG. 15B shows the results of the "before" and "after" analyses (i.e., "after" analysis is the R times taken after the donor has been administered an anticoagulant drug) using thromboelastography in the presence of the FXa reagent. Blood was drawn 2 hours and 30 minutes after the donor patient was orally administered 20 mg Rivaroxaban, an anti-Xa drug. As in FIG. 15A, the horizontal line at approximately 1.5 minutes is the upper boundary of the reference range from multiple donors known to not be taking an anticoagulant in the presence of the FXa reagent (i.e., this is the reference range for the detection time). As shown in FIG. 15B, the "before" detection time is within (i.e., shorter than) the reference range of approximately 1.5 minutes. However, the "after" detection time (i.e., 2.5 hours after the donor was orally administered Rivaroxaban) is outside of the reference range of 1.5 minutes. In fact, the "after" detection time is approximately 4.4 minutes; accordingly in this study, the "after" detection time is 2.93 times longer than the reference range R time of 1.5 minutes. The "after" detection time (the R time) being outside of the reference range in the detection time indicates the presence of an anticoagulant (refer to FIG. 5).

Figure 15C:
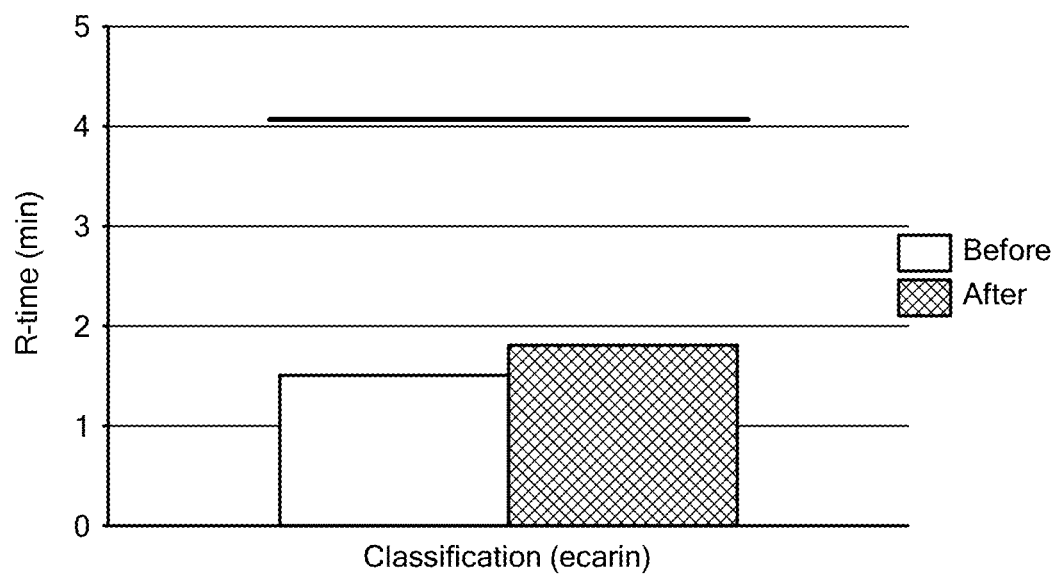

FIG. 15C shows the results of the "before" and "after" analyses (i.e., "after" analysis is the R times taken after the donor has been administered an anticoagulant drug) using thromboelastography in the presence of the ecarin reagent. Blood was drawn 2 hours and 30 minutes after the donor patient was orally administered 20 mg Rivaroxaban, an anti-Xa drug. As in FIG. 15A, the horizontal line at approximately 4.1 minutes is the upper boundary of the reference range in the presence of the ecarin reagent (i.e., this is the reference range for the classification time) as determined from multiple donors known to not be taking an anticoagulant. As shown in FIG. 15C, because the R results of the volunteer's "after" blood was within the Ecarin reference range of control blood (i.e., blood from donors known not to be taking an anticoagulant), the anticoagulant in the volunteer's blood was identified as being an anti-Factor Xa reagent and identified as not being a direct thrombin inhibitor (See also the decision tree in FIG. 6).

Thus, in FIGS. 15A-15C, using the FXa reagent and the ecarin reagent in combination with the thromboeastography clotting assay, analysis of blood from a volunteer taking (i.e., being administered) an anticoagulant was able to confirm that (a) the volunteer was taking an anticoagulant (as evidenced by the increased R time in the detection time in the presence of Factor Xa as compared to control blood) and (b) that the anticoagulant the volunteer was taking was an anti-Factor Xa reagent and was not a direct thrombin inhibitor reagent (as evidenced by an R-time within the reference range of control blood in the presence of Ecarin).

Example 5

New oral anticoagulants (OAC) do not require routine monitoring however measuring drug levels may be needed in clinical situations such as trauma and emergent surgery. Clinical or laboratory whole blood assays are not established for dabigatran. Thrombelastography (TEG®) has shown promising results in detecting and following dabigatran through changes in hemostatic parameters.

This study evaluated the effect of dabigatran and its specific reversal agent with the next generation fully automated TEG®6S system.

The TEG®6S system (Haemonetics Corp., Braintree, Mass.) is based on viscoelasticity measurements using resonance frequency and disposable multi-channel microfluidic cartridges. Blood and plasma from healthy volunteers were spiked with dabigatran in the therapeutic range (in increasing concentrations) and tested with an OAC cartridge with an ecarin based, direct thrombin inhibitor (DTI) channel. This channel was also evaluated with porcine plasma from an experimental trauma model (n=6) where dabigatran levels were measured with dilute TT (Hemoclot®). TEG 6s R-time (reaction time) was correlated to the drug levels.

Results: In Vitro:

R-time was highly correlated with dabigatran levels in whole blood ($r^2>0.95$). Significant correlation was also observed in plasma ($r^2>0.6$)

Trauma Model:

R-time was significantly correlated with dabigatran plasma levels ($r^2=0.7$). R-time at baseline was (3.4±0.6 min, n=4). Following dabigatran administration, significant elongation of R-time was observed pre and post trauma with R-times ≥21±5.9 min. Administration of the reversal agent idarucizumab returned R-time to baseline (3.6±0.6 min).

Table 4 summarizes how R time from different channels is analyzed to detect and classify the anticoagulants.

TABLE 4

| Factor Xa Reagent Result | Ecarin Reagent Result | Condition |
|---|---|---|
| Long R | Short R | Anti-Factor Xa |
| Long R | Long R | DTI |
| Short R | Short R | Healthy Normal |

Figure 16:
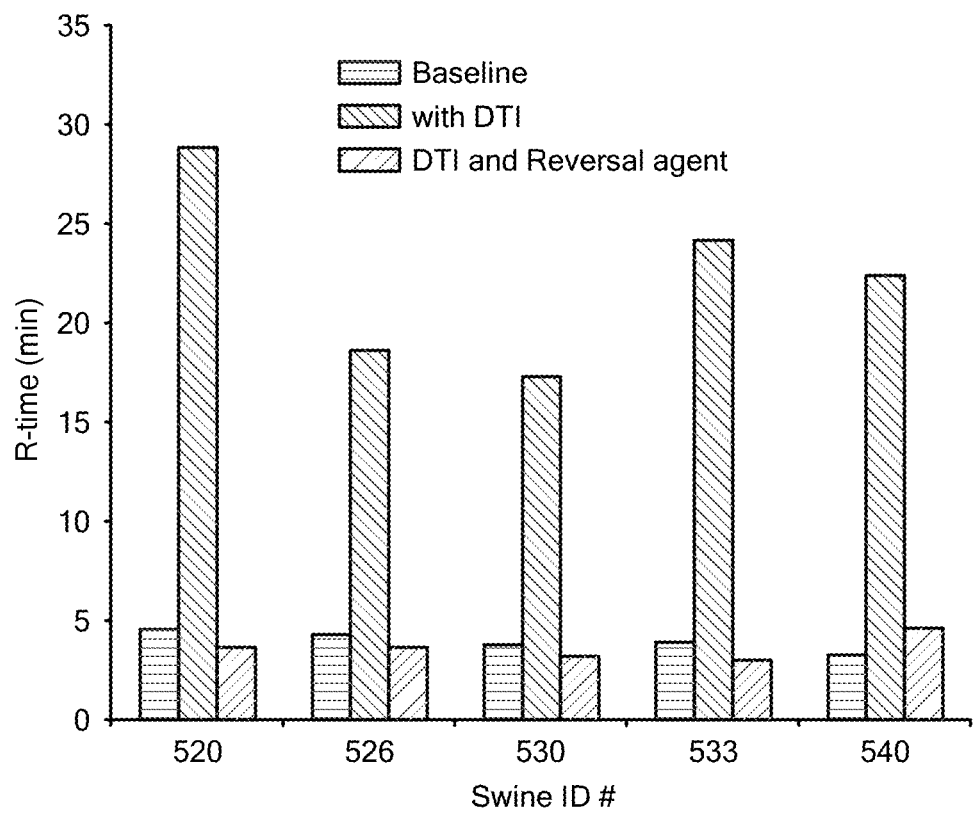
FIG. 16 is a bar graph demonstrating elongation of R-time in presence of a Direct thrombin Inhibitor (DTI, red bars) followed by shortening of the R-time to baseline when a reversal agent (green bars) was administered in swine plasma samples. Baseline is shown as a blue bar.

The bar graph shown in FIG. 16 shows how in five separate swine plasma samples, R time is elongated in the presence of a DTI anticoagulant (red bars); however, upon administration of the idarucizumab reversal agent, the R time (green bar) returned to baseline (blue bars). Thus, when a sample is analyzed using the methods described herein, the identification and classification of an anticoagulant in the sample allows selected reversal of that anticoagulant.

CONCLUSION

TEG® 6s has the potential to measure the effect of dabigatran on the hemostasis system effectively in whole blood as well as plasma in a clinical setting. This novel technology is fully automated and can provide clinically relevant results with whole blood in as little as 5 minutes.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for treating a patient suspected of having either an anti-Factor Xa or a direct thrombin inhibitor (DTI) anticoagulant at a therapeutically relevant amount or higher, the method comprising:
   a. detecting the anticoagulant by:
      i. obtaining a sample of a blood component from the patient,
      ii. performing a first viscoelastic clotting assay in the presence of a Factor Xa reagent in a first sample of a blood component from the patient to obtain a patient Factor Xa clotting measurement;
      iii. obtaining a control sample of a blood component that lacks an anticoagulant;
      iv. and performing a viscoelastic clotting assay in the presence of a Factor Xa reagent in the control sample to obtain a control Factor Xa clotting measurement;
   wherein the presence of the anti-Factor Xa anticoagulant and the presence of the DTI anticoagulant are capable of being detected;
   wherein the patient Factor Xa clotting measurement that is at least 1.25 times greater than the control Factor Xa clotting measurement indicates the presence of the anti-Factor Xa anticoagulant or the presence of the DTI anticoagulant at a therapeutically relevant amount or higher in the patient, and
   wherein the patient Factor Xa clotting measurement less than or equal to the control Factor Xa clotting measurement indicates the absence of both the anti-Factor Xa anticoagulant and the DTI anticoagulant at a therapeutically relevant amount or higher in the patient; and
   b. if the presence of the anti-Factor Xa anticoagulant or the presence of the DTI anticoagulant at a therapeutically relevant amount or higher in the patient is detected, classifying the anticoagulant by:
      i. obtaining a second sample of a blood component from the patient identified as having an anticoagulant at a therapeutically relevant amount or higher;
      ii. performing a second viscoelastic analysis clotting assay to obtain a patient ecarin clotting measurement;
      iii. obtaining a control sample of a blood component that lacks an anticoagulant; and
      iv. performing a viscoelastic clotting assay in the presence of an ecarin reagent in the control sample to obtain a control ecarin clotting measurement;
   wherein a patient ecarin clotting measurement that is at least 1.25 times greater than the control ecarin clotting measurement identifies the detected anticoagulant as the DTI anticoagulant in the patient, and wherein a patient ecarin clotting measurement less than or equal to the control ecarin clotting measurement identifies the detected anticoagulant as the anti-Factor Xa anticoagulant in the patient; and
   administering to the patient identified as having a DTI anticoagulant a therapeutically relevant amount of a reversal agent that reverses the DTI anticoagulant, or administering to the patient identified as having an anti-Factor Xa a therapeutically relevant amount of a reversal agent that reverses the anti-Factor Xa anticoagulant.

2. The method of claim 1, wherein the viscoelastic analysis is performed using a container containing the sample on an interior of the container.

3. The method of claim 2, wherein the viscoelastic analysis is performed using the container and a pin, wherein the pin moves relative to the container or the container moves relative to the pin.

4. The method of claim 2, wherein the container lacks a bottom surface.

5. The method of claim 1, wherein the patient is a human.

6. The method of claim 1, wherein the patient is undergoing a condition selected from the group consisting of: surgery, trauma, bleeding, stroke and a thromboembolic event.

7. The method of claim 1, wherein the anticoagulant is an oral anticoagulant.

8. The method of claim 1, wherein the control Factor Xa clotting measurement is a range, average or median of at least two Factor Xa clotting measurements of at least two control blood components known to lack the anticoagulant.

9. The method of claim 1, wherein the control ecarin clotting measurement is a range, average or median of at least two ecarin clotting measurements of at least two control blood components known to lack the anticoagulant.

10. The method of claim 1, wherein the reversal agent that reverses the DTI anticoagulant is selected from the group consisting of prothrombin complex concentrate (PCC) and idarucizumab.

11. The method of claim 1, wherein the reversal agent that reverses the anti-Factor Xa anticoagulant is andexanet.

\* \* \* \* \*